(12) United States Patent
LaColla et al.

(10) Patent No.: US 6,710,068 B2
(45) Date of Patent: Mar. 23, 2004

(54) PHENYLINDOLES FOR THE TREATMENT OF HIV

(75) Inventors: Paulo LaColla, Cagliari (IT); Marino Artico, Rome (IT); Jean-Pierre Sommadossi, Cambridge, MA (US)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/122,252

(22) Filed: Apr. 11, 2002

(65) Prior Publication Data

US 2002/0193415 A1 Dec. 19, 2002

Related U.S. Application Data

(60) Provisional application No. 60/283,393, filed on Apr. 11, 2001.

(51) Int. Cl.[7] .................... C07D 209/04; A61K 31/404
(52) U.S. Cl. .................. 514/414; 548/465; 548/484; 544/143; 514/235.2; 514/418
(58) Field of Search .............................. 514/419, 235.2, 514/414, 418; 548/491, 465, 484; 544/143

(56) References Cited

U.S. PATENT DOCUMENTS

| | | | |
|---|---|---|---|
| 4,866,084 A | 9/1989 | Gunasekera et al. |
| 5,124,327 A | 6/1992 | Greenlee et al. |
| 5,489,685 A | 2/1996 | Houpis et al. |
| 5,527,819 A | 6/1996 | Williams et al. |
| 5,830,894 A | 11/1998 | Pevear et al. |
| 5,852,011 A | 12/1998 | Matsunaga et al. |
| 5,929,114 A | 7/1999 | Domagala et al. |
| 5,935,982 A | 8/1999 | Dykstra et al. |
| 5,945,440 A | 8/1999 | Kleinschroth et al. |
| 5,981,525 A | 11/1999 | Farina et al. |
| 6,025,390 A | 2/2000 | Farina et al. |

FOREIGN PATENT DOCUMENTS

| | | |
|---|---|---|
| WO | WO 94/19321 | 9/1994 |

OTHER PUBLICATIONS

Clauson–Kaas, N. et al., *Acta Chem. Scand.*, 1952, 6, 667–670.
Elming, N., *Acta Chem. Scand.*, 1952, 6, 867–874.
Gagliardi, S. et al., *J. Med. Chem.*, 1998, 41, 1568–1573.
Pauwels, R. et al. *Nature*, 1990, 343, 470–474.
Pauwels, R. et al. *Proceedings of the National Academy of Sciences USA*, 1993, 90, 1711–1715.
Romero, D.L. et al., *J. Med. Chem.*, 1993, 36, 1505–1508.
"The Japp–Klingemann reaction," *Org. Reactions*, 1959, 10, 143–178.
Williams et al., *Journal of Medicinal Chemistry*, 1993, 36(9), 1291–94.
Balani et al., *Drug Metab and Dispo.*, 1993, vol. 21 (4), pp. 598–604.

*Primary Examiner*—Joseph K. McKane
*Assistant Examiner*—Golam M M Shameem
(74) *Attorney, Agent, or Firm*—Sherry M. Knowles; King & Spalding LLP

(57) ABSTRACT

The invention as disclosed herein is a method and composition for the treatment of HIV in humans and other host animals, that includes the administration of an effective HIV treatment amount of a phenylindole as described herein or a pharmaceutically acceptable salt or prodrug thereof, optionally in a pharmaceutically acceptable carrier. The compounds of this invention either possess antiviral (i.e., anti-HIV) activity, or are metabolized to a compound that exhibits such activity.

14 Claims, 6 Drawing Sheets

PHENYLINDOLES FOR THE TREATMENT OF HIV

This application claims priority to U.S. Provisional Application No. 60/283,393, filed on Apr. 11, 2001.

FIELD OF THE INVENTION

This invention is in the area of phenylindoles that are useful for the treatment of HIV infection, and, in particular, phenylindoles that exhibit significant activity against resistant strains of HIV.

BACKGROUND OF THE INVENTION

In 1983, the etiological cause of AIDS was determined to be the human immunodeficiency virus (HIV). Numerous compounds have since been synthesized to combat the virus, designed to inhibit progression beyond various stages of the virus's lifecycle. A focal point in AIDS research efforts has been the development of inhibitors of human immunodeficiency virus (HIV-1) reverse transcriptase (RT), an enzyme responsible for the reverse transcription of the retroviral RNA to proviral DNA (Greene, W. C., New England Journal of Medicine, 1991, 324, 308–317; Mitsuya, H. et al., Science, 1990, 249, 1533–1544; De Clercq, E., J. Acquired Immune Defic. Syndr. Res. Human. Retrovirus, 1992, 8, 119–134). Promising inhibitors include nonnucleoside inhibitors (NNI), which bind to a specific allosteric site of HIV-1 RT near the polymerase site and interfere with reverse transcription by altering either the conformation or mobility of RT, thereby leading to noncompetitive inhibition of the enzyme (Kohlstaedt, L. A. et al., Science, 1992, 256, 1783–1790).

Several classes of compounds have been identified as NNI of HIV-1 RT. Examples include the following:

(a) 1-[(2-hydroxyethoxy)methyl]-6-(phenylthio)thymines (HEPT; Tanaka, H. et al., J. Med. Chem., 1991, 34, 349–357; Pontikis, R. et al., J. Med. Chem., 1997, 40, 1845–1854; Danel, K., et al., J. Med. Chem., 1996, 39, 2427–2431; Baba, M., et al., Antiviral Res, 1992, 17, 245–264);

(b) bis(heteroaryl)piperazines (BHAP; Romero, D. L. et al., J. Med. Chem., 1993, 36, 1505–1508);

(c) dihydroalkoxybenzyloxopyrimidine (DABO; Danel, K. et al., Acta Chemica Scandinavica, 1997, 51, 426–430; Mai, A. et al., J. Med. Chem., 1997, 40, 1447–1454);

(d) 2'-5'-bis-O-(tertbutyldimethylsilyl)-3'-spiro-5"-(4"-amino-1", 2"-oxathiole-2", 2"-dioxide) pyrimidines (TSAO; Balzarini, J. et al., Proc. Natl. Acad. Sci. USA, 1992, 89, 4392–4396);

(e) phenethylthiazolylthiourea (PETT) derivatives (Bell, F. W. et al., J. Med. Chem., 1995, 38, 4929–4936; Cantrell, A. S. et al., J. Med. Chem., 1996, 39, 4261–4274);

(f) tetrahydro-imidazo[4,5,1-jk][1,4]-benzodiazepine-2(1H)-one and -thione (TIBO) derivatives (Pauwels, R. et al. Nature, 1990, 343, 470–474);

(g) alpha-anilinophenylacetamide (alpha-APA) derivatives (Pauwels, R. et al. Proceedings of the National Academy of Sciences USA, 1993, 90, 1711–1715); and (h) indole derivatives (Williams et al., U.S. Pat. No. 5,527,819 (Jun. 18, 1996); and its counterpart PCT application PCT/US94/01694, published as WO 94/19321 on Sep. 1, 1994).

The indole derivatives identified by Williams et al., assigned to Merck & Co., in U.S. Pat. No. 5,527,819 received particular interest because of their ability to potently inhibit HIV reverse transcriptase. A number of these compounds displayed $EC_{90}$s against HIV reverse transcriptase at concentrations as low as 2 micromolar. However, this work was not pursued, perhaps because HIV virus that had been exposed to other drugs was shown to be cross resistant to these indoles (Williams et al., Journal of Medicinal Chemistry, 1993, 36(9), 1291–94).

The class of compounds disclosed in the '819 patent encompasses a large class of compounds represented generally by the following broad structural formula:

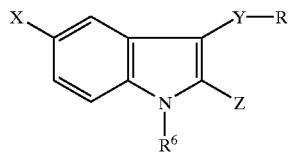

in which the variables X, Y, Z, R and $R^6$ were broadly defined to encompass a plethora of compound$_S$. The patent presented examples for nearly one hundred of the compounds encompassed by the structure, and included several examples in which Z was —C(O)$NH_2$, Y was $SO_2$ and R was phenyl or substituted phenyl.

U.S. Pat. No. 5,124,327, issued Jun. 23, 1992 to Greenlee et al. and assigned to Merck disclosed a class of compounds of the general formula above, in which X is H, $R^6$ is H, Y is S, and R is phenyl. The patent disclosed that the compounds act as reverse transcriptase inhibitors.

Indoles have been used for the treatment of a variety of diseases other than HIV. For example, Farina et al., in U.S. Pat. No. 5,981,525 (Nov. 9, 1999), disclose a complex array of indoles that are useful for the treatment of osteoporosis, because they reduce bone resorption by inhibiting osteoclast $H^+$-ATPase.

U.S. Pat. No. 6,025,390, granted Feb. 15, 2000 to Farina et al., discloses another complex array of indole derivatives, referred to as heteroaromatic pentadienoic acid derivatives, and again suggest their use for the treatment of osteoporosis.

U.S. Pat. No. 5,489,685, granted Feb. 6, 1996, Houpis et al. discloses a similar set of compounds in the furo(2,3-B) pyridine carboxylic acid ester class, and specifically suggest their use for the treatment of HIV.

U.S. Pat. No. 5,945,440 to Kleinschroth et al. discloses a class of indolocarbazole amides, and proposes their use for a variety of diseases including cancer, viral diseases (including HIV), heart and blood vessel diseases, bronchopulmonary diseases, degenerative diseases of the central nervous system, inflammatory disorders, and other diseases.

Gunasekera et al., in U.S. Pat. No. 4,866,084 (Sep. 12, 1989), disclose a class of bisindole alkaloid compounds, and state that the compounds are useful as antiviral and antitumor agents. The patent also describes the compounds' activity against HSV (herpes simplex virus).

Matsunaga et al., in U.S. Pat. No. 5,852,011 (Dec. 22, 1998), disclose a class of indole derivates substituted by a heteroaryl function and an amide function. The compounds are said to possess antitumor, antiviral, and antimicrobial properties.

Dykstra et al., in U.S. Pat. No. 5,935,982 disclose a class of bis-indoles and specifically propose their use for treating retroviral infections, and especially infection by HIV.

Domagala et al., in U.S. Pat. No. 5,929,114 (Jul. 27, 1999) disclose a class of arylthio and bithiobisarylamide compounds that reportedly have antibacterial and antiviral activity. The invention is said to encompass indole derivatives as well.

Pevear et al., in U.S. Pat. No. 5,830,894 (Nov. 3, 1998) disclose a class of triazinoindole derivatives that reportedly have pestivirus activity, most notably BVDV activity.

It is known that over a period of time, antiviral agents that are active against HIV induce mutations in the virus that reduce the efficacy of the drug. This was apparently the problem exhibited by the Merck indoles in U.S. Pat. No. 5,527,819 (Williams et al., *Journal of Medicinal Chemistry*, 1993, 36(9), 1291–94). Drug resistance most typically occurs by mutation of a gene that encodes for an enzyme used in viral replication, and most typically in the case of HIV, reverse transcriptase, protease, or DNA integrase. It has been demonstrated that the efficacy of a drug against HIV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameters of a drug can be altered by such combination or alternation therapy. In general, combination therapy is typically preferred over alternation therapy since combination therapy induces multiple simultaneous pressures on the virus. However, one cannot predict which mutations will be induced in the HIV-1 genome by a given drug, whether the mutations are permanent or transient, or how an infected cell with a mutated HIV-1 sequence will respond to therapy with other agents in combination or alternation. These factors are exacerbated by the fact that there is a paucity of data on the kinetics of drug resistance in long-term cell cultures treated with modem antiretroviral agents.

Therefore, there is a need to improve the duration of antiviral efficacy produced by antiretroviral drugs, and to provide antiviral drugs that are effective against strains of the virus that have developed cross resistance through mutational adaptation. Further, although many of the non-nucleotide reverse transcriptase inhibitors (NNRTI) in the prior art exhibit favorable pharmacokinetic and biodistribution profiles, there remains a need to improve upon these parameters.

It is an object of the present invention to provide new compounds for the treatment of patients infected with HIV. There is a special need to provide new compositions and methods for the treatment of patients infected with HIV that exhibit significant activity against drug-resistant forms of the virus.

SUMMARY OF THE INVENTION

A novel class of phenylindoles has been discovered that display significant antiviral activity against HIV, and in particular, strains of the HIV that have developed cross resistance to other anti-HIV drugs. It has surprisingly been discovered that HIV activity can be enhanced, and in certain cases cross resistance can be substantially overcome, by incorporating into the molecule at least two moieties other than hydrogen on either the phenyl ring or the benzyl ring of the indole function, or on both rings. The substituents are preferably contained at the 3" and 5" positions if located on phenyl ring, and at the 4' and 5'; 5' and 6' or the 5' and 7' positions if located on the benzyl ring of the indole function. Methyl is a preferred group for substitution on the phenyl ring. Preferred substituents for the benzyl ring of the indole function are small moieties, and include substituents such as chlorine, fluorine, bromine, $CF_3$, vinyl bromide and $NO_2$.

In one embodiment of the present invention, the compound can be represented generally by the following chemical formula:

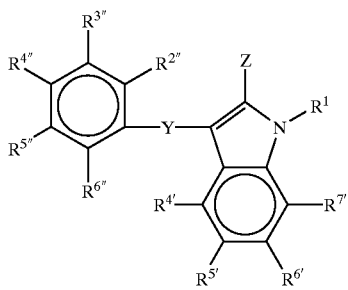

or its pharmaceutically acceptable salt or prodrug, wherein (a) $R^1$ is hydrogen; acyl; —C(=O)H; —C(=W)H; —C(=O)$R^2$; —C(=W)$R^2$; —C(=O)OH; —C(=W)OH; —C(=O)O$R^2$; —C(=W)O$R^2$; —C(=O)SH; —C(=W)SH; —C(=O)S$R^2$; —C(=W)S$R^2$; —C(=O)$NH_2$; —C(=W)$NH_2$; —C(=O)NH$R^2$; —C(=W)NH$R^2$; —C(=O)NR2RW; —C(=W)N$R^2R^3$; —C(=W)NH—$(CH_2)_p$-(amino acid) or —$(CH_2)_p$-(amino acid);

(b) $R^{4'}$, $R^{5'}$, $R^{6'}$, $R^{7'}$, $R^{2''}$, $R^{3''}$, $R^{4''}$, $R^{5''}$ and $R^{6''}$ are each independently H; halo (F, Cl, Br or I); —$NO_2$; —CN; —OH; —O$R^2$; —SH; —S$R^2$; —$NH_2$; —NH$R^2$; —N$R^2R^3$; —NH$SO_2$—$C_{1-3}$alkyl; —N$R^2SO_2$—$C_{1-3}$alkyl; —NHCO—$C_{1-3}$alkyl; —N$R^2$CO—$C_{1-3}$alkyl; optionally substituted or unsubstituted branched or unbranched alkyl, alkenyl or alkynyl (such as an optionally substituted or unsubstituted branched or unbranched $C_{1-6}$alkyl, $C_{2-6}$alkenyl or $C_{2-6}$alkynyl, and in particular $CH_3$, $CF_3$, vinyl bromide, —$CR^2R^2$—S(O)$_n$—$R^3$, —$CR^2R^2NH_2$, —$CR^2R^2$NH$R^2$, —$CR^2R^2NR^2R^3$ and —$CR^2R^2$—C(=O)$R^2$); alkacyl; optionally substituted or unsubstituted acyl; —C(=O)H; —C(=W)H; —C(=O)$R^2$; —C(=W)$R^2$; —C(=O)OH; —C(=W)OH; —C(=O)O$R^2$; —C(=W)O$R^2$; —C(=O)—SH; —C(=W)SH; —C(=O)S$R^2$; —C(=W)S$R^2$; —C(=O)$NH_2$; —C(=W)$NH_2$; —C(=O)NH$R^2$; —C(=W)NH$R^2$; —C(=O)N$R^2R^3$; —C(=W)—N$R^2R^3$, —C(=W)NH$(CH_2)_p$-(amino acid), a residue of an amino acid or —$(CH_2)_p$(amino acid); wherein if $R^{5'}$ is hydrogen, F, Cl, Br, —$NO_2$, —CN, —O$R^2$, —N$R^2R^2$, —NH$SO_2$—$C_{1-3}$alkyl or —NHCO—$C_{1-3}$alkyl, then at least one of $R^{4'}$, $R^{6'}$ and $R^{7'}$ is not hydrogen or alternatively, wherein at least two of $R^{4'}$, $R^{5'}$, $R^{6'}$, $R^{7'}$ are not hydrogen.

(c) Z is optionally substituted or unsubstituted acyl, —C(=O)$NH_2$; —C(=W)—$NH_2$; —C(=O)NH$R^2$; —C(=W)NH$R^2$; —C(=O)N$R^2R^3$; —C(=W)N$R^2R^3$; —C(=W)NH$(CH_2)_p$-(amino acid); a residue of an amino acid, —$(CH_2)_p$-(amino acid); —C(=O)$R^3$; —C(=O)H; —C(=W)H; —C(=O)$R^2$; —C(=W)$R^2$; —C(=O)O$R^3$; —C(=O)OH; —C(=W)OH; —C(=O)O$R^2$; —C(=W)—O$R^2$; —C(=O)—SH; —C(=W)SH; —C(=O)S$R^2$; —C(=W)S$R^2$; optionally substituted or unsubstituted branched or unbranched alkyl, alkenyl or alkynyl (such as an optionally substituted or unsubstituted branched or unbranched $C_{1-6}$alkyl, $C_{2-6}$alkenyl or $C_{2-6}$alkynyl, and in particular $CH_3$, $CF_3$, vinyl bromide, —$CR^2R^2$—S(O)$_n$—$R^3$, —$CR^2R^2NH_2$, —$CR^2R^2$NH$R^2$, —$CR^2R^2NR^2$, $R^3$ and —$CR^2R^2$—C(=O)$R^2$); —CN, or halo (F, Cl, Br or I);

(d) Y is O, S or S(O)$_n$;

(e) each W is independently O, S, —$NH_2$, —NH$R^2$, —N$R^2R^2$, —N—CN, —N—$NH_2$, —N—NH$R^2$, —N—N$R^2R^3$, —N—OH or —N—O$R^2$;

(f) each $R^2$ is independently hydrogen or an optionally substituted or unsubstituted branched or unbranched lower alkyl, alkenyl or alkynyl (such as an optionally substituted or unsubstituted branched or unbranched $C_{1-3}$alkyl, $C_{2-4}$alkenyl or $C_{2-4}$alkynyl, and in particular $CH_3$, $CF_3$, vinyl bromide, $-CR^2R^2-S(O)_n-R^3$, $-CR^2R^2NH_2$, $-CR^2R^2NHR^2$, $-CR^2R^2NR^2R^3$ and $-CR^2R^2-C(=O)R^2$);

(g) each $R^3$ is independently hydrogen; optionally substituted or unsubstituted branched or unbranched alkyl, alkenyl or alkynyl (such as an optionally substituted or unsubstituted branched or unbranched $C_{1-6}$alkyl, $C_{2-6}$alkenyl or $C_{2-6}$alkynyl, and in particular $CH_3$, $CF_3$, vinyl bromide, $-CR^2R^2-S(O)_n-R^3$, $-CR^2R^2NH_2$, $-CR^2R^2NHR^2$, $-CR^2R^2NR^2R^3$ and $-CR^2R^2-C(=O)R^2$); optionally substituted or unsubstituted aryl (such as phenyl); optionally substituted or unsubstituted heterocycle; optionally substituted or unsubstituted alkylaryl, optionally substituted or unsubstituted alkylhereterocycle, optionally substituted or unsubstituted aralkyl, optionally substituted or unsubstituted heterocycle-alkyl;

(h) each n is independently 0, 1 or 2; and (i) each p is independently 0, 1, 2, 3, 4 or 5;

(j) wherein if one or more of the optionally substituted branched or unbranched alkyl, alkenyl, alkynyl, lower alkyl, lower alkenyl or lower alkynyl; acyl; aryl; heterocycle; alkaryl; alkheterocycle; arylalkyl or alkylheterocycle substitutents is substituted, then preferably it is substituted with one or more of halogen (F, Cl, Br or I), $-OH$, $-OR^2$, $-SH$, $-SR^2$, oxime (defined herein as $-CH=N-OH$), hydrazine (defined herein as $-NH-NH_2$), $-C(=O)H$, $-C(=W)H$, $-C(=O)R^2$, $-C(=W)R^2$, $-C(=O)OH$, $-C(=W)OH$, $-C(=O)OR^2$, $-C(=W)OR^2$, $-C(=O)SH$, $-C(=W)SH$, $-C(=O)SR^2$, $-C(=W)SR^2$, $-C(=O)NH_2$, $-C(=W)NH_2$, $-C(=O)-NHR^2$, $-C(=W)NHR^2$, $-C(=O)NR^2R^3$, $-C(=W)-NR^2R^3$, $-NH_2$, $-NHR^2$, $-NR^2R^3$, $-NHSO_2-C_{1-3}$alkyl, $-NW^2SO_2-C_{1-3}$alkyl, $-NHCO-C_{1-3}$alkyl, $-NR^2CO-C_{1-3}$alkyl, $-S(O)_n-R^3$, $C_{1-3}$alkoxy, $C_{1-3}$thioether, a residue of an amino acid such as $-NH(CH_2)_p$-(amino acid) or $-C(=W)NH(CH_2)_p$-(amino acid).

In a preferred embodiment, Y is $SO_2$. In another preferred embodiment, Z is an amide function.

In an alternative embodiment, the hydrogen attached to the indole nitrogen can be replaced with lower alkyl, for example, methyl, or aryl, alkaryl or aralkyl.

In another embodiment the invention provides a phenylindole represented generally by formula (I) above, and methods of using such phenylindoles in the treatment of HIV, wherein:

(a) $R^1$ is hydrogen;

(b) $R^{4'}$, $R^{5'}$, $R^{6'}$ and $R^{7'}$ are independently hydrogen, halogen (F, Cl, Br or I), $-NO_2$, $-CN$, $-OR^2$, $-NR^2R^2$, $-NHSO_2-C_{1-3}$alkyl, $-NHCO-C_{1-3}$alkyl, oxime, hydrazine, or $C_{1-3}$ alkyl or alkenyl optionally substituted with one or more of $-OH$, $-SH$, $-C(O)H$, $-COOH$, halogen (F, Cl, Br or I), $-NR^2R^2$, $-C_{1-3}$ alkoxy or $-C_{1-3}$ thioether; wherein if $R^{5'}$ is hydrogen, F, Cl, Br, $-NO_2$, $-CN$, $-OR^2$, $-NR^2R^2$, $-NHSO_2-C_{1-3}$alkyl or $-NHCO-C_{1-3}$ alkyl, then at least one of $R^{4'}$, $R^{6'}$ and $R^{7'}$ is not hydrogen;

(c) $R^{2''}$, $R^{3''}$, $R^{4''}$, $R^{5''}$ and $R^{6''}$ are independently hydrogen, halogen (F, Cl, Br or I), $-NO_2$, $-CN$, $-OH$, $-OR^2$, $-NR^2R^2$, $-NHSO_2-C_{1-3}$alkyl, $-NHCO-C_{1-3}$ alkyl, $-C_{1-5}$ alkoxy, oxime, hydrazine, $-C_{1-5}$ alkyl or alkenyl optionally substituted with one or more of $-OH$, $-SH$, $-C(O)H$, $-COOH$, halogen (F, Cl, Br or I), $-NR^2R^2$, $-C_{1-5}$ thioether or $-C_{1-5}$ alkoxy;

(d) Z is $-CN$, $-C(=W)NR^2R^3$, $-C(=O)R^3$, $-C(=O)OR^3$, $-CR^2R^2-S(O)_n-R^3$, $-CR^2R^2NHR^2$, $-CR^2R^2-CO-R^3$ or substituted or unsubstituted lower alkyl;

(e) Y is O, S, or $S(O)_n$;

(f) each W is independently O, S, $-N-CN$ or $-N-OR^2$;

(g) $R^2$ is hydrogen or $C_{1-3}$ alkyl;

(h) $R^3$ is hydrogen, substituted or unsubstituted alkyl, alkenyl, aryl, or heterocycle, $-C_{1-5}$ alkoxy, $-OH$, $-NR^2R^2$, or $-(CH_2)_pC(O)NR^2R^2$, (i) each n is independently 0, 1 or 2; and (j) each p is independently 0, 1, 2, 3, 4, or 5.

In still another embodiment the invention provides a phenylindole represented generally by formula (I) above, and methods of using such phenylindoles in the treatment of HIV, wherein:

(a) $R^1$ is hydrogen;

(b) $R^{4'}$, $R^{5'}$, $R^{6'}$, $R^{7'}$, are independently hydrogen, halogen (F, Cl, Br or I), $-NO_2$, $-CN$, $-OR^2$, $-NR^2R^2$, $-NHSO_2-C_{1-3}$alkyl, $-NHCO-C_{1-3}$alkyl, oxime (defined herein as $-CH=N-OH$), hydrazine (defined herein as $-NH-NH_2$), or $C_{1-3}$ alkyl or alkenyl optionally substituted with one or more of $-OH$, $-SH$, $C(O)H$, COOH, halogen, $NR^2R^2$, $C_{1-3}$ alkoxy, or $C_{1-3}$ thioether; wherein if $R^{5'}$ is hydrogen, F, Cl, Br, $-NO_2$, $-CN$, $-OR^2$, $-NR^2R^2$, $-NHSO_2-C_{1-3}$alkyl or $-NHCO-C_{1-3}$alkyl, then at least one of $R^{4'}$, $R^{6'}$ and $R^{7'}$ is not hydrogen;

(c) $R^{2''}$, $R^{3''}$, $R^{4''}$, $R^{5''}$, and $R^{6'''}$, are independently hydrogen, halogen (F, Cl, Br or I), $-NO_2$, $-CN$, $-OR^2$, $-NHSO_2-C_{1-3}$alkyl, $-NHCO-C_{1-3}$alkyl, oxime, hydrazine, $-C_{1-5}$ alkyl or alkenyl optionally substituted with one or more of $-OH$, $-SH$, $C(O)H$, COOH, halogen, $NR^2R^2$, $C_{1-5}$ thioether, or $C_{1-5}$ alkoxy, $-C_{1-5}$ alkoxy, $-OH$, or $-NR^2R^2$, (d) Z is $-C(W)NR^2R^3$, or $-COR^3$, (e) Y is $-S(O)_n-$ or $-O-$, in which n is 0, 1 or 2.

(f) W is O, S, $-N-CN$ or $-N-OR^2$;

(g) $R^2$ is hydrogen or $C_{1-3}$ alkyl, (h) $R^3$ is s alkyl, $C_{1-5}$ alkenyl, aryl, or heterocycle, substituted with one or more of $C(O)NR^2R^2$, $-NR^2R^2$, $-(CH_2)_mC(O)NR^1R^2$, $-(CH_2)_mC(=W)-NH(CH_2)_p$-(amino acid);

(k) each n is independently 0, 1 or 2; and (l) each p is independently 0, 1, 2, 3, 4, or 5.

In a particular embodiment, the phenylindole is a compound of the structure:

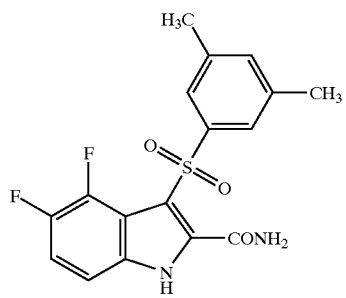

or a pharmaceutically acceptable salt or prodrug thereof.

In another particular embodiment, the phenylindole is a compound of the structure:

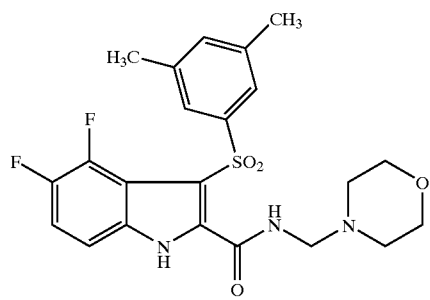

or a pharmaceutically acceptable salt or prodrug thereof.

In yet another particular embodiment, the phenylindole is a compound of the structure:

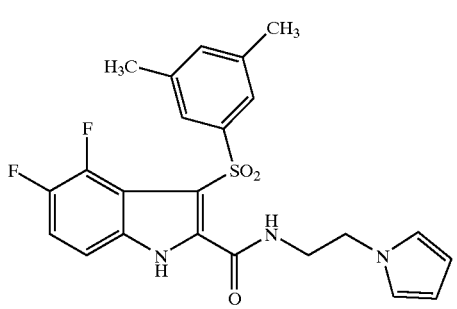

or a pharmaceutically acceptable salt or prodrug thereof.

In yet another particular embodiment, the phenylindole is a compound of the structure:

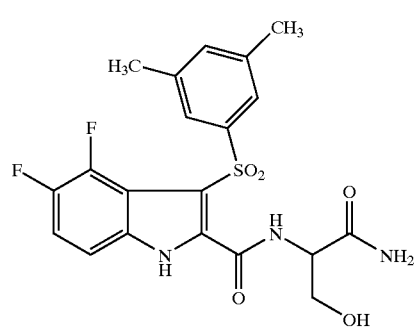

or a pharmaceutically acceptable salt or prodrug thereof.

In another particular embodiment, the phenylindole is a compound of the structure:

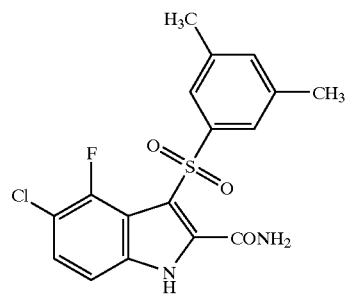

or a pharmaceutically acceptable salt or prodrug thereof.

In yet another particular embodiment of the present invention, the phenylindole is a compound of the structure:

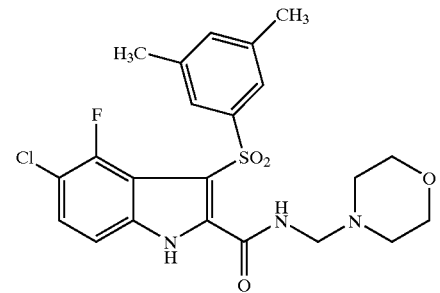

or a pharmaceutically acceptable salt or prodrug thereof.

In yet another particular embodiment of the present invention, the phenylindole is a compound of the structure:

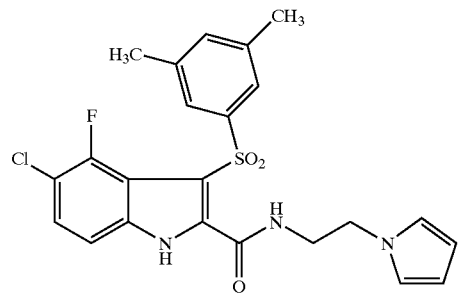

or a pharmaceutically acceptable salt or prodrug thereof.

In yet another particular embodiment of the present invention, the phenylindole is a compound of the structure:

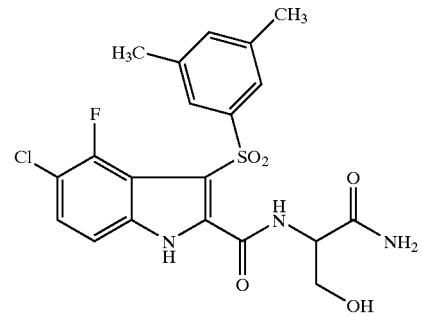

or a pharmaceutically acceptable salt or prodrug thereof.

The phenylindoles of this invention belong to a class of anti-HIV agents that may inhibit reverse transcriptase activity. These compounds can be assessed for their ability to inhibit reverse transcriptase activity in vitro according to standard screening methods.

In one embodiment the efficacy of the anti-HIV compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or preferably, less than 10 micromolar in vitro.

In another embodiment, the active compound exhibits significant activity against drug-resistant forms of HIV, and thus exhibits decreased cross-resistance against currently approved antiviral therapies. The term significant activity against a drug resistant form of HIV means that a compound (or its prodrug or pharmaceutically acceptable salt) is active against the mutant strain with an $EC_{50}$ against the mutant strain of less than approximately 50, 25, 10 or 1 micromolar concentration. In a preferred embodiment, the non-nucleosides reverse transcriptase inhibitors (NNRTI) displays an $EC_{50}$ (in molar concentrations) in a mutant HIV strain of less than approximately 5, 2.5, 1 or 0.1 micromolar concentration. In one non limiting embodiment, the HIV mutant strain is a strain with a reverse transcriptase mutation at lysine 103→ asparagine and/or tyrosine 181→ cysteine.

In still another embodiment, the active compound can be administered in combination or alternation with another anti-HIV agent. In combination therapy, effective dosages of two or more agents are administered together, whereas during alternation therapy an effective dosage of each agent is administered serially. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

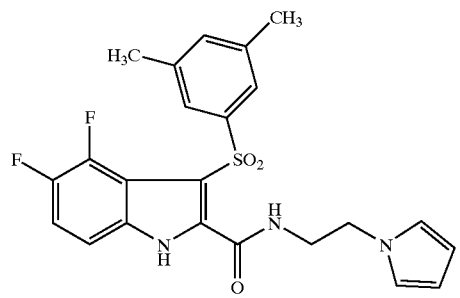

DETAILED DESCRIPTION OF THE INVENTION

Figure 1:
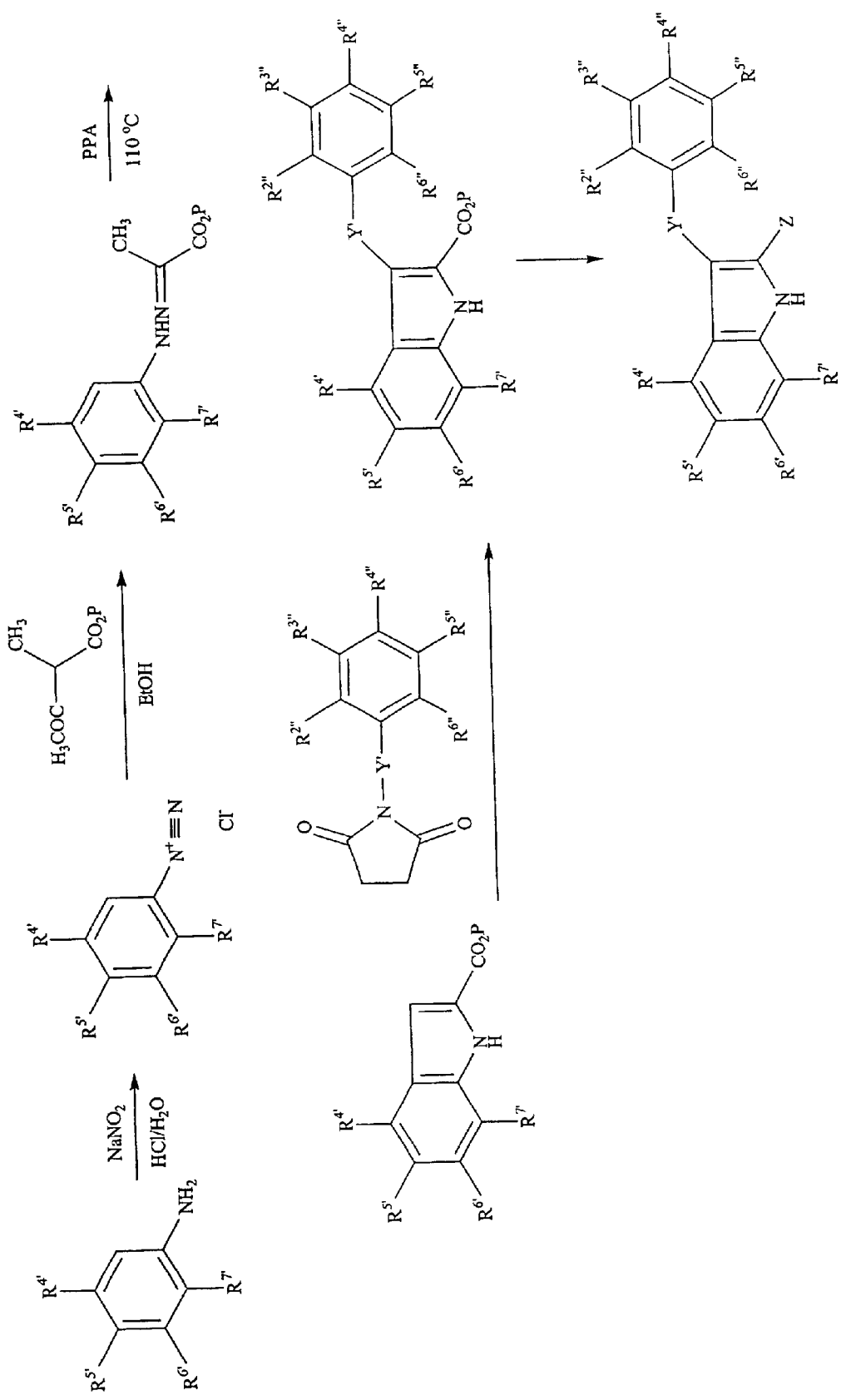
FIG. 1 is a nonlimiting illustrative example of the synthesis of phenylindoles as described herein; wherein P represents hydrogen or alkyl, in particular methyl, ethyl, butyl or propyl, preferably ethyl; and Y' represents oxygen or sulfur.

The invention as disclosed herein is a method and composition for the treatment of HIV in humans and other host animals, that includes the administration of an effective HIV treatment amount of a phenylindole as described herein or a pharmaceutically acceptable salt or prodrug thereof, optionally in a pharmaceutically acceptable carrier.

The compounds of this invention either possess antiviral (i.e., anti-HIV) activity, or are metabolized to a compound that exhibits such activity.

In summary, the present invention includes the following features:

phenylindoles and their pharmaceutically acceptable salts and prodrugs thereof as described herein;

phenylindoles and their pharmaceutically acceptable salts and prodrugs thereof as described herein substantially free of other chemical entities;

phenylindoles and their pharmaceutically acceptable salts and prodrugs thereof as described herein that are effective against HIV in a host;

phenylindoles and their pharmaceutically acceptable salts and prodrugs thereof as described herein that are effective against drug-resistant strains of HIV in a host;

phenylindoles and their pharmaceutically acceptable salts and prodrugs thereof as described herein that are effective against drug-resistant strains of HIV due to a reverse transcriptase mutation, such as lysine 103→asparagine and/or tyrosine 181→cysteine;

phenylindoles and their pharmaceutically acceptable salts and prodrugs thereof as described herein for use in the treatment or prophylaxis of an HIV infection in a host, especially in individuals diagnosed as having an HIV infection or being at risk for becoming infected by HIV;

phenylindoles and their pharmaceutically acceptable salts and prodrugs thereof as described herein for use in the manufacture of a medicament for the treatment or prophylaxis of an HIV infection in a host, especially in individuals diagnosed as having an HIV infection or being at risk for becoming infected by HIV;

phenylindoles and their pharmaceutically acceptable salts and prodrugs thereof as described herein for use in the treatment or prophylaxis of an HIV infection, which is resistant to one or more reverse transcriptase inhibitors, in a host;

phenylindoles and their pharmaceutically acceptable salts and prodrugs thereof as described herein for use in the manufacture of a medicament for the treatment or prophylaxis of an HIV infection, which is resistant to one or more reverse transcriptase inhibitors, in a host;

phenylindoles and their pharmaceutically acceptable salts and prodrugs thereof as described herein for use in the treatment or prophylaxis of an HIV infection as a form of salvage therapy in a host, especially in individuals diagnosed as having an HIV infection or being at risk for becoming infected by HIV;

phenylindoles and their pharmaceutically acceptable salts and prodrugs thereof as described herein for use in the manufacture of a medicament for the treatment or prophylaxis of an HIV infection as a form of salvage therapy in a host, especially in individuals diagnosed as having an HIV infection or being at risk for becoming infected by HIV;

phenylindoles and their pharmaceutically acceptable salts and prodrugs thereof as described herein for use in the treatment or prophylaxis of an HIV infection that is resistant to one or more reverse transcriptase inhibitors due to a reverse transcriptase mutation, such as lysine 103→asparagine and/or tyrosine 181→cysteine, in a host, especially in individuals diagnosed as having an HIV infection or being at risk for becoming infected by HIV;

phenylindoles and their pharmaceutically acceptable salts and prodrugs thereof as described herein for use in the manufacture of a medicament for the treatment or prophylaxis of an HIV infection that is resistant to one or more reverse transcriptase inhibitors due to a reverse transcriptase mutation, such as lysine 103→asparagine and/or tyrosine 181→cysteine, in a host, especially in individuals diagnosed as having an HIV infection or being at risk for becoming infected by HIV;

processes for the preparation of phenylindoles, as described in more detail below;

processes for the preparation of phenylindoles substantially isolated from other chemical entities;

pharmaceutical compositions comprising an effective anti-HIV treatment amount of a phenylindole or its pharmaceutically acceptable salt or prodrug thereof together with a pharmaceutically acceptable carrier or diluent;

pharmaceutical compositions comprising an effective anti-HIV treatment amount of a phenylindole or its pharmaceutically acceptable salt or prodrug thereof in combination with one or more other anti-HIV agent, optionally with a pharmaceutically acceptable carrier or diluent;

pharmaceutical compositions for the treatment or prophylaxis of an HIV infection in a host comprising an effective anti-HIV treatment amount of a phenylindole or its pharmaceutically acceptable salt or prodrug thereof, optionally in combination with one or more other anti-HIV agent, optionally with a pharmaceutically acceptable carrier or diluent;

pharmaceutical compositions for the treatment or prophylaxis of an HIV infection, which is resistant to one or more reverse transcriptase inhibitors, in a host comprising an effective anti-HIV treatment amount of a phenylindole or its pharmaceutically acceptable salt or prodrug thereof, optionally in combination with one or more other anti-HIV agent, optionally with a pharmaceutically acceptable carrier or diluent;

pharmaceutical compositions for the treatment or prophylaxis of an HIV infection in a host as a form of salvage therapy comprising an effective anti-HIV treatment amount of a phenylindole or its pharmaceutically acceptable salt or prodrug thereof, optionally in combination with one or more other anti-HIV agent, optionally with a pharmaceutically acceptable carrier or diluent;

pharmaceutical compositions for the treatment or prophylaxis of an HIV infection, which is resistant to one or more reverse transcriptase inhibitors due to a reverse transcriptase mutation, such as lysine 103→asparagine and/or tyrosine 181→cysteine, in a host comprising an effective anti-HIV treatment amount of a phenylindole or its pharmaceutically acceptable salt or prodrug thereof, optionally in combination with one or more other anti-HIV agent, optionally with a pharmaceutically acceptable carrier or diluent;

methods for the treatment or prophylaxis of an HIV infection in a host comprising administering to said host an effective anti-HIV treatment amount of a phenylindole or its pharmaceutically acceptable salt or prodrug thereof, optionally in combination and/or alternation with one or more other anti-HIV agent, optionally with a pharmaceutically acceptable carrier or diluent;

methods for the treatment or prophylaxis of an HIV infection, which is resistant to one or more reverse transcriptase inhibitors, in a host comprising administering to said host an effective anti-HIV treatment amount of a phenylindole or its pharmaceutically acceptable salt or prodrug thereof, optionally in combination and/or alternation with one or more other anti-HIV agent, optionally with a pharmaceutically acceptable carrier or diluent;

methods for the treatment or prophylaxis of an HIV infection in a host as a form of salvage therapy comprising administering to said host an effective anti-HIV treatment amount of a phenylindole or its pharmaceutically acceptable salt or prodrug thereof, optionally in combination and/or alternation with one or more other anti-HIV agent, optionally with a pharmaceutically acceptable carrier or diluent;

methods for the treatment or prophylaxis of an HIV infection, which is resistant to one or more reverse transcriptase inhibitors due to a reverse transcriptase mutation, such as lysine 103→asparagine and/or tyrosine 181→cysteine, in a host comprising administering to said host an effective anti-HIV treatment amount of a phenylindole or its pharmaceutically acceptable salt or prodrug thereof, optionally in combination and/or alternation with one or more other anti-HIV agent, optionally with a pharmaceutically acceptable carrier or diluent;

use of a phenylindole or its pharmaceutically acceptable salt or prodrug thereof, optionally in combination and/or alternation with one or more other anti-HIV agent, optionally with a pharmaceutically acceptable carrier or diluent for the treatment or prophylaxis of an HIV infection in a host;

use of a phenylindole or its pharmaceutically acceptable salt or prodrug thereof, optionally in combination and/or alternation with one or more other anti-HIV agent, optionally with a pharmaceutically acceptable carrier or diluent for the treatment or prophylaxis of an HIV infection, which is resistant to one or more reverse transcriptase inhibitors, in a host;

use of a phenylindole or its pharmaceutically acceptable salt or prodrug thereof, optionally in combination and/or alternation with one or more other anti-HIV agent, optionally with a pharmaceutically acceptable carrier or diluent for the treatment or prophylaxis of an HIV infection in a host as a form of salvage therapy;

use of a phenylindole or its pharmaceutically acceptable salt or prodrug thereof, optionally in combination and/or alternation with one or more other anti-HIV agent, optionally with a pharmaceutically acceptable carrier or diluent for the treatment or prophylaxis of an HIV infection, which is resistant to one or more reverse transcriptase inhibitors due to a reverse transcriptase mutation, such as lysine 103→asparagine and/or tyrosine 181→cysteine, in a host;

use of a phenylindole or its pharmaceutically acceptable salt or prodrug thereof, optionally in combination and/or alternation with one or more other anti-HIV agent, optionally with a pharmaceutically acceptable carrier or diluent in the manufacture of a medicament for the treatment or prophylaxis of an HIV infection in a host;

use of a phenylindole or its pharmaceutically acceptable salt or prodrug thereof, optionally in combination and/or alternation with one or more other anti-HIV agent, optionally with a pharmaceutically acceptable carrier or diluent in the manufacture of a medicament for the treatment or prophylaxis of an HIV infection, which is resistant to one or more reverse transcriptase inhibitors, in a host;

use of a phenylindole or its pharmaceutically acceptable salt or prodrug thereof, optionally in combination and/or alternation with one or more other anti-HIV agent, optionally with a pharmaceutically acceptable carrier or diluent in the manufacture of a medicament for the treatment or prophylaxis of an HIV infection in a host as a form of salvage therapy; and use of a phenylindole or its pharmaceutically acceptable salt or prodrug thereof, optionally in combination and/or alternation with one or more other anti-HIV agent, optionally with a pharmaceutically acceptable carrier or diluent in the manufacture of a medicament for the treatment or prophylaxis of an HIV infection, which is resistant to one or more reverse transcriptase inhibitors due to a reverse transcriptase mutation, such as lysine 103→asparagine and/or tyrosine 181→cysteine, in a host.

I. Active Compounds of the Present Invention

Suitable phenylindoles for practicing the present invention can be represented generally by formula (I):

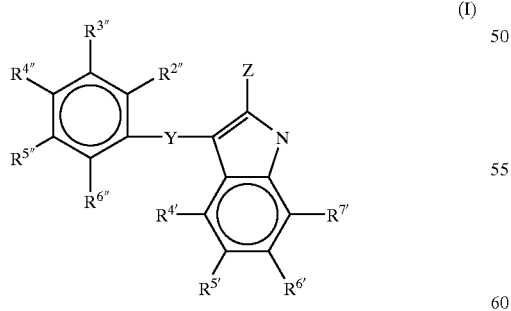

(I)

or its pharmaceutically acceptable salt or prodrug thereof, and are defined below.

In one embodiment of the present invention the compound of formula (I) is defined as follows:

(a) $R^1$ is hydrogen; acyl; —C(=O)H; —C(=W)H; —C(=O)$R^2$; —C(=W)$R^2$; —C(=O)OH; —C(=W)OH; —C(=O)O$R^2$; —C(=W)O$R^2$; —C(=O)SH; —C(=W)SH; —C(=O)S$R^2$; —C(=W)S$R^2$; —C(=O)NH$_2$; —C(=W)NH$_2$; —C(=O)NH$R^2$; —C(=W)NH$R^2$; —C(=O)N$R^2R^3$; —C(=W)N$R^2R^3$; —C(=W)NH—(CH$_2$)$_p$-(amino acid) or —(CH$_2$)$_p$-(amino acid);

(b) $R^{4'}$, $R^{5'}$, $R^{6'}$, $R^{7'}$, $R^{2''}$, $R^{3''}$, $R^{4''}$, $R^{5''}$ and $R^{6''}$ are each independently H; halo (F, Cl, Br or I); —NO$_2$; —CN; —OH; —O$R^2$; —SH; —S$R^2$; —NH$_2$; —NH$R^2$; —N$R^2R^3$; —NHSO$_2$—C$_{1-3}$alkyl; —N$R^2$SO$_2$—C$_{1-3}$alkyl; —NHCO—C$_{1-3}$alkyl; —N$R^2$CO—C$_{1-3}$alkyl; optionally substituted or unsubstituted branched or unbranched alkyl, alkenyl or alkynyl (such as an optionally substituted or unsubstituted branched or unbranched C$_{1-6}$alkyl, C$_{2-6}$alkenyl or C$_{2-6}$alkynyl, and in particular CH$_3$, CF$_3$, vinyl bromide, —CR$^2$R$^2$—S(O)$_n$—R$^3$, —CR$^2$R$^2$NH$_2$, —CR$^2$R$^2$NHR$^2$, —CR$^2$R$^2$NR$^2$R$^3$ and —CR$^2$R$^2$—C(=O)R$^2$); alkacyl; optionally substituted or unsubstituted acyl; —C(=O)H; —C(=W)H; —C(=O)R$^2$; —C(=W)R$^2$; —C(=O)OH; —C(=W)OH; —C(=O)OR$^2$; —C(=W)OR$^2$; —C(=O)—SH; —C(=W)SH; —C(=O)SR$^2$; —C(=W)SR$^2$; —C(=O)NH$_2$; —C(=W)NH$_2$; —C(=O)NHR$^2$; —C(=W)NHR$^2$; —C(=O)NR$^2$R$^3$; —C(=W)—NR$^2$R$^3$, —C(=W)NH(CH$_2$)$_p$-(amino acid), a residue of an amino acid or —(CH$_2$)$_p$(amino acid); wherein if $R^{5'}$ is hydrogen, F, Cl, Br, —NO$_2$, —CN, —OR$^2$, —NR$^2$R$^2$, —NHSO$_2$—C$_{1-3}$alkyl or —NHCO—C$_{1-3}$alkyl, then at least one of $R^{4'}$, $R^{6'}$ and $R^{7'}$ is not hydrogen;

(c) Z is optionally substituted or unsubstituted acyl, —C(=O)NH$_2$; —C(=W)—NH$_2$; —C(=O)NHR$^2$; —C(=W)NHR$^2$; —C(=O)NR$^2$R$^3$; —C(=W)NR$^2$R$^3$; —C(=W)NH(CH$_2$)$_p$-(amino acid); a residue of an amino acid, —(CH$_2$)$_p$-(amino acid); —C(=O)R$^3$; —C(=O)H; —C(=W)H; —C(=O)R$^2$; —C(=W)R$^2$; —C(=O)OR$^3$; —C(=O)OH; —C(=W)OH; —C(=O)OR$^2$; —C(=W)—OR$^2$; —C(=O)—SH; —C(=W)SH; —C(=O)SR$^2$; —C(=W)SR$^2$; optionally substituted or unsubstituted branched or unbranched alkyl, alkenyl or alkynyl (such as an optionally substituted or unsubstituted branched or unbranched C$_{1-6}$alkyl, C$_{2-6}$alkenyl or C$_{2-6}$alkynyl, and in particular CH$_3$, CF$_3$, vinyl bromide, —CR$^2$R$^2$—S(O)$_n$—R$^3$, —CR$^2$R$^2$NH$_2$, —CR$^2$R$^2$NHR$^2$, —CR$^2$R$^2$NR$^2$R$^3$ and —CR$^2$R$^2$—C(=O)R$^2$); —CN, or halo (F, Cl, Br or I);

(d) Y is O, S or S(O)$_n$;

(e) each W is independently O, S, —NH$_2$, —NHR$^2$, —NR$^2$R$^2$, —N—CN, —N—NH$_2$, —N—NHR$^2$, —N—NR$^2$R$^3$, —N—OH or —N—OR$^2$;

(f) each $R^2$ is independently hydrogen or an optionally substituted or unsubstituted branched or unbranched lower alkyl, alkenyl or alkynyl (such as an optionally substituted or unsubstituted branched or unbranched C$_{1-3}$alkyl, C$_{2-4}$alkenyl or C$_{2-4}$alkynyl, and in particular CH$_3$, CF$_3$, vinyl bromide, —CR$^2$R$^2$—S(O)$_n$—R$^3$, —CR$^2$R$^2$NH$_2$, —CR$^2$R$^2$NHR$^2$, —CR$^2$R$^2$NR$^2$R$^3$ and —CR$^2$R$^2$—C(=O)R$^2$);

(g) each $R^3$ is independently hydrogen; optionally substituted or unsubstituted branched or unbranched alkyl, alkenyl or alkynyl (such as an optionally substituted or unsubstituted branched or unbranched C$_{1-6}$alkyl, C$_{2-6}$alkenyl or C$_{2-6}$alkynyl, and in particular CH$_3$, CF$_3$, vinyl bromide, —CR$^2$R$^2$—S(O)$_n$—R$^3$, —CR$^2$R$^2$NH$_2$, —CR$^2$R$^2$NHR$^2$, —CR$^2$R$^2$NR$^2$R$^3$ and —CR$^2$R$^2$—C (=O)R$^2$); optionally substituted or unsubstituted aryl (such as phenyl); optionally substituted or unsubstituted heterocycle; optionally substituted or unsubstituted alkylaryl, optionally substituted or unsubstituted alkylhereterocycle, optionally substituted or unsubstituted aralkyl, optionally substituted or unsubstituted heterocycle-alkyl;

(h) each n is independently 0, 1 or 2; and (i) each p is independently 0, 1, 2, 3, 4 or 5;

(j) wherein if one or more of the optionally substituted branched or unbranched alkyl, alkenyl, alkynyl, lower alkyl, lower alkenyl or lower alkynyl; acyl; aryl; heterocycle; alkaryl; alkheterocycle; arylalkyl or alkylheterocycle substitutents is substituted, then preferably it is substituted with one or more of halogen (F, Cl, Br or I), —OH, —OR$^2$, —SH, —SR$^2$, oxime, hydrazine, —C(=O)H, —C(=W)H, —C(=O)R$^2$, —C(=W)R$^2$, —C(=O)OH, —C(=W)OH, —C(=O)OR$^2$, —C(=W)OR$^2$, —C(=O)SH, —C(=W)SH, —C(=O)SR$^2$, —C(=W)SR$^2$, —C(=O)NH$_2$, —C(=W)NH$_2$, —C(=O)—NHR$^2$, —C(=W)NHR$^2$, —C(=O)NR$^2$R$^3$, —C(=W)—NR$^2$R$^3$, —NH$_2$, —NHR$^2$, —NR$^2$R$^3$, —NHSO$_2$—C$_{1-3}$alkyl, —NR$^2$SO$_2$—C$_{1-3}$alkyl, —NHCO—C$_{1-3}$alkyl, —NR$^2$CO—C$_{1-3}$alkyl, —S(O)$_n$—R$^3$, C$_{1-3}$ alkoxy, C$_{1-3}$thioether, a residue of an amino acid such as —NH(CH$_2$)$_p$-(amino acid) or —C(=W)NH(CH$_2$)$_p$-(amino acid).

In a preferred embodiment, Y is SO$_2$. In another preferred embodiment, Z is an amide function.

In an alternative embodiment, the hydrogen attached to the indole nitrogen can be replaced with lower alkyl, for example, methyl, or aryl, alkaryl or aralkyl.

In another embodiment the invention provides a phenylindole represented generally by formula (I) above, wherein:

(a) R$^1$ is hydrogen;

(b) R$^{4'}$, R$^{5'}$, R$^{6'}$ and R$^{7'}$ are independently hydrogen, halogen (F, Cl, Br or I), —NO$_2$, —CN, —OR$^2$, —NR$^2$R$^2$, —NHSO$_2$—C$_{1-3}$alkyl, —NHCO—C$_{1-3}$ alkyl, oxime, hydrazine, or C$_{1-3}$ alkyl or alkenyl optionally substituted with one or more of —OH, —SH, —C(O)H, —COOH, halogen (F, Cl, Br or I), —NR$^2$R$^2$, —C$_{1-3}$ alkoxy or —C$_{1-3}$ thioether; wherein if R$^{5'}$ is hydrogen, F, Cl, Br, —NO$_2$, —CN, —OR$^2$, —NR$^2$R$^2$, —NHSO$_2$—C$_{1-3}$alkyl or —NHCO—C$_{1-3}$ alkyl, then at least one of R$^{4'}$, R$^{6'}$ and R$^{7'}$ is not hydrogen;

(c) R$^{2''}$, R$^{3''}$, R$^{4''}$, R$^{5''}$ and R$^{6''}$ are independently hydrogen, halogen (F, Cl, Br or I), —NO$_2$, —CN, —OH, —OR$^2$, —NR$^2$R$^2$, —NHSO$_2$—C$_{1-3}$alkyl, —NHCO—C$_{1-3}$ alkyl, —C$_{1-5}$ alkoxy, oxime, hydrazine, —C$_{1-5}$ alkyl or alkenyl optionally substituted with one or more of —OH, —SH, —C(O)H, —COOH, halogen (F, Cl, Br or I), —NR$^2$R$^2$, —C$_{1-5}$ thioether or —C$_{1-5}$ alkoxy;

(d) Z is —CN, —C(=W)NR$^2$R$^3$, —C(=O)R$^3$, —C(=O)OR$^3$, —CR$^2$R$^2$—S(O)$_n$—R$^3$, —CR$^2$R$^2$NHR$^2$, —CR$^2$R$^2$—CO—R$^3$ or substituted or unsubstituted lower alkyl;

(e) Y is O, S, or S(O)$_n$;

(f) each W is independently O, S, —N—CN or —N—OR$^2$;

(g) R$^2$ is hydrogen or C$_{1-3}$ alkyl;

(h) R$^3$ is hydrogen, substituted or unsubstituted alkyl, alkenyl, aryl, or heterocycle, —C$_{1-5}$ alkoxy, —OH, —NR$^2$R$^2$, or —(CH$_2$)$_p$C(O)NR$^2$R$^2$, (i) each n is independently 0, 1 or 2; and (j) each p is independently 0, 1, 2, 3, 4, or 5.

In still another embodiment the invention provides a phenylindole represented generally by formula (I) above, wherein:

(a) R$^1$ is hydrogen;

(b) R$^{4'}$, R$^{5'}$, R$^{6'}$, R$^{7'}$, are independently hydrogen, halogen (F, Cl, Br or I), —NO$_2$, —CN, —OR$^2$, —NR$^2$R$^2$, —NHSO$_2$—C$_{1-3}$alkyl, —NHCO—C$_{1-3}$alkyl, oxime, hydrazine, or C$_{1-3}$ alkyl or alkenyl optionally substituted with one or more of —OH, —SH, C(O)H, COOH, halogen, NR$^2$R$^2$, C$_{1-3}$ alkoxy, or C$_{1-3}$ thioether; wherein if R$^{5'}$ is hydrogen, F, Cl, Br, —NO$_2$, —CN, —OR$^2$, —NR$^2$R$^2$, —NHSO$_2$—C$_{1-3}$alkyl or —NHCO—C$_{1-3}$alkyl, then at least one of R$^{4'}$, R$^{6'}$ and R$^{7'}$ is not hydrogen;

(c) R$^{2''}$, R$^{3''}$, R$^{4''}$, R$^{5''}$, and R$^{6''}$, are independently hydrogen, halogen (F, Cl, Br or I), —NO$_2$, —CN, —OR$^2$, —NHSO$_2$—C$_{1-3}$alkyl, —NHCO—C$_{1-3}$alkyl, oxime, hydrazine, —C$_{1-5}$ alkyl or alkenyl optionally substituted with one or more of —OH, —SH, C(O)H, COOH, halogen, NR$^2$R$^2$, Cl$_5$ thioether, or C$_{1-5}$ alkoxy, —C$_{1-5}$ alkoxy, —OH, or —NR$^2$R$^2$, (d) Z is —C(W)NR$^2$R$^3$, or —COR$^3$, (e) Y is —S(O)$_n$— or —O—, in which n is 0, 1 or 2.

(f) W is O, S, —N—CN or —N—OR$^2$;

(g) R$^2$ is hydrogen or C$_{1-3}$ alkyl, (h) R$^3$ is C$_{1-5}$ alkyl, C$_{1-5}$ alkenyl, aryl, or heterocycle, substituted with one or more of C(O)NR$^2$R$^2$, —NR$^2$R$^2$, —(CH$_2$)$_m$C(O)NR$_2$R$^2$, —(CH$_2$)$_m$C(=W)—NH(CH$_2$)$_p$-(amino acid);

(k) each n is independently 0, 1 or 2; and (l) each p is independently 0, 1, 2, 3, 4, or 5.

In the first principal embodiment, the variables are defined as follows:

(a) Z is (i) —C(W)NR$^2$R$^3$, or (ii) —COR$^3$, (b) R$^2$ is hydrogen, or C$_{1-5}$ alkyl optionally substituted with —OH, or NR$^2$R$^2$, (c) R$^3$ is (i) —NR$^2$R$^2$, or (ii) —(CH$_2$)$_m$C(O)NR$^2$R$^2$, (iii) C$_{1-5}$ alkyl, C$_{1-5}$ alkenyl, aryl, or heterocycle, substituted with one or more of C(O)NR$^2$R$^2$, or (iv) a residue of an amino acid or —NH(CH$_2$)$_p$-(amino acid), (d) W is O, S, —N—CN, or —N—OR$^2$, (e) m is 1,2,3,4, or 5, (f) R$^{4'}$, R$^{5'}$, R$^{6'}$, R$^{7'}$, are independently (i) H, (ii) halo, (iii) —NO$_2$, (iv) —CN, (v) —OR$^2$, (vi) —NR$^2$R$^2$, (vii) —NHSO$_2$—C$_{1-3}$alkyl, (viii) —NHCO—C$_{1-3}$alkyl, (ix) oxime, (x) hydrazine, or (xi) C$_{1-3}$ alkyl or alkenyl optionally substituted with one or more of —OH, —SH, C(O)H, COOH, halogen, NR$^2$R$^2$, C$_{1-3}$ alkoxy, or C$_{1-3}$ thioether, (g) R$^{2''}$, R$^{3''}$, R$^{4''}$, R$^{1''}$, and R$^{6''}$, are independently (i) hydrogen, (ii) halogen, (iii) NO$_2$, (iv) —CN, (v) —OR$^2$, (vi) —NHSO$_2$—C$_{1-3}$alkyl, (vii) —NHCO—C$_{1-3}$alkyl, (viii) oxime, (ix) hydrazine, (x) —C$_{1-5}$ alkyl or alkenyl optionally substituted with one or more of —OH, —SH, C(O)H, COOH, halogen, NR$^2$R$^2$, C$_{1-5}$ thioether, or C$_{1-5}$ alkoxy, (xi) —C$_{1-5}$ alkoxy, (xii) —OH, or (ix) —NR$^2$R$^2$, and (h) Y is —S(O)$_n$— or —O—, in which n is 0, 1, or 2.

A first series of preferred subembodiments of the first principal embodiment are defined when Z is defined as follows:

1) Z is C(O)NR$^2$R$^3$, R$^2$ is hydrogen, and R$^3$ is NR$^2$R$^2$
2) Z is C(O)NR$^2$R$^3$, R$^2$ is hydrogen, and R$^3$ is NR$^2$R$^2$, and R$^2$ is C$_{1-5}$ alkyl optionally substituted with OH
3) Z is C(O)NR$^2$R$^3$, R$^2$ is hydrogen, and R$^3$ is (CH$_2$)$_m$C(O)NR$^2$R$^2$
4) Z is C(O)NR$^2$R$^3$, R$^2$ is hydrogen, and R$^3$ is alkyl substituted by substituted or unsubstituted aryl or heterocycle
5) Z is C(O)R$^3$, R$^3$ is a residue of an amino acid or —NH(CH$_2$)$_p$-(amino acid)
6) Z is —C(O)NHNHC$_2$H$_5$OH,
7) Z is —C(O)NHCH$_2$C(O)NH$_2$
8) Z is —C(O)NHCH$_2$CONHNH$_2$
9) Z is —C(O)NHCH$_2$CH$_2$-(2NO$_2$,5Me imidazole)
10) Z is —C(O)NHCH$_2$NHCH(CH$_3$)COOH
11) Z is —C(O)CH=CHC(O)NH$_2$ A second series of preferred subembodiments of the first principal embodiment are defined when R$^{4'}$, R$^{5'}$, R$^{6'}$, and R$^{7'}$ are defined as follows:

1) R$^{4'}$, R$^{6'}$, and R$^{7'}$ are hydrogen, and R$^{5'}$ is (i), halo, (ii) —NO$_2$, (iii) —CN, (iv) —OR$^2$, (v) —NR$^2$R$^2$, (vi) —NHSO$_2$—C$_{1-3}$alkyl, (vii) —NHCO—C$_{1-3}$alkyl, (viii) oxime, (ix) hydrazine, or (x) C$_{1-3}$ alkyl or alkenyl optionally substituted with one or more of —OH, —SH, C(O)H, COOH, halogen, NR$^2$R$^2$, C$_{1-3}$ alkoxy, or C$_{1-3}$ thioether,
2) R$^{6'}$ and R$^{7'}$ are hydrogen, and R$^{4'}$ and R$^{5'}$ are (i), halo, (ii) —NO$_2$, (iii) —CN, (iv) —OR$^2$, (v) —NR$^2$R$^2$, (vi) —NHSO$_2$—C$_{1-3}$alkyl, (vii) —NHCO—C$_{1-3}$alkyl, (viii) oxime, (ix) hydrazine, or (x) C$_{1-3}$ alkyl or alkenyl optionally substituted with one or more of —OH, —SH, C(O)H, COOH, halogen, NR$^2$R$^2$, C$_{1-3}$ alkoxy, or C$_{1-3}$ thioether,
3) R$^{4'}$ and R$^{7'}$ are hydrogen, and R$^{5'}$ and R$^{6'}$ are (i), halo, (ii) —NO$_2$, (iii) —CN, (iv) —OR$^2$, (v) —NR$^2$R$^2$, (vi) —NHSO$_2$—C$_{1-3}$alkyl, (vii) —NHCO—C$_{1-3}$alkyl, (viii) oxime, (ix) hydrazine, or (x) C$_{1-3}$ alkyl or alkenyl optionally substituted with one or more of —OH, —SH, C(O)H, COOH, halogen, NR$^2$R$^2$, C$_{1-3}$ alkoxy, or C$_{1-3}$ thioether,
4) R$^{4'}$ and R$^{6'}$ are hydrogen, and R$^{5'}$ and R$^{7'}$ are (i), halo, (ii) —NO$_2$, (iii) —CN, (iv) —OR$^2$, (v) —NR$^2$R$^2$, (vi) —NHSO$_2$—C$_{1-3}$alkyl, (vii) —NHCO—C$_{1-3}$alkyl, (viii) oxime, (ix) hydrazine, or (x) C$_{1-3}$ alkyl or alkenyl optionally substituted with one or more of —OH, —SH, C(O)H, COOH, halogen, NR$^2$R$^2$, C$_{1-3}$ alkoxy, or C$_{1-3}$ thioether,
5) R$^{6'}$ and R$^{7'}$ are hydrogen, and R$^{4'}$ and R$^{5'}$ are (i), halo, (ii) —NO$_2$, (iii) —CN, (iv) —OR$^2$, (v) —NR$^2$R$^2$, or (vi) C$_{1-3}$ alkyl or alkenyl optionally substituted with one or more of —OH, —SH, C(O)H, COOH, halogen, or NH$_2$,
6) R$^{4'}$ and R$^{7'}$ are hydrogen, and R$^{5'}$ and R$^{6'}$ are (i), halo, (ii) —NO$_2$, (iii) —CN, (iv) —OR$^2$, (v) —NR$^2$R$^2$, or (vi) C$_{1-3}$ alkyl or alkenyl optionally substituted with one or more of —OH, —SH, C(O)H, COOH, halogen, or NH$_2$,
7) R$^{4'}$ and R$^{6'}$ are hydrogen, and R$^{5'}$ and R$^{7'}$ are (i), halo, (ii) —NO$_2$, (iii) —CN, (iv) —OR$^2$, (v) —NR$^2$R$^2$, or (vi) C$_{1-3}$ alkyl or alkenyl optionally substituted with one or more of —OH, —SH, C(O)H, COOH, halogen, or NH$_2$,
8) R$^{6'}$ and R$^{7'}$ are hydrogen, and R$^{4'}$ and R$^{5'}$ are halo or C$_{1-3}$ alkyl or alkenyl substituted with one or more halo,
9) R$^{4'}$ and R$^{7'}$ are hydrogen, and R$^{5'}$ and R$^{6'}$ are halo or C$_{1-3}$ alkyl or alkenyl substituted with one or more halo,
10) R$^{4'}$ and R$^{6'}$ are hydrogen, and R$^{5'}$ and R$^{7'}$ are halo or C$_{1-3}$ alkyl or alkenyl substituted with one or more halo,
11) R$^{6'}$ and R$^{7'}$ are hydrogen, and R$^{4'}$ and R$^{5'}$ are Cl, F, CF$_3$, or vinyl bromide
12) R$^{4'}$ and R$^{7'}$ are hydrogen, and R$^{5'}$ and R$^{6'}$ are Cl, F, CF$_3$, or vinyl bromide
13) R$^{4'}$ and R$^{6'}$ are hydrogen, and R$^{5'}$ and R$^{7'}$ are Cl, F, CF$_3$, or vinyl bromide
14) R$^{4'}$, R$^{6'}$ and R$^{7'}$ are hydrogen, and R$^{5'}$ is (i) oxime, (ii) hydrazine, or (iii) C$_{1-3}$ alkyl or alkenyl optionally substituted with one or more of —OH, —SH, C(O)H, COOH, halogen, NR$^2$R$^2$, C$_{1-3}$ alkoxy, or C$_{1-3}$ thioether
15) R$^{4'}$, R$^{6'}$, and R$^{7'}$ are hydrogen, and R$^{5'}$ is Cl
16) R$^{4'}$ and R$^{7'}$ are hydrogen, and R$^{5'}$ and R$^{6'}$ are Cl
17) R$^{4'}$ and R$^{6'}$ are hydrogen, and R$^{5'}$ and R$^{7'}$ are F
18) R$^{6'}$ and R$^{7'}$ are hydrogen, and R$^{4'}$ and R$^{5'}$ are F
19) R$^{4'}$ and R$^{7'}$ are hydrogen, and R$^{5'}$ and R$^{6'}$ are F
20) R$^{4'}$ and R$^{6'}$ are hydrogen, and R$^{5'}$ and R$^{7'}$ are F
21) R$^{4'}$ and R$^{7'}$ are hydrogen, and R$^{5'}$ is Cl, and R$^{6'}$ is F
22) R$^{4'}$ and R$^{7'}$ are hydrogen, and R$^{5'}$ is Cl, and R$^{6'}$ is CF$_3$
23) R$^{4'}$, R$^{6'}$, and R$^{7'}$ are hydrogen, and R$^{5'}$ is CF$_3$
24) R$^{4'}$, R$^{6'}$, and R$^{7'}$ are hydrogen, and R$^{5'}$ is vinyl bromide A third series of preferred subembodiments of the first principal embodiment are defined when R$^{2''}$, R$^{3''}$, R$^{4''}$, R$^{5''}$, and R$^{6''}$, are defined as follows:

1) R$^{2''}$, R$^{4''}$, and R$^{6''}$, are hydrogen, and R$^{3''}$ and R$^{5''}$ are independently (i) halogen, (ii) NO$_2$, (iii) —CN, (iv) —OR$^2$, (v) —NHSO$_2$—C$_{1-3}$alkyl, (vi) —NHCO—C$_{1-3}$ alkyl, (vii) oxime, (vii) hydrazine, (viii) —C$_{1-5}$ alkyl or alkenyl optionally substituted with one or more of —OH, —SH, C(O)H, COOH, halogen, NR$^2$R$^2$, C$_{1-5}$ thioether, or C$_{1-5}$ alkoxy, (ix) —C$_{1-5}$ alkoxy, (x) —OH, or (xi) —NR$^2$R$^2$
2) R$^{2''}$, R$^{4''}$, and R$^{6''}$, are hydrogen, and R$^{3''}$ and R$^{5''}$ are independently (i) halogen, (ii) NO$_2$, (iii) —CN, (iv) —OR$^2$, (v) —C$_{1-5}$ alkyl or alkenyl optionally substituted with one or more of —OH, —SH, COOH, halogen, NR$^2$R$^2$, C$_{1-5}$ thioether, or C$_{1-5}$ alkoxy, (vi) —C$_{1-5}$ alkoxy, (vii) —OH, or (viii) —NR$^2$R$^2$
3) R$^{2''}$, R$^{4''}$, and R$^{6''}$, are hydrogen, and R$^{3''}$ and R$^{5''}$ are independently (i) halogen, (ii) NO$_2$, (iii) —CN, (iv) —OR$^2$, (v) —C$_{1-3}$ alkyl or alkenyl optionally substituted with one or more of —OH, —SH, COOH, halogen, or NH$_2$, (vi) —C$_{1-3}$ alkoxy, (vii) —OH, or (viii) —NR$^2$R$^2$
4) R$^{2''}$, R$^{4''}$, and R$^{6''}$, are hydrogen, and R$^{3''}$ and R$^{5''}$ are independently (i) halogen, or (ii) —C$_{1-3}$ alkyl or alkenyl optionally substituted with one or more halogen
5) R$^{2''}$, R$^{3''}$, R$^{4''}$, R$^{5''}$, and R$^{6''}$, are H
6) R$^{2''}$, R$^{4''}$, and R$^{6''}$, are H, and R$^{3''}$ and R$^{5'}$ are methyl
7) R$^{2''}$, R$^{4''}$, and R$^{6''}$, are H, and R$^{3''}$ and R$^{5''}$ are Cl
8) R$^{2''}$, R$^{4''}$, and R$^{6''}$, are H, and R$^{3''}$ and R$^{5''}$ are F
9) R$^{2''}$, R$^{4''}$, and R$^{6''}$, are H, and R$^{3''}$ and R$^{5''}$ are CF$_3$ A fourth series of preferred subembodiments are defined when Z is as defined in any one of the first series of preferred subembodiments of the first principal embodiment, R$^{4'}$, R$^{5'}$, R$^{6'}$, and R$^{7'}$ are as defined in any one of the second series of preferred subembodiments of the first principal embodiment, and R$^{2''}$, R$^{3''}$, R$^{4''}$, R$^{5''}$, and R$^{6''}$, are as defined in the first principal embodiment.

A fifth series of preferred subembodiments are defined when Z is as defined in any one of the first series of preferred subembodiments of the first principal embodiment, R$^{4'}$, R$^{5'}$, R$^{6'}$, and R$^{7'}$ are as defined in the first principal embodiment, and R$^{2''}$, R$^{3''}$, R$^{4''}$, R$^{5''}$, and R$^{6''}$, are as defined in any one of the third series of preferred subembodiment of the first principal embodiment.

A sixth series of preferred subembodiments are defined when Z is as defined in the first principal embodiment, R$^{4'}$, R$^{5'}$, R$^{6'}$, and R$^{7'}$ are as defined in any one of the second series of preferred subembodiments of the first principal embodiment, and $R^{2''}$, $R^{3''}$, $R^{4''}$, $R^{5''}$, and $R^{6''}$, are as defined in any one of the third series of preferred subembodiments of the first principal embodiment.

A seventh series of preferred subembodiments are defined when Z is as defined in any one of the first series of preferred subembodiments of the first principal embodiment, $R^{4'}$, $R^{5'}$, $R^{6'}$, and $R^{7'}$ are as defined in any one of the second series of preferred subembodiments of the first principal embodiment, and $R^{2''}$, $R^{3''}$, $R^{4''}$, $R^{5''}$, and $R^{6''}$, are as defined in any one of the third series of preferred subembodiments of the first principal embodiment.

In each of the subembodiments within the first, second, third, fourth, fifth, sixth, and seventh preferred series of subembodiments of the first principal embodiment, Y is preferably $SO_2$.

Preferred species of the first principal embodiment are defined when:

1) Z is —$C(O)NHNHC_2H_5OH$, $R^{4'}$, $R^{6'}$, and $R^{7'}$ are hydrogen, $R^{5'}$ is Cl, $R^{2''}$, $R^{4''}$, and $R^{6''}$, are H, $R^{3''}$ and $R^{5''}$ are methyl, and Y is $SO_2$;
2) Z is —$C(O)NHCH_2C(O)NH_2$, $R^{4'}$, $R^{6'}$, and $R^{7'}$ are hydrogen, $R^{5'}$ is Cl, $R^{2''}$, $R^{4''}$, and $R^{6''}$, are H, $R^{3''}$ and $R^{5''}$ are methyl, and Y is $SO_2$;
3) Z is —$C(O)NHCH_2CONHNH_2$, $R^{4'}$, $R^{6'}$, and $R^{7'}$ are hydrogen, $R^{5'}$ is Cl, $R^{2''}$, $R^{4''}$, and $R^{6''}$, are H, $R^{3''}$ and $R^{5''}$ are methyl, and Y is $SO_2$;
4) Z is —$C(O)NHCH_2CH_2$-($2NO_2$,5Me imidazole), $R^{4'}$, $R^{6'}$, and $R^{7'}$ are hydrogen, $R^{5'}$ is Cl, and $R^{6''}$, are H, $R^{3''}$ and $R^{5''}$ are methyl, and Y is $SO_2$;
5) Z is —$C(O)NHCH_2NHCH(CH_3)COOH$, $R^{4'}$, $R^{6'}$, and $R^{7'}$ are hydrogen, $R^{5'}$ is Cl, $R^{2''}$, $R^{4''}$, and $R^{6''}$, are H, $R^{3''}$ and $R^{5'}$ are methyl, and Y is $SO_2$; and
6) Z is —$C(O)CH=CHC(O)NH_2$, $R^{4'}$, $R^{6'}$, and $R^{7'}$ are hydrogen, $R^{5'}$ is $C^1$, $R^{2''}$, $R^{4''}$, and $R^{6''}$, are H, $R^{3''}$ and $R^{5''}$ are methyl, and Y is $SO_2$.

In a second principal the compound of formula (I) is defined as follows:

(a) either (a1) $R^{4'}$, $R^{5'}$, $R^{6'}$, $R^{7'}$, are independently (i) H, (ii), halo, (iii) —$NO_2$, (iv) —CN, (v) —$OR^2$, (vi) —$NR^2R^2$, (vii) —$NHSO_2$—$C_{1-3}$alkyl, (viii) —NHCO—$C_{1-3}$alkyl, (ix) oxime, (x) hydrazine, or (xi) $C_{1-3}$ alkyl or alkenyl optionally substituted with one or more of —OH, —SH, C(O)H, COOH, halogen, $NR^2R^2$, $C_{1-3}$ alkoxy, or $C_{1-3}$ thioether, wherein at least 2 of $R^{4'}$, $R^{5'}$, $R^{6'}$, and $R^{7'}$, are not hydrogen, or (a2) $R^{4'}$, $R^{5'}$, $R^{6'}$, $R^{7'}$, are independently (i) H, (ii), halo, (iii) —$NO_2$, (iv) —CN, (v) —$OR^2$, (vi) —$NR^2R^2$, (vii) —$NHSO_2$—$C_1—_3$alkyl, (viii) —NHCO—$C_{1-3}$alkyl, (ix) oxime, (x) hydrazine, or (xi) $C_{1-3}$ alkyl or alkenyl optionally substituted with one or more of —OH, —SH, C(O)H, COOH, halogen, $NR^2R^2$, $C_{1-3}$ alkoxy, or $C_{1-3}$ thioether, wherein at least one of $R^{4'}$, $R^{5'}$, $R^{6'}$, and $R^{7'}$, is not hydrogen, halogen, —$NHSO_2$—$C_{1-3}$alkyl, or $OR^2$, (b) Z is (i) $C(W)NR^2R^3$, (ii) —$COR^3$, (iii) —$COOR^3$, (iv) —$CR^2R^2$—$S(O)_n$—$R^3$, (v) —$CR^2R^2NHR^2$, (vi) —$CR^2R^2$—CO—$R^3$, (vii) substituted or unsubstituted lower alkyl, or (viii) —CN;

(c) $R^2$ is hydrogen, or $C_{1-5}$ alkyl optionally substituted with —OH, or $NR^2R^2$, (d) $R^3$ is (i) substituted or unsubstituted alkyl, alkenyl, aryl, or heterocycle, (ii) —$C_{1-5}$ alkoxy, (iii) —OH, (iv) hydrogen, (v) —$NR^2R^2$, (vi) —$(CH_2)_mC(O)$—$NR^2R^2$, or (vii) a residue of an amino acid or —$NH(CH_2)_p$-(amino acid);

(e) W is O, S, —N—CN, or —N—$OR^2$;
(f) m is 1,2,3,4, or 5;
(g) p is 0, 1,2,3,4, or 5,and
(h) $R^{2''}$, $R^{3''}$, $R^{4''}$, $R^{5''}$, and $R^{6''}$, are independently (i) hydrogen, (ii) halogen, (iii) $NO_2$, (iv) —CN, (v) —$OR^2$, (vi) —$NHSO_2$—$C_{1-3}$alkyl, (vii) —NHCO—$C_{1-3}$alkyl, (viii) oxime, (ix) hydrazine, (x) —$C_{1-5}$ alkyl or alkenyl optionally substituted with one or more of —OH, —SH, C(O)H, COOH, halogen, $NR^2R^2$, $C_{1-5}$ thioether, or $C_{1-5}$ alkoxy, (xi) —$C_{1-5}$ alkoxy, (xii) —OH, or (ix) —$NR^2R^2$.

In a first series of preferred subembodiments of the second principal embodiment, Z is defined as follows:

1) Z is $C(W)NR^2R^3$
2) Z is $C(O)NR^2R^3$
3) Z is $C(O)NR^2R^3$, and $R^2$ is hydrogen
4) Z is $C(O)NR^2R^3$, $R^2$ is hydrogen, and $R^3$ is $NR^2R^2$
5) Z is $C(O)NR^2R^3$, $R^2$ is hydrogen, and $R^3$ is $NR^2R^2$, and $R^2$ is $C_{1-5}$ alkyl optionally substituted with OH
6) Z is $C(O)NR^2R^3$, $R^2$ is hydrogen, and $R^3$ is $(CH_2)_mC(O)NR^2R^2$
7) Z is $C(O)NR^2R^3$, $R^2$ is hydrogen, and $R^3$ is substituted or unsubstituted alkyl
8) Z is $C(O)NR^2R^3$, $R^2$ is hydrogen, and $R^3$ is alkyl substituted by substituted or unsubstituted aryl or heterocycle
9) Z is $C(O)R^3$, $R^3$ is a residue of an amino acid or —$NH(CH_2)_p$-(amino acid)
10) Z is —$C(O)NH_2$.
11) Z is —$C(O)NHNHC_2H_5OH$
12) Z is —$C(O)NHCH_2C(O)NH_2$
13) Z is —$C(O)NHCH_2CONHNH_2$
14) Z is —$C(O)NHCH_2CH_2$-($2NO_2$,5Me imidazole)
15) Z is —$C(O)NHCH_2NHCH(CH_3)COOH$
16) Z is —$C(O)CH=CHC(O)NH_2$ A second series of preferred subembodiments of the second principal embodiment is defined when $R^{4'}$, $R^{5'}$, $R^{6'}$, $R^{7'}$, are defined as follows:

1) $R^{6'}$ and $R^{7'}$ are hydrogen, and $R^{4'}$ and $R^{5'}$ are (i), halo, (ii) —$NO_2$, (iii) —CN, (iv) —$OR^2$, (v) —$NR^2R^2$, (vi) —$NHSO_2$—$C_{1-3}$alkyl, (vii) —NHCO—$C_{1-3}$alkyl, (viii) oxime, (ix) hydrazine, or (x) $C_{1-3}$ alkyl or alkenyl optionally substituted with one or more of —OH, —SH, C(O)H, COOH, halogen, $NR^2R^2$, $C_{1-3}$ alkoxy, or $C_{1-3}$ thioether,
2) $R^{4'}$ and $R^{7'}$ are hydrogen, and $R^{5'}$ and $R^{6'}$ are (i), halo, (ii) —$NO_2$, (iii) —CN, (iv) —$OR^2$, (v) —$NR^2R^2$, (vi) —$NHSO_2$—$C_{1-3}$alkyl, (vii) —NHCO—$C_{1-3}$alkyl, (viii) oxime, (ix) hydrazine, or (x) $C_{1-3}$ alkyl or alkenyl optionally substituted with one or more of —OH, —SH, C(O)H, COOH, halogen, $NR^2R^2$, $C_{1-3}$ alkoxy, or $C_{1-3}$ thioether,
3) $R^{4'}$ and $R^{6'}$ are hydrogen, and $R^{5'}$ and $R^{7'}$ are (i), halo, (ii) —$NO_2$, (iii) —CN, (iv) —$OR^2$, (v) —$NR^2R^2$, (vi) —$NHSO_2$—$C_{1-3}$alkyl, (vii) —NHCO—$C_{1-3}$alkyl, (viii) oxime, (ix) hydrazine, or (x) $C_{1-3}$ alkyl or alkenyl optionally substituted with one or more of —OH, —SH, C(O)H, COOH, halogen, $NR^2R^2$, $C_{1-3}$ alkoxy, or $C_{1-3}$ thioether,
4) $R^{6'}$ and $R^{7'}$ are hydrogen, and $R^{4'}$ and $R^{5'}$ are (i), halo, (ii) —$NO_2$, (iii) —CN, (iv) —$OR^2$, (v) —$NR^2R^2$, or (vi) $C_{1-3}$ alkyl or alkenyl optionally substituted with one or more of —OH, —SH, C(O)H, COOH, halogen, or $NH_2$,
5) $R^{4'}$ and $R^{7'}$ are hydrogen, and $R^{5'}$ and $R^{6'}$ are (i), halo, (ii) —$NO_2$, (iii) —CN, (iv) —$OR^2$, (v) —$NR^2R^2$, or (vi) $C_{1-3}$ alkyl or alkenyl optionally substituted with one or more of —OH, —SH, C(O)H, COOH, halogen, or $NH_2$, 6) $R^{4'}$ and $R^{6'}$ are hydrogen, and $R^{5'}$ and $R^{7'}$ are (i), halo, (ii) —$NO_2$, (iii) —CN, (iv) —$OR^2$, (v) —$NR^2R^2$, or (vi) $C_{1-3}$ alkyl or alkenyl optionally substituted with one or more of —OH, —SH, C(O)H, COOH, halogen, or $NH_2$, 7) $R^{6'}$ and $R^{7'}$ are hydrogen, and $R^{4'}$ and $R^{5'}$ are halo or $C_{1-3}$ alkyl or alkenyl substituted with one or more halo, 8) $R^{4'}$ and $R^{7'}$ are hydrogen, and $R^{5'}$ and $R^{6'}$ are halo or $C_{1-3}$ alkyl or alkenyl substituted with one or more halo, 9) $R^{4'}$ and $R^{6'}$ are hydrogen, and $R^{5'}$ and $R^{7'}$ are halo or $C_{1-3}$ alkyl or alkenyl substituted with one or more halo, 10) $R^{6'}$ and $R^{7'}$ are hydrogen, and $R^{4'}$ and $R^{5'}$ are Cl, F, $CF_3$, or vinyl bromide, 11) $R^{4'}$ and $R^{7'}$ are hydrogen, and $R^{5'}$ and $R^{6'}$ are Cl, F, $CF_3$, or vinyl bromide, 12) $R^{4'}$ and $R^{6'}$ are hydrogen, and $R^{5'}$ and $R^{7'}$ are Cl, F, $CF_3$, or vinyl bromide, 13) $R^{4'}$, $R^{6'}$ and $R^{7'}$ are hydrogen, and $R^{5'}$ is (i) oxime, (ii) hydrazine, or (iii) $C_{1-3}$ alkyl or alkenyl optionally substituted with one or more of —OH, —SH, C(O)H, COOH, halogen, $NR^2R^2$, $C_{1-3}$ alkoxy, or $C_{1-3}$ thioether, 14) $R^{4'}$ and $R^{7'}$ are hydrogen, and $R^{5'}$ and $R^{6'}$ are Cl, 15) $R^{4'}$ and $R^{6'}$ are hydrogen, and $R^{5'}$ and $R^{7'}$ are Cl, 16) $R^{6'}$ and $R^{7'}$ are hydrogen, and $R^{4'}$ and $R^{5'}$ are F, 17) $R^{4'}$ and $R^{7'}$ are hydrogen, and $R^{5'}$ and $R^{6'}$ are F, 18) $R^{4'}$ and $R^{6'}$ are hydrogen, and $R^{5'}$ and $R^{7'}$ are F, 19) $R^{4'}$ and $R^{7'}$ are hydrogen, and $R^{5'}$ is Cl, and $R^{6'}$ is F, 20) $R^{4'}$ and $R^{7'}$ are hydrogen, and $R^{5'}$ is Cl, and $R^{6'}$ is $CF_3$, 21) $R^{4'}$, $R^{6'}$, and $R^{7'}$ are hydrogen, and $R^{5'}$ is $CF_3$, 22) $R^{4'}$, $R^{6'}$, and $R^{7'}$ are hydrogen, and $R^{5'}$ is vinyl bromide.

A third series of preferred subembodiments of the second principal embodiment are defined when $R^{2''}$, $R^{3''}$, $R^{4''}$, $R^{5''}$, and $R^{6''}$, are defined as follows:

1) $R^{2''}$, $R^{4''}$, and $R^{6''}$, are hydrogen, and $R^{3''}$ and $R^{5''}$ are independently (i) halogen, (ii) $NO_2$, (iii) —CN, (iv) —$OR^2$, (v) —$NHSO_2$—$C_{1-3}$alkyl, (vi) —NHCO—$C_{1-3}$alkyl, (vii) oxime, (vii) hydrazine, (viii) —$C_{1-5}$ alkyl or alkenyl optionally substituted with one or more of —OH, —SH, C(O)H, COOH, halogen, $NR^2R^2$, $C_{1-5}$ thioether, or $C_{1-5}$ alkoxy, (ix) —$C_{1-5}$ alkoxy, (x) —OH, or (xi) —$NR^2R^2$ 2) $R^{2''}$, $R^{4''}$, and $R^{6''}$, are hydrogen, and $R^{3''}$ and $R^{5''}$ are independently (i) halogen, (ii) $NO_2$, (iii) —CN, (iv) —$OR^2$, (v) —$C_{1-5}$ alkyl or alkenyl optionally substituted with one or more of —OH, —SH, COOH, halogen, $NR^2R^2$, $C_{1-5}$ thioether, or $C_{1-5}$ alkoxy, (vi) —$C_{1-5}$ alkoxy, (vii) —OH, or (viii) —$NR^2R^2$ 3) $R^{2''}$, $R^{4''}$, and $R^{6''}$, are hydrogen, and $R^{3''}$ and $R^{5''}$ are independently (i) halogen, (ii) $NO_2$, (iii) —CN, (iv) —$OR^2$, (v) —$C_{1-3}$ alkyl or alkenyl optionally substituted with one or more of —OH, —SH, COOH, halogen, or $NH_2$, (vi) —$C_{1-3}$ alkoxy, (vii) —OH, or (viii) —$NR^2R^2$ 4) $R^{2''}$, $R^{4''}$, and $R^{6''}$, are hydrogen, and $R^{3''}$ and $R^{5''}$ are independently (i) halogen, or (ii) —$C_{1-3}$ alkyl or alkenyl optionally substituted with one or more halogen 5) $R^{2''}$, $R^{3''}$, $R^{4''}$, $R^{5''}$, and $R^{6''}$, are H 6) $R^{2''}$, $R^{4''}$, and $R^{6''}$, are H, and $R^{3''}$ and $R^{5''}$ are methyl 7) $R^{2''}$, $R^{4''}$, and $R^{6''}$, are H, and $R^{3''}$ and $R^{5''}$ are Cl 8) $R^{2''}$, $R^{4''}$, and $R^{6''}$, are H, and $R^{3''}$ and R1" are F 9) $R^{2''}$, $R^{4''}$, and $R^{6''}$, are H, and $R^{3''}$ and $R^{5''}$ are $CF_3$ A fourth series of preferred subembodiments of the second principal embodiment are defined when Z is as defined in any one of the first series of preferred subembodiments of the second principal embodiment, $R^{4'}$, $R^{5'}$, $R^{6'}$, and $R^{7'}$ are as defined in any one of the second series of preferred subembodiments of the second principal embodiment, and $R^{2''}$, $R^{3''}$, $R^{4''}$, $R^{5''}$, and $R^{6''}$, are as defined in the second principal embodiment.

A fifth series of preferred subembodiments are defined when Z is as defined in any one of the first series of preferred subembodiments of the second principal embodiment, $R^{4'}$, $R^{5'}$, $R^{6'}$, and $R^{7'}$ are as defined in the second principal embodiment, and $R^{2''}$, $R^{3''}$, $R^{4''}$, $R^{5''}$, and $R^{6''}$, are as defined in any one of the third series of preferred subembodiment of the second principal embodiment.

A sixth series of preferred subembodiments are defined when Z is as defined in the second principal embodiment, $R^{4'}$, $R^{5'}$, $R^{6'}$, and $R^{7'}$ are as defined in any one of the second series of preferred subembodiments of the second principal embodiment, and $R^{2''}$, $R^{3''}$, $R^{4''}$, $R^{5''}$, and $R^{6''}$, are as defined in any one of the third series of preferred subembodiments of the second principal embodiment.

A seventh series of preferred subembodiments are defined when Z is as defined in any one of the first series of preferred subembodiments of the second principal embodiment, $R^{4'}$, $R^{5'}$, $R^{6'}$, and $R^{7'}$ are as defined in any one of the second series of preferred subembodiments of the second principal embodiment, and $R^{2''}$, $R^{3''}$, $R^{4''}$, $R^{5''}$, and $R^{6''}$, are as defined in any one of the third series of preferred subembodiments of the second principal embodiment.

In each of the subembodiments within the first, second, third, fourth, fifth, sixth, and seventh preferred series of subembodiments of the second principal embodiment, Y is preferably $SO_2$.

Preferred species of the second principal embodiment are defined when:

1) Z is —$C(O)NH_2$, $R^{4'}$ and $R^{7'}$ are hydrogen, $R^{5'}$ and $R^{6'}$ are Cl, $R^{2''}$, $R^{3''}$, $R^{4''}$, $R^{5''}$, and $R^{6''}$ are H, and Y is $SO_2$.

2) Z is —$C(O)NH_2$, $R^{4'}$ and $R^{7'}$ are hydrogen, $R^{5'}$ and $R^{6'}$ are Cl, $R^{2''}$, $R^{4''}$, and $R^{6''}$, are H, $R^{3''}$ and $R^{5''}$ are methyl, and Y is $SO_2$.

3) Z is —$C(O)NH_2$, $R^{4'}$ and $R^{6'}$ are hydrogen, $R^{5'}$ and $R^{7'}$ are Cl, $R^{2''}$, $R^{4''}$, and $R^{6''}$, are H, $R^{3''}$ and $R^{5''}$ are methyl, and Y is $SO_2$.

4) Z is —$C(O)NH_2$, $R^{6'}$ and $R^{7'}$ are hydrogen, $R^{4'}$ and $R^{5'}$ are F, $R^{2''}$, $R^{4''}$, and $R^{6''}$, are H, $R^{3''}$ and $R^{5''}$ are methyl, and Y is $SO_2$.

5) Z is —$C(O)NH_2$, $R^{4'}$ and $R^{7'}$ are hydrogen, $R^{5'}$ and $R^{6'}$ are F, $R^{2''}$, $R^{4''}$, and $R^{6''}$, are H, $R^{3''}$ and $R^{5''}$ are methyl, and Y is $SO_2$.

6) Z is —$C(O)NH_2$, $R^{4'}$ and $R^{6'}$ are hydrogen, $R^{5'}$ and $R^{7'}$ are F, $R^{2''}$, $R^{4''}$, and $R^{6''}$, are H, $R^{3''}$ and $R^{5''}$ are methyl, and Y is $SO_2$.

7) Z is —$C(O)NH_2$, $R^{4'}$ and $R^{7'}$ are hydrogen, $R^{5'}$ is Cl, and $R^{6'}$ is F, $R^{2''}$, $R^{4''}$, and $R^{6''}$, are H, $R^{3''}$ and $R^{5''}$ are methyl, and Y is $SO_2$.

8) Z is —$C(O)NH_2$, $R^{4'}$ and $R^{7'}$ are hydrogen, $R^{5'}$ is Cl, and $R^{6'}$ is $CF_3$, $R^{2''}$, $R^{4''}$, and $R^{6''}$, are H, $R^{3''}$ and $R^{5''}$ are methyl, and Y is $SO_2$.

9) Z is —$C(O)NH_2$, $R^{4'}$, $R^{6'}$, and $R^{7'}$ are hydrogen, $R^{5'}$ is $CF_3$, $R^{2''}$, $R^{4''}$, and $R^{6''}$, are H, $R^{3''}$ and $R^{5''}$ are methyl, and Y is $SO_2$.

10) Z is —$C(O)NH_2$, $R^{4'}$, $R^{6'}$, and $R^{7'}$ are hydrogen, $R^{5'}$ is vinyl bromide, $R^{2''}$, $R^{4''}$, and $R^{6''}$, are H, $R^{3''}$ and $R^{5''}$ are methyl, and Y is $SO_2$.

A third principal embodiment of the invention compound (I) is defined as follows:
(a) Z is (i) $C(W)NR^2R^3$, (ii) —$COR^3$, (iii) —$COOR^3$, (iv) —$CR^2R^2$—$S(O)_n$—$R^3$, (v) —$CR^2R^2NHR^2$, (vi) —$CR^2R^2$—CO—$R^3$, (vii) substituted or unsubstituted lower alkyl, or (viii) —CN;
(i) $R^2$ is hydrogen, or $C_{1-5}$ alkyl optionally substituted with —OH, or $NR^2R^2$, (b) $R^3$ is (i) substituted or unsubstituted alkyl, alkenyl, aryl, or heterocycle, (ii) —$C_{1-5}$ alkoxy, (iii) —OH, (iv) hydrogen, (v) —$NR^2R^2$, (vi) —$(CH_2)_mC(O)NR^2R^2$, or (vii) a residue of an amino acid or —$NH(CH_2)_p$-(amino acid);

(c) W is O, S, —N—CN, or —N—$OR^2$;

(d) m is 1, 2, 3, 4, or 5;

(e) p is 0, 1, 2, 3, 4, or 5;

(f) $R^{4'}$, $R^{5'}$, $R^{6'}$, $R^{7'}$, are independently (i) H, (ii) halo, (iii) —$NO_2$, (iv) —CN, (v) —$OR^2$, (vi) —$NR^2R^2$, (vii) —$NHSO_2$—$C_{1-3}$alkyl, (viii) —NHCO—$C_{1-3}$alkyl, (ix) oxime, (x) hydrazine, or (xi) $C_{1-3}$ alkyl or alkenyl optionally substituted with one or more of —OH, —SH, C(O)H, COOH, halogen, $NR^2R^2$, $C_{1-3}$ alkoxy, or $C_{1-3}$ thioether; and (g) $R^{2''}$, $R^{3''}$, $R^{4''}$, $R^{5''}$, and $R^{6''}$, are independently (i) hydrogen, (ii) halogen, (iii) $NO_2$, (iv) —CN, (v) —$OR^2$, (vi) —$NHSO_2$—$C_{1-3}$alkyl, (vii) —NHCO—$C_{1-3}$alkyl, (viii) oxime, (ix) hydrazine, (x) —$C_{1-5}$ alkyl or alkenyl optionally substituted with one or more of —OH, —SH, C(O)H, COOH, halogen, $NR^2R^2$, $C_{1-5}$ thioether, or $C_{1-5}$ alkoxy, (xi) —$C_{1-5}$ alkoxy, (xii) —OH, or (ix) —$NR^2R^2$, wherein (i) at least 2 of $R^{2''}$, $R^{3''}$, $R^{4''}$, $R^{5''}$, and $R^{6''}$ are not hydrogen, or (ii) at least 1 of $R^{2''}$, $R^{3''}$, $R^{4''}$, $R^{5''}$, and $R^{6''}$ is not hydrogen, halogen, or $OR^2$.

A first series of preferred subembodiments of the third principal embodiment are defined when Z is as follows:

1) Z is $C(W)NR^2R^3$
2) Z is $C(O)NR^2R^3$
3) Z is $C(O)NR^2R^3$, and $R^2$ is hydrogen
4) Z is $C(O)NR^2R^3$, $R^2$ is hydrogen, and $R^3$ is $NR^2R^2$
5) Z is $C(O)NR^2R^3$, $R^2$ is hydrogen, and $R^3$ is $NR^2R^2$, and $R^2$ is $C_{1-5}$ alkyl optionally substituted with OH
6) Z is $C(O)NR^2R^3$, $R^2$ is hydrogen, and $R^3$ is $(CH_2)_mC(O)NR^2R^2$
7) Z is $C(O)NR^2R^3$, $R^2$ is hydrogen, and $R^3$ is substituted or unsubstituted alkyl
8) Z is $C(O)NR^2R^3$, $R^2$ is hydrogen, and $R^3$ is alkyl substituted by substituted or unsubstituted aryl or heterocycle
9) Z is $C(O)R^3$, $R^3$ is a residue of an amino acid or —$NH(CH_2)_p$-(amino acid)
10) Z is —$C(O)NH_2$.
11) Z is —$C(O)NHNHC_2H_5OH$
12) Z is —$C(O)NHCH_2C(O)NH_2$
13) Z is —$C(O)NHCH_2CONHNH_2$
14) Z is —$C(O)NHCH_2CH_2$—(2NO$_2$, 5Me imidazole)
15) Z is —$C(O)NHCH_2NHCH(CH_3)COOH$
16) Z is —$C(O)CH=CHC(O)NH_2$ A second series of preferred embodiments of the second principal embodiment is defined when $R^{4'}$, $R^{5'}$, $R^{6'}$, and $R^{7'}$ are defined as follows:

1) $R^{4'}$, $R^{6'}$, and $R^{7'}$ are hydrogen, and $R^{5'}$ is (i), halo, (ii) —$NO_2$, (iii) —CN, (iv) —$OR^2$, (v) —$NR^2R^2$, (vi) —$NHSO_2$—$C_{1-3}$alkyl, (vii) —NHCO—$C_{1-3}$alkyl, (viii) oxime, (ix) hydrazine, or (x) $C_{1-3}$ alkyl or alkenyl optionally substituted with one or more of —OH, —SH, C(O)H, COOH, halogen, $NR^2R^2$, $C_{1-3}$ alkoxy, or $C_{1-3}$ thioether,
2) $R^{6'}$ and $R^{7'}$ are hydrogen, and $R^{4'}$ and $R^{5'}$ are (i), halo, (ii) —$NO_2$, (iii) —CN, (iv) —$OR^2$, (v) —$NR^2R^2$, (vi) —$NHSO_2$—$C_{1-3}$alkyl, (vii) —NHCO—$C_{1-3}$alkyl, (viii) oxime, (ix) hydrazine, or (x) $C_{1-3}$ alkyl or alkenyl optionally substituted with one or more of —OH, —SH, C(O)H, COOH, halogen, $NR^2R^2$, $C_{1-3}$ alkoxy, or $C_{1-3}$ thioether,
3) $R^{4'}$ and $R^{7'}$ are hydrogen, and $R^{5'}$ and $R^{6'}$ are (i), halo, (ii) —$NO_2$, (iii) —CN, (iv) —$OR^2$, (v) —$NR^2R^2$, (vi) —$NHSO_2$—$C_{1-3}$alkyl, (vii) —NHCO—$C_{1-3}$alkyl, (viii) oxime, (ix) hydrazine, or (x) $C_{1-3}$ alkyl or alkenyl optionally substituted with one or more of —OH, —SH, C(O)H, COOH, halogen, $NR^2R^2$, $C_{1-3}$ alkoxy, or $C_{1-3}$ thioether,
4) $R^{4'}$ and $R^{6'}$ are hydrogen, and $R^{5'}$ and $R^{7'}$ are (i), halo, (ii) —$NO_2$, (iii) —CN, (iv) —$OR^2$, (v) —$NR^2R^2$, (vi) —$NHSO_2$—$C_{1-3}$alkyl, (vii) —NHCO—$C_{1-3}$alkyl, (viii) oxime, (ix) hydrazine, or (x) $C_{1-3}$ alkyl or alkenyl optionally substituted with one or more of —OH, —SH, C(O)H, COOH, halogen, $NR^2R^2$, $C_{1-3}$alkoxy, or $C_{1-3}$ thioether,
5) $R^{6'}$ and $R^{7'}$ are hydrogen, and $R^{4'}$ and $R^{5'}$ are (i), halo, (ii) —$NO_2$, (iii) —CN, (iv) —$OR^2$, (v) —$NR^2R^2$, or (vi) $C_{1-3}$ alkyl or alkenyl optionally substituted with one or more of —OH, —SH, C(O)H, COOH, halogen, or $NH_2$,
6) $R^{4'}$ and $R^{7'}$ are hydrogen, and $R^{5'}$ and $R^{6'}$ are (i), halo, (ii) —$NO_2$, (iii) —CN, (iv $OR^2$, (v) —$NR^2R^2$, or (vi) $C_{1-3}$ alkyl or alkenyl optionally substituted with one or more of —OH, —SH, C(O)H, COOH, halogen, or $NH_2$,
7) $R^{4'}$ and $R^{6'}$ are hydrogen, and $R^{5'}$ and $R^{7'}$ are (i), halo, (ii) —$NO_2$, (iii) —CN, (iv) —$OR^2$, (v) —$NR^2R^2$, or (vi) $C_{1-3}$ alkyl or alkenyl optionally substituted with one or more of —OH, —SH, C(O)H, COOH, halogen, or $NH_2$,
8) $R^{6'}$ and $R^{7'}$ are hydrogen, and $R^{4'}$ and $R^{5'}$ are halo or $C_{1-3}$ alkyl or alkenyl substituted with one or more halo,
9) $R^{4'}$ and $R^{7'}$ are hydrogen, and $R^{5'}$ and $R^{6'}$ are halo or $C_{1-3}$ alkyl or alkenyl substituted with one or more halo,
10) $R^{4'}$ and $R^{6'}$ are hydrogen, and $R^{5'}$ and $R^{7'}$ are halo or $C_{1-3}$ alkyl or alkenyl substituted with one or more halo,
11) $R^{6'}$ and $R^{7'}$ are hydrogen, and $R^{4'}$ and $R^{5'}$ are Cl, F, $CF_3$, or vinyl bromide
12) $R^{4'}$ and $R^{7'}$ are hydrogen, and $R^{5'}$ and $R^{6'}$ are Cl, F, $CF_3$, or vinyl bromide
13) $R^{4'}$ and $R^{6'}$ are hydrogen, and $R^{5'}$ and $R^{7'}$ are Cl, F, $CF_3$, or vinyl bromide
14) $R^{4'}$, $R^{6'}$ and $R^{7'}$ are hydrogen, and $R^{5'}$ is (i) oxime, (ii) hydrazine, or (iii) $C_{1-3}$ alkyl or alkenyl optionally substituted with one or more of —OH, —SH, C(O)H, COOH, halogen, $NR^2R^2$, $C_{1-3}$ alkoxy, or $C_{1-3}$ thioether
15) $R^{4'}$, $R^{6'}$, and $R^{7'}$ are hydrogen, and $R^{5'}$ is Cl
16) $R^{4'}$ and $R^{7'}$ are hydrogen, and $R^{5'}$ and $R^{6'}$ are Cl
17) $R^{4'}$ and $R^{6'}$ are hydrogen, and $R^{5'}$ and $R^{7'}$ are Cl
18) $R^{6'}$ and $R^{7'}$ are hydrogen, and $R^{4'}$ and $R^{5'}$ are F
19) $R^{4'}$ and $R^{7'}$ are hydrogen, and $R^{5'}$ and $R^{6'}$ are F
20) $R^{4'}$ and $R^{6'}$ are hydrogen, and $R^{5'}$ and $R^{7'}$ are F
21) $R^{4'}$ and $R^{7'}$ are hydrogen, and $R^{5'}$ is Cl, and $R^{6'}$ is F
22) $R^{4'}$ and $R^{7'}$ are hydrogen, and $R^{5'}$ is Cl, and $R^{6'}$ is $CF_3$
23) $R^{4'}$, $R^{6'}$, and $R^{7'}$ are hydrogen, and $R^{5'}$ is $CF_3$
24) $R^{4'}$, $R^{6'}$, and $R^{7'}$ are hydrogen, and $R^{5'}$ is vinyl bromide A third series of preferred subembodiments of the third principal embodiment is defined when $R^{2''}$, $R^{3''}$, $R^{4''}$, $R^{5''}$, and $R^{6''}$ are defined as follows:

1) $R^{2''}$, $R^{4''}$, and $R^{6''}$, are hydrogen, and $R^{3''}$ and $R^{5''}$ are independently (i) halogen, (ii) $NO_2$, (iii) —CN, (iv) —$OR^2$, (v) —$NHSO_2$—$C_{1-3}$alkyl, (vi) —NHCO—$C_{1-3}$ alkyl, (vii) oxime, (viii) hydrazine, (viii) —$C_{1-5}$ alkyl or alkenyl optionally substituted with one or more of —OH, —SH, C(O)H, COOH, halogen, $NR^2R^2$, $C_{1-5}$ thioether, or $C_{1-5}$ alkoxy, (ix) —$C_{1-5}$ alkoxy, (x) —OH, or (xi) —$NR^2R^2$
2) $R^{2''}$, $R^{4''}$, and $R^{6''}$, are hydrogen, and $R^{3''}$ and $R^{5''}$ are independently (i) halogen, (ii) $NO_2$, (iii) —CN, (iv)

—OR$^2$, (v) —C$_{1-5}$ alkyl or alkenyl optionally substituted with one or more of —OH, —SH, COOH, halogen, NR$^2$R$^2$, C$_{1-5}$ thioether, or C$_{1-5}$ alkoxy, (vi) —C$_{1-5}$ alkoxy, (vii) —OH, or (viii) —NR$^2$R$^2$ 3) R$^{2''}$, R$^{4''}$, and R$^{6''}$, are hydrogen, and R$^{3''}$ and R$^{5''}$ are independently (i) halogen, (ii) NO$_2$, (iii) —CN, (iv) —OR$^2$, (v) —C$_{1-3}$ alkyl or alkenyl optionally substituted with one or more of —OH, —SH, COOH, halogen, or NH$_2$, (vi) —C$_{1-3}$ alkoxy, (vii) —OH, or (viii) —NR$^2$R$^2$ 4) R$^{2''}$, R$^{4''}$, and R$^{6''}$, are hydrogen, and R$^{3''}$ and R$^{5''}$ are independently (i) halogen, or (ii) —C$_{1-3}$ alkyl or alkenyl optionally substituted with one or more halogen 5) R$^{2''}$, R$^{4''}$, and R$^{6''}$, are H, and R$^{3''}$ and R$^{5''}$ are methyl 6) R$^{2''}$, R$^{4''}$, and R$^{6''}$, are H, and R$^{3''}$ and R$^{5''}$ are Cl 7) R$^{2''}$, R$^{4''}$, and R$^{6''}$, are H, and R$^{3''}$ and R$^{5''}$ are F 8) R$^{2''}$, R$^{4''}$, and R$^{6''}$, are H, and R$^{3''}$ and R$^{5''}$ are CF$_3$ A fourth series of preferred subembodiments of the third principal embodiment are defined when Z is as defined in any one of the first series of preferred subembodiments of the third principal embodiment, R$^{4'}$, R$^{5'}$, R$^{6'}$, and R$^{7'}$ are as defined in any one of the second series of preferred subembodiments of the third principal embodiment, and R$^{2''}$, R$^{3''}$, R$^{4''}$, R$^{5''}$, and R$^{6''}$, are as defined in the third principal embodiment.

A fifth series of preferred subembodiments are defined when Z is as defined in any one of the first series of preferred subembodiments of the third principal embodiment, R$^{4'}$, R$^{5'}$, R$^{6'}$, and R$^{7'}$ are as defined in the third principal embodiment, and R$^{2''}$, R$^{3''}$, R$^{4''}$, R$^{5''}$, and R$^{6''}$, are as defined in any one of the third series of preferred subembodiment of the third principal embodiment.

A sixth series of preferred subembodiments are defined when Z is as defined in the third principal embodiment, R$^{4'}$, R$^{5'}$, R$^{6'}$, and R$^{7'}$ are as defined in any one of the second series of preferred subembodiments of the third principal embodiment, and R$^{2''}$, R$^{3''}$, R$^{4''}$, R$^{5''}$, and R$^{6''}$, are as defined in any one of the third series of preferred subembodiments of the third principal embodiment.

A seventh series of preferred subembodiments are defined when Z is as defined in any one of the first series of preferred subembodiments of the third principal embodiment, R$^{4'}$, R$^{5'}$, R$^{6'}$, and R$^{7'}$ are as defined in any one of the second series of preferred subembodiments of the third principal embodiment, and R$^{2''}$, R$^{3''}$, R$^{4''}$, R$^{5''}$, and R$^{6''}$, are as defined in any one of the third series of preferred subembodiments of the third principal embodiment.

In each of the subembodiments within the first, second, third, fourth, fifth, sixth, and seventh preferred series of subembodiments of the third principal embodiment, Y is preferably SO$_2$.

Preferred species of the third principal embodiment are defined as follows:

1) Z is —C(O)NHNHC$_2$H$_5$OH, R$^{4'}$, R$^{6'}$, and R$^{7'}$ are hydrogen, R$^{5'}$ is Cl, R$^{2''}$, R$^{4''}$, and R$^{6''}$, are H, R$^{3''}$ and R$^{''}$ are methyl, and Y is SO$_2$;

2) Z is —C(O)NHCH$_2$C(O)NH$_2$, R$^{4'}$, R$^{6'}$, and R$^{7'}$ are hydrogen, R$^{5'}$ is Cl, R$^{2''}$, R$^{4''}$, and R$^{6''}$, are H, R$^{3''}$ and R$^{5''}$ are methyl, and Y is SO$_2$;

3) Z is —C(O)NHCH$_2$CONHNH$_2$, R$^{4'}$, R$^{6'}$, and R$^{7'}$ are hydrogen, R$^{5'}$ is Cl, R$^{2''}$, R$^{4''}$, and R$^{6''}$, are H, R$^{3''}$ and R$^{5''}$ are methyl, and Y is SO$_2$;

4) Z is —C(O)NHCH$_2$CH$_2$-(2NO$_2$, 5Me imidazole), R$^{4'}$, R$^{6'}$, and R$^{7'}$ are hydrogen, R$^{5'}$ is Cl, R$^{2''}$, R$^{4''}$, and R$^{6''}$, are H, R$^{3''}$ and R$^{5''}$ are methyl, and Y is SO$_2$;

5) Z is —C(O)NHCH$_2$NHCH(CH$_3$)COOH, R$^{4'}$, R$^{6'}$, and R$^{7'}$ are hydrogen, R$^{5'}$ is Cl, R$^{2''}$, R$^{4''}$, and R$^{6''}$, are H, R$^{3''}$ and R$^{5'}$ are methyl, and Y is SO$_2$; and 6) Z is —C(O)CH=CHC(O)NH$_2$, R$^{4'}$, R$^{6'}$, and R$^{7'}$ are hydrogen, R$^{5'}$ is Cl, R$^{2''}$, R$^{4''}$, and R$^{6''}$, are H, R$^{3''}$ and R$^{5''}$ are methyl, and Y is SO$_2$.

7) Z is —C(O)NH$_2$, R$^{4'}$ and R$^{7'}$ are hydrogen, R$^{5'}$ and R$^{6'}$ are Cl, R$^{2''}$, R$^{4''}$, and R$^{6''}$, are H, R$^{3''}$ and R$^{5''}$ are methyl, and Y is SO$_2$.

8) Z is —C(O)NH$_2$, R$^{4'}$ and R$^{6'}$ are hydrogen, R$^{5'}$ and R$^{7'}$ are Cl, R$^{2''}$, R$^{4''}$, and R$^{6''}$, are H, R$^{3''}$ and R$^{5''}$ are methyl, and Y is SO$_2$.

9) Z is —C(O)NH$_2$, R$^{6'}$ and R$^{7'}$ are hydrogen, R$^{4'}$ and R$^{5'}$ are F, R$^{2''}$, R$^{4''}$, and R$^{6''}$, are H, R$^{3''}$ and R$^5$ are methyl, and Y is SO$_2$.

10) Z is —C(O)NH$_2$, R$^{4'}$ and R$^{7'}$ are hydrogen, R$^{5'}$ and R$^{6'}$ are F, R$^{2''}$, R$^4$, and R$^{6''}$, are H, R$^{3''}$ and R$^{5''}$ are methyl, and Y is SO$_2$.

11) Z is —C(O)NH$_2$, R$^{4'}$ and R$^{6'}$ are hydrogen, R$^{5'}$ and R$^{7'}$ are F, R$^{2''}$, R$^{4''}$, and R$^{6''}$, are H, R$^{3''}$ and R$^{5''}$ are methyl, and Y is SO$_2$.

12) Z is —C(O)NH$_2$, R$^{4'}$ and R$^{7'}$ are hydrogen, R$^{5'}$ is Cl, and R$^{6'}$ is F, R$^{2''}$, R$^{4''}$, and R$^{6''}$, are H, R$^{3''}$ and R$^{5''}$ are methyl, and Y is SO$_2$.

13) Z is —C(O)NH$_2$, R$^{4'}$ and R$^{7'}$ are hydrogen, R$^{5'}$ is Cl, and R$^{6'}$ is CF$_3$, R$^{2''}$, R$^{4''}$, and R$^{6''}$, are H, R$^{3''}$ and R$^{5''}$ are methyl, and Y is SO$_2$.

14) Z is —C(O)NH$_2$, R$^{4'}$, R$^{6'}$, and R$^{7'}$ are hydrogen, R$^{5'}$ is CF$_3$, R$^{2''}$, R$^{4''}$, and R$^{6''}$, are H, R$^{3''}$ and R$^{5''}$ are methyl, and Y is SO$_2$.

15) Z is —C(O)NH$_2$, R$^{4'}$, R$^{6'}$, and R$^{7'}$ are hydrogen, R$^{5'}$ is vinyl bromide, R$^{2''}$, R$^{4''}$, and R$^{6''}$, are H, R$^{3''}$ and R$^{5''}$ are methyl, and Y is SO$_2$.

16) Z is —C(O)NH$_2$, R$^{4'}$, R$^{6'}$, and R$^{7'}$ are hydrogen, R$^{5'}$ is Cl, R$^{2''}$, R$^{4''}$, and R$^{6''}$, are H, R$^{3''}$ and R$^{5''}$ are CF$_3$, and Y is SO$_2$.

17) Z is —C(O)NH$_2$, R$^{4'}$, R$^{6'}$, and R$^{7'}$ are hydrogen, R$^{5'}$ is Cl, R$^{2''}$, R$^{4''}$, and R$^{6''}$, are H, R$^{3''}$ and R$^{5''}$ are F, and Y is SO$_2$.

18) Z is —C(O)NH$_2$, R$^{4'}$, R$^{6'}$, and R$^{7'}$ are hydrogen, R$^{5'}$ is Cl, R$^{2''}$, R$^{4''}$, and R$^{6''}$, are H, R$^{3''}$ and R$^{5''}$ are Cl, and Y is SO$_2$.

In a particular embodiment, the phenylindole is a compound of the structure:

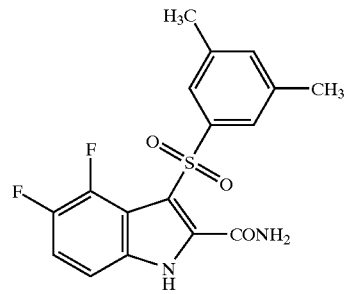

or a pharmaceutically acceptable salt or prodrug thereof.

In another particular embodiment, the phenylindole is a compound of the structure:

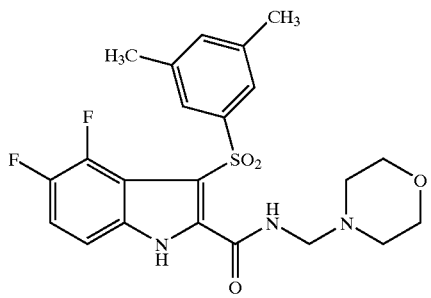

or a pharmaceutically acceptable salt or prodrug thereof.

In yet another particular embodiment, the phenylindole is a compound of the structure:

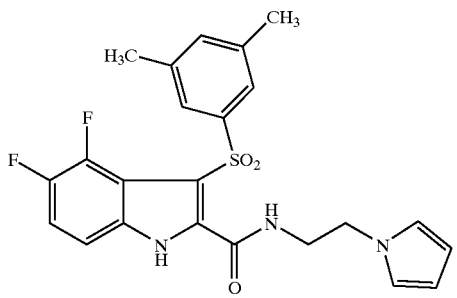

or a pharmaceutically acceptable salt or prodrug thereof.

In yet another particular embodiment, the phenylindole is a compound of the structure:

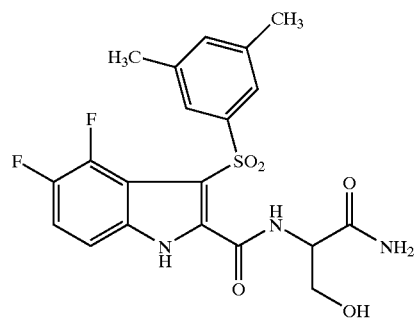

or a pharmaceutically acceptable salt or prodrug thereof.

In another particular embodiment, the phenylindole is a compound of the structure:

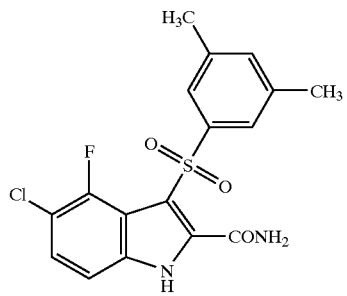

or a pharmaceutically acceptable salt or prodrug thereof.

In yet another particular embodiment of the present invention, the phenylindole is a compound of the structure:

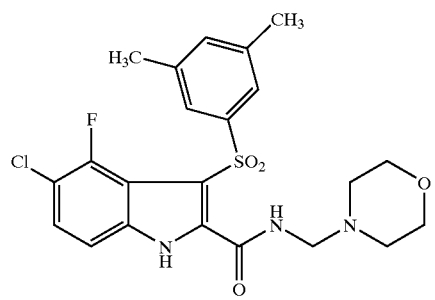

or a pharmaceutically acceptable salt or prodrug thereof.

In yet another particular embodiment of the present invention, the phenylindole is a compound of the structure:

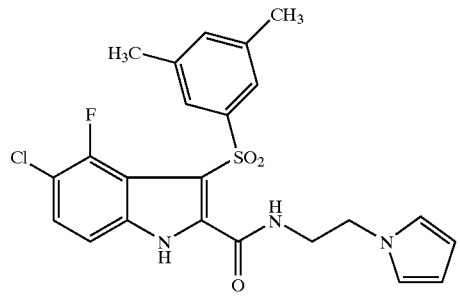

or a pharmaceutically acceptable salt or prodrug thereof.

In yet another particular embodiment of the present invention, the phenylindole is a compound of the structure:

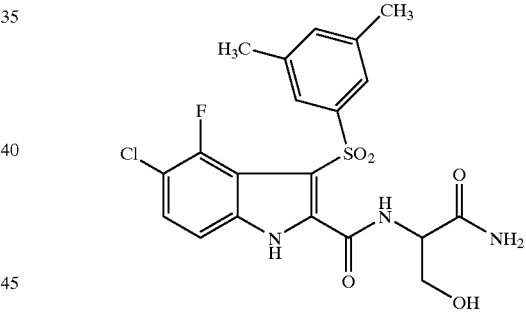

or a pharmaceutically acceptable salt or prodrug thereof.

The phenylindoles of this invention belong to a class of anti-HIV agents that inhibit HIV reverse transcriptase activity. Compounds can be screened for their ability to inhibit HIV reverse transcriptase activity in vitro according to screening methods set forth more particularly herein. One can readily determine the spectrum of activity by evaluating the compound in the assays described herein or with another confirmatory assay.

In one embodiment the efficacy of the anti-HIV compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or 10 micromolar.

The active compound can be administered as any salt or prodrug that upon administration to the recipient is capable of providing directly or indirectly the parent compound, or that exhibits activity itself. Nonlimiting examples are the pharmaceutically acceptable salts (alternatively referred to as "physiologically acceptable salts"). Further, the modifications can affect the biological activity of the compound, in some cases increasing the activity over the parent compound. This can easily be assessed by preparing the salt or prodrug and testing its antiviral activity according to the methods described herein, or other methods known to those skilled in the art.

II. Pharmaceutically Acceptable Salts and Prodrugs

The term "pharmaceutically acceptable salt or prodrug" is used throughout the specification to describe any pharmaceutically acceptable form (such as an ester, amide, salt of an ester, salt of an amide or a related group) of a compound that, upon administration to a patient, provides the active compound. As used herein, the term pharmaceutically acceptable salts refers to salts that retain the desired biological activity of the herein-identified compounds and exhibit minimal undesired toxicological effects. Pharmaceutically acceptable salts include those derived from pharmaceutically acceptable inorganic or organic acids and bases. Non-limiting examples of suitable salts include those derived from inorganic acids such as, hydrochloric acid, hydrobromic acid, sulfuric acid, phosphoric acid, nitric acid, bicarbonic acid, carbonic acid and the like, and salts formed with organic acids such as amino acid, acetic acid, oxalic acid, tartaric acid, succinic acid, malic acid, malonic acid, ascorbic acid, citric acid, benzoic acid, tannic acid, palmoic acid, alginic acid, polyglutamic acid, tosic acid, methanesulfonic acid, naphthalenesulfonic acid, naphthalenedisulfonic acid, α-ketoglutaric acid, α-glycerophosphoric acid and polygalacturonic acid. Suitable salts include those derived from alkali metals such as lithium, potassium and sodium, alkaline earth metals such as calcium and magnesium, among numerous other acids well known in the pharmaceutical art. Other suitable salts include those derived from other metal cations such as zinc, bismuth, barium, aluminum, copper, cobalt, nickel, cadmium, and the like, or with a cation formed from an amine, such as ammonia, N,N-dibenzylethylene-diamine, D-glucosamine, tetraethylammonium, or ethylenediamine. Further, suitable salts include those derived from a combinations of acids and bases, for example, a zinc tannate salt or the like.

Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention either possess antiviral activity against HIV, or are metabolized to a compound that exhibits such activity.

Any of the phenylindoles described herein can be administered as a prodrug to increase the activity, bioavailability, stability or otherwise alter the properties of the phenylindole. A number of prodrug ligands are known. In general, alkylation, acylation or other lipophilic modification of a heteroatom of the phenylindole will increase the stability of the compound. Examples of substituent groups that can replace one or more hydrogens on a heterocycle include, but are not limited to alkyl, aryl, steroids, carbohydrates, including sugars, 1,2-diacylglycerol, phospholipids, phosphotidylcholine, phosphocholine and alcohols. Any of these can be used in combination with the disclosed phenylindoles to achieve a desired effect.

III. Definitions

The following definitions and term construction are intended, unless otherwise indicated.

Specific and preferred values listed below for radicals, substituents and ranges, are for illustration only; they do not exclude other defined values or other values within defined ranges for the radicals and substituents.

Halo is fluoro, chloro, bromo, or iodo.

Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, cyclopropyl, butyl, isobutyl, $_t$-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. When the context of this document allows alkyl to be substituted, the moieties with which the alkyl group can be substituted are selected from the group consisting of hydroxyl, amino, alkylamino, arylamino, alkoxy, aryloxy, aryl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The terms alkenyl and alkynyl refer to alkyl moieties, including both substituted and substituted forms, wherein at least one saturated C—C bond is replaced by a double or triple bond. Thus, $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. Similarly, $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1- hexynyl, 2-hexynyl, 3-hexynyl, 4-hexynyl, or 5-hexynyl.

The term "alkylene" refers to a saturated, straight chain, divalent alkyl radical of the formula —$(CH_2)_n$—, wherein n can be 1, 2, 3, 4, 5, 6, 7, 8, 9, or 10.

As used herein, with exceptions as noted, "aryl" is intended to mean any stable monocyclic, bicyclic or tricyclic carbon ring of up to 8 members in each ring, wherein at least one ring is aromatic as defined by the Huckel 4n+2 rule. Examples of aryl ring systems include phenyl, naphthyl, tetrahydronaphthyl, and biphenyl. The aryl group can be substituted with one or more moieties selected from the group consisting of hydroxyl, amino, alkylamino, arylamino, alkoxy, aryloxy, alkyl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term heterocycle or heterocyclic, as used herein except where noted represents a stable 5- to 7-membered monocyclic or stable 8- to 11-membered bicyclic heterocyclic ring which is either saturated or unsaturated, including heteroaryl, and which consists of carbon atoms and from one to three heteroatoms selected from the group consisting of N, O, S, and P; and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, N6-alkylpurines, N6-benzylpurine, N6-halopurine, N6-vinypurine, N6-acetylenic purine, N6-acyl purine, N6-hydroxyalkyl purine, N6-thioalkyl purine, thymine, cytosine, 6-azapyrimidine, 2-mercaptopyrmidine, uracil, N5-alkylpyrimidines, N5-benzylpyrimidines, N5-halopyrimidines, N5-vinyl-pyrimidine, N5-acetylenic pyrimidine, N5-acyl pyrimidine, N5-hydroxyalkyl purine, and N6-thioalkyl purine, and isoxazolyl. The heteroaromatic and heterocyclic moieties can be optionally substituted as described above for aryl, including substituted with one or more substituents selected from hydroxyl, amino, alkylamino, arylamino, alkoxy, aryloxy, alkyl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The heteroaromatic can be partially or totally hydrogenated as desired. As a nonlimiting example, dihydropyridine can be used in place of pyridine. Functional oxygen and nitrogen groups on the heteroaryl group can be protected as necessary or desired. Suitable protecting groups are well known to those skilled in the art, and include trimethylsilyl, dimethylhexylsilyl, $_t$-butyldi-methylsilyl, and $_t$-butyldiphenylsilyl, trityl or substituted trityl, alkyl groups, acyl groups such as acetyl and propionyl, methanesulfonyl, and p-toluenesulfonyl.

The term acyl refers to a compound of formula RC(O)—, wherein R is substituted or unsubstituted alkyl or aryl, as defined herein. The term carboxyl refers to a compound of the formula —C(O)OR, wherein R is substituted or unsubstituted alkyl or aryl, as defined herein.

The term aralkyl, as used herein, and unless otherwise specified, refers to an aryl group as defined above linked to the molecule through an alkyl group as defined above. The term alkaryl, as used herein, and unless otherwise specified, refers to an alkyl group as defined above linked to the molecule through an aryl group as defined above.

The term alkoxy, as used herein, and unless otherwise specified, refers to a moiety of the structure —O-alkyl, wherein alkyl is as defined above.

The term amino, as used herein, refers to a moiety represented by the structure —$NR_2$, and includes primary amines, and secondary, and tertiary amines substituted by alkyl, aryl, heterocycle, acyl, and sulfinylalkyl. Thus, $R_2$ may represent two hydrogens, two alkyl moieties, or one hydrogen and one alkyl moiety.

The term amido, as used herein, refers to a moiety represented by the structure —$C(O)NR_2$, wherein $R_2$ is as defined for amino.

As used herein, an "amino acid" is a natural amino acid residue (e.g. Ala, Arg, Asn, Asp, Cys, Glu, Gln, Gly, His, Hyl, Hyp, Ile, Leu Lys, Met, Phe, Pro, Ser, Thr, Trp, Tyr, and Val) in D or L form, or an unnatural amino acid (e.g. phosphoserine; phosphothreonine; phosphotyrosine; gamma-carboxyglutamate; hippuric acid; octahydroindole-2-carboxylic acid; statine; 1,2,3,4,-tetrahydroisoquinoline-3-carboxylic acid; penicillamine; ornithine; citrulline; α-methyl-alanine; para-benzoylphenylalanine; phenylglycine; propargyl-glycine; sarcosine; and tert-butylglycine) residue having one or more open valences. Other unnatural amino acids include those represented by the formula $NH_2(CH_2)_y COOH$, wherein y=2–20, and preferably 2–12, and include the aminoalkanoic acids such as ε-amino caproic acid ($H_2N$—$(CH_2)_5$—COOH).

The term also comprises natural and unnatural amino acids bearing amino protecting groups such as acetyl, acyl, trifluoroacetyl, and benzyloxycarbonyl), as well as natural and unnatural amino acids protected at carboxy with protecting groups such as a $C_1$–$C_6$ alkyl, phenyl or benzyl ester and amide. Other suitable amino and carboxy protecting groups are known to those skilled in the art. See for example, T. W. Greene, *Protecting Groups in Organic Synthesis*; Wiley: New York, 1981; D. Voet, Biochemistry, Wiley: New York, 1990; L. Stryer, *Biochemistry*, ($3^{rd}$ Ed), W.H. Freeman and Co.: New York, 1975; J. March, *Advanced Organic Chemistry, Reactions, Mechanisms and Structure*, ($2^{nd}$ Ed.), McGraw Hill: New York, 1977; F. Carey and R. Sundberg, *Advanced Organic Chemistry, Part B: Reactions and Synthesis*, ($2^{nd}$ Ed.), Plenum: New York, 1977; and references cited therein.

As used herein, a "retrovirus" includes any virus that expresses reverse transcriptase. Examples of a retrovirus include, but are not limited to, HIV-1, HIV-2, HTLV-I, HTLV-II, FeLV, FIV, SIV, AMV, MMTV, and MoMuLV.

As used herein, "reverse transcriptase (RT)" refers to an enzyme having an NNI binding site similar to that of HIV-1 RT and to which ligands which bind the composite binding pocket of the invention bind. One means by which RT activity can be determined is by measuring viral replication. One measure of HIV-1 viral replication is the p24 core antigen enzyme immunoassay, for example, using the assay commercially available from Coulter Corporation/Immunotech, Inc. (Westbrooke, Mich.). Another means by which RT activity is analyzed is by assay of recombinant HIV-1 reverse transcriptase (rRT) activity, for example, using the Quan-T—RT assay system commercially available from Amersham (Arlington Heights, Ill.) and described in Bosworth, et al., Nature 1989, 341:167–168.

As used herein, a compound that "inhibits replication of human immunodeficiency virus (HIV)" means a compound that, when contacted with HIV-1, for example, via HIV-infected cells, effects a reduction in the amount of HIV-1 as compared with untreated control. Inhibition of replication of HIV-1 can be measured by various means known in the art, for example, the p24 assay disclosed herein.

As used herein, a compound that is useful in "salvage therapy," means a compound that can be taken with any regimen after a patient's initial treatment regimen has failed.

The term host, as used herein, refers to an unicellular or multicellular organism in which the virus can replicate, including cell lines and animals, and preferably a human. Alternatively, the host can be carrying a part of the HIV genome, whose replication or function can be altered by the compounds of the present invention. The term host specifically refers to infected cells, cells transfected with all or part of the HIV genome and animals, in particular, primates (including chimpanzees) and humans. In most animal applications of the present invention, the host is a human patient. Veterinary applications, in certain indications, however, are clearly anticipated by the present invention (such as chimpanzees).

IV. Combination or Alternation Therapy

In a preferred but not necessary embodiment, phenylindoles of the present invention is administered in combination or alternation with another anti-HIV agent. In one embodiment the effect of administration of the two or more agents in combination or alternation is synergistic.

Drug resistance most typically occurs by mutation of a gene that encodes for an enzyme used in the viral replication cycle, and most typically in the case of HIV, in either the reverse transcriptase or protease genes. It has been demonstrated that the efficacy of a drug against HIV infection can be prolonged, augmented, or restored by administering the compound in combination or alternation with a second, and perhaps third, antiviral compound that induces a different mutation(s) from that selected for by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

The second antiviral agent for the treatment of HIV, in one embodiment, can be a protease inhibitor, a reverse transcriptase inhibitor (a "RTI"), which can be either a synthetic nucleoside reverse transcriptase inhibitor (a "NRTI") or a non-nucleoside reverse transcriptase inhibitor (a "NNRTI"), and HIV-integrase inhibitor, or a chemokine inhibitor. In other embodiments, the second (or third) compound can be a pyrophosphate analog, or a fusion binding inhibitor. A list compiling resistance data collected in vitro and in vivo for a number of antiviral compounds is found in Schinazi et al., Mutations in retroviral genes associated with drug resistance, *International Antiviral News*, Volume 5 (8), International Medical Press 1997.

In preferred embodiments, the phenylindole is administered in combination or alternation with FTC (2',3'-dideoxy-3'-thia-5-fluorocytidine); 141W94 (amprenavir, GlaxoWellcome, Inc.); Viramune (nevirapine), Rescriptor (delavirdine); DMP-266 (efavirenz), DDI (2',3'-dideoxyinosine); 3TC (3'-thia-2',3'-dideoxycytidine); or DDC (2',3'-dideoxycytidine). In another preferred embodiment, the phenylindole is administered in combination or alternation with abacavir (1592U89), which is (1S, 4R)-4-[2-amino-6-cyclopropyl-amino)-9H-purin-9-yl]-2-cyclopentene-1-methanol succinate, D4T or AZT.

Other examples of antiviral agents that can be used in combination or alternation with the compounds disclosed herein for HIV therapy include 3TC; foscarnet; carbovir, acyclovir, interferon, stavudine, and β-D-dioxolane nucleosides such as β-D-dioxolanylguanine (DXG), β-D-dioxolanyl-2,6-diaminopurine (DAPD), and β-D-dioxolanyl-6-chloropurine (ACP).

Preferred protease inhibitors include indinavir ({1 (1,S, 2R), 5(S)]-2,3,5-trideoxy-N-(2,3-dihydro-2-hydroxy-1H-inden-1-yl)-5-[2-[[(1,1-dimethylethyl)amino]carbonyl]-4-(3-pyridinylmethyl)-1-piperazinyl]-2-(phenylmethyl)-D-erythro-pentoamide sulfate; Merck), nelfinavir (Agouron), ritonavir (Abbott), saquinavir (Roche) and DMP-450 {[4R-4(r-a,5-a,6-b,7-6)]-hexahydro-5,6-bis(hydroxy)-1,3-bis(3-amino)phenyl]methyl)-4,7-bis(phenylmethyl)-2H-1,3-diazepin-2-one}-bismesylate (Triangle Pharmaceuticals, Inc.).

Nonlimiting examples of other compounds that can be administered in combination or alternation with the phenylindole to augment the properties of the drug on administration include abacavir: (1S,4R)-4-[2-amino-6-cyclopropyl-amino)-9H-purin -9-yl]-2-cyclopentene-1-methanol succinate (1592U89, a carbovir analog; GlaxoWellcome); BILA 1906: N-{1S-[[[3-[2S-{(1,1-dimethylethyl)amino]carbonyl}-4R-]3-pyridinylmethyl)thio]-1-piperidinyl]-2R-hydroxy-1S-(phenylmethyl)propyl]amino]carbonyl]-2-methylpropyl}-2-quinolinecarboxamide (Bio Mega/Boehringer-Ingelheim); BILA 2185: N-(1,1-dimethylethyl)-1-[2S-[[2-2,6-dimethyl-phenoxy)-1-oxoethyl]amino]-2R-hydroxy-4-phenylbutyl]4R-pyridinylthio)-2-piperidine-carboxamide (Bio Mega/Boehringer-Ingelheim); BM+51.0836:triazoloisoindolinone derivative; BMS 186,318: aminodiol derivative HIV-1 protease inhibitor (Bristol-Myers-Squibb); d4API: 9-[2,5-dihydro-5-(phosphonomethoxy)-2-furanyl]-adenine (Gilead); stavudine: d4T, 2',3'-dide-hydro-3'-deoxythymidine (Bristol-Myers-Squibb); HBY097: S-4-isopropoxycarbonyl-6-methoxy-3-(methylthio-methyl)-3,4-dihydroquinoxalin-2 (1H)-thione; HEPT: 1-[(2-hydroxyethoxy)methyl]6-(phenylthio)-thymine; KNI-272: (2S,3S)-3-amino-2-hydroxy-4-phenylbutyric acid-containing tripeptide; L-697,593; 5-ethyl-6-methyl-3-(2-phthalimido-ethyl)pyridin-2 (1H)-one; L-735,524: hydroxy-aminopentane amide HIV-1 protease inhibitor (Merck); L-697,661: 3-{[(-4,7-dichloro-1,3-benzoxazol-2-yl)methyl]amino}-5-ethyl-6-methylpyridin-2 (1H)-one; L-FDDC: (−)-β-L-5-fluoro-2',3'-dideoxycytidine; L-FDOC: (−)-β-L-5-fluorodioxolane cytosine; nevirapine: 11-cyclopropyl-5,11-dihydro-4-methyl-6H-dipyridol-[3,2-b:2',3'-e]diazepin-6-one (Boehringer-Ingelheim); PFA: phosphonoformate (foscarnet; Astra); PMEA: 9-(2-phosphonylmethoxyethyl) adenine (Gilead); PMPA: (R)-9-(2-phosphonylmethoxypropyl)-adenine (Gilead); Ro 31-8959: hydroxyethylamine derivative HIV-1 protease inhibitor (Roche); RPI-3121: peptidyl protease inhibitor, 1-[(3 s)-3-(n-alpha-benzyloxycarbonyl)-1-asparginyl)-amino-2-hydroxy-4-phenylbutyryl]-n-tert-butyl-1-proline amide; 2720: 6-chloro-3,3-dimethyl-4-(isopropenyloxycarbonyl)-3, 4-dihydro-quinoxalin-2 (1H)thione; SC-52151: hydroxyethylurea isostere protease inhibitor (Searle); SC-55389A: hydroxyethyl-urea isostere protease inhibitor (Searle); TIBO R82150: (+)-(5S)-4,5,6,7-tetrahydro-5-methyl-6-(3-methyl-2-butenyl)-imidazo-[4,5,1-jk]-[1,4]-benzodiazepin-2 (1H)-thione (Janssen); TIBO 82913: (+)-(5S)-4,5,6,7-tetrahydro-9-chloro-5-methyl-6-(3-methyl-2-butenyl)imidazo[4,5,1jk]-[1,4]-benzodiazepin-2-(1H)-thione (Janssen); TSAO-m3T:[2',5'-bis-O-(tertbutyldimethylsilyl)-3'-spiro-5'-(4'-amino-1',2'-oxathiole-2',2'-dioxide)]-β-D-pentofuranosyl-N3-methylthymine; U90152: 1-[3-[(1-methylethyl)-amino]

2-pyridinyl]-4-[[5-[(methylsulphonyl)-amino]-1H-indol-2yl]-carbonyl]-piperazine; UC: thiocarboxanilide derivatives (Uniroyal); UC-781=N-[4-chloro-3-(3-methyl-2-butenyloxy)phenyl]-2-methyl-3-furancarbothioamide; UC-82=N-[4-chloro-3-(3-methyl-2-butenyloxy)phenyl]-2-methyl-3-thiophenecarbothioamide; VB 11,328: hydroxyethyl-sulphonamide protease inhibitor (Vertex); VX-478: amprenavir, 141W94, hydroxyethyl-sulphonamide protease inhibitor (Vertex/Glaxo Wellcome); XM 323: cyclic urea protease inhibitor (Dupont Merck), famciclovir, gancyclovir and penciclovir. In another embodiment, the phenylindole is administered in combination with the protease inhibitor LG 1350.

In general, during alternation therapy, an effective dosage of each agent is administered serially, whereas in combination therapy, effective dosages of two or more agents are administered together. The dosages will depend on such factors as absorption, biodistribution, metabolism and excretion rates for each drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. Examples of suitable dosage ranges for anti-HIV compounds, including nucleoside derivatives (e.g. D4T, DDI, and 3TC) or protease inhibitors, for example, nelfinavir and indinavir, can be found in the scientific literature and in the Physicians Desk Reference. Many examples of suitable dosage ranges for other compounds described herein are also found in public literature or can be identified using known procedures. These dosage ranges can be modified as desired to achieve a desired result.

The disclosed combination and alternation regiments are useful in the prevention and treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

V. Pharmaceutical Compositions

Humans suffering from effects caused by any of the diseases described herein, and in particular, HIV infection, can be treated by administering to the patient an effective amount of the phenylindole, optionally in combination or alternation with another anti-HIV agent, or with a pharmaceutically acceptable salt or prodrug thereof in the presence of a pharmaceutically acceptable carrier or diluent. In one embodiment, humans infected with HIV can be effectively treated by administering to the patient an effective amount of the phenylindole or a pharmaceutically acceptable salt or prodrug thereof in the presence of a pharmaceutically acceptable carrier or diluent. For multiple drug resistant patients, the phenylindole is either administered alone or in combination. The active materials can be administered by any appropriate route, for example, orally, parenterally, enterally, intravenously, intradermally, subcutaneously, transdermally, intranasally or topically, in liquid or solid form.

The active compound(s) are included in the pharmaceutically acceptable carrier or diluent in an amount sufficient to deliver to a patient a therapeutically effective amount of compound to inhibit viral replication in vivo, especially HIV replication, without causing serious toxic effects in the treated patient. By "inhibitory amount" is meant an amount of active ingredient sufficient to exert an inhibitory effect as measured by, for example, an assay such as the ones described herein.

A preferred dose of the compound for all the above-mentioned conditions will be in the range from about 1 to 75 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent phenylindole to be delivered. If the derivative exhibits activity in itself, the effective dosage can be estimated as above using the weight of the derivative, or by other means known to those skilled in the art.

The compounds are conveniently administered in unit any suitable dosage form, including but not limited to one containing 7 to 3000 mg, preferably 70 to 1400 mg of active ingredient per unit dosage form. An oral dosage of 50 to 1000 mg is usually convenient.

Ideally, the active ingredient should be administered to achieve peak plasma concentrations of the active compound of from about 0.02 to 70 micromolar, preferably about 0.5 to 10 $\mu$M. This may be achieved, for example, by the intravenous injection of a 0.1 to 25% solution of the active ingredient, optionally in saline, or administered as a bolus of the active ingredient.

The concentration of active compound in the drug composition will depend on absorption, distribution, metabolism and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible bind agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, chewing gum or the like. A syrup may contain, in addition to the active compounds, sucrose as a sweetening agent and certain preservatives, dyes and colorings and flavors.

The compounds or their pharmaceutically acceptable derivative or salts thereof can also be mixed with other active materials that do not impair the desired action, or with materials that supplement the desired action, such as antibiotics, antifungals, antiinflammatories, protease inhibitors, or other nucleoside or non-nucleoside antiviral agents, as discussed in more detail above. Solutions or suspensions used for parental, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Liposomal suspensions (including liposomes targeted to infected cells with monoclonal antibodies to viral antigens) are also preferred as pharmaceutically acceptable carriers. these may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

VI. Process of Preparation of the Active Compounds

Figure 2:
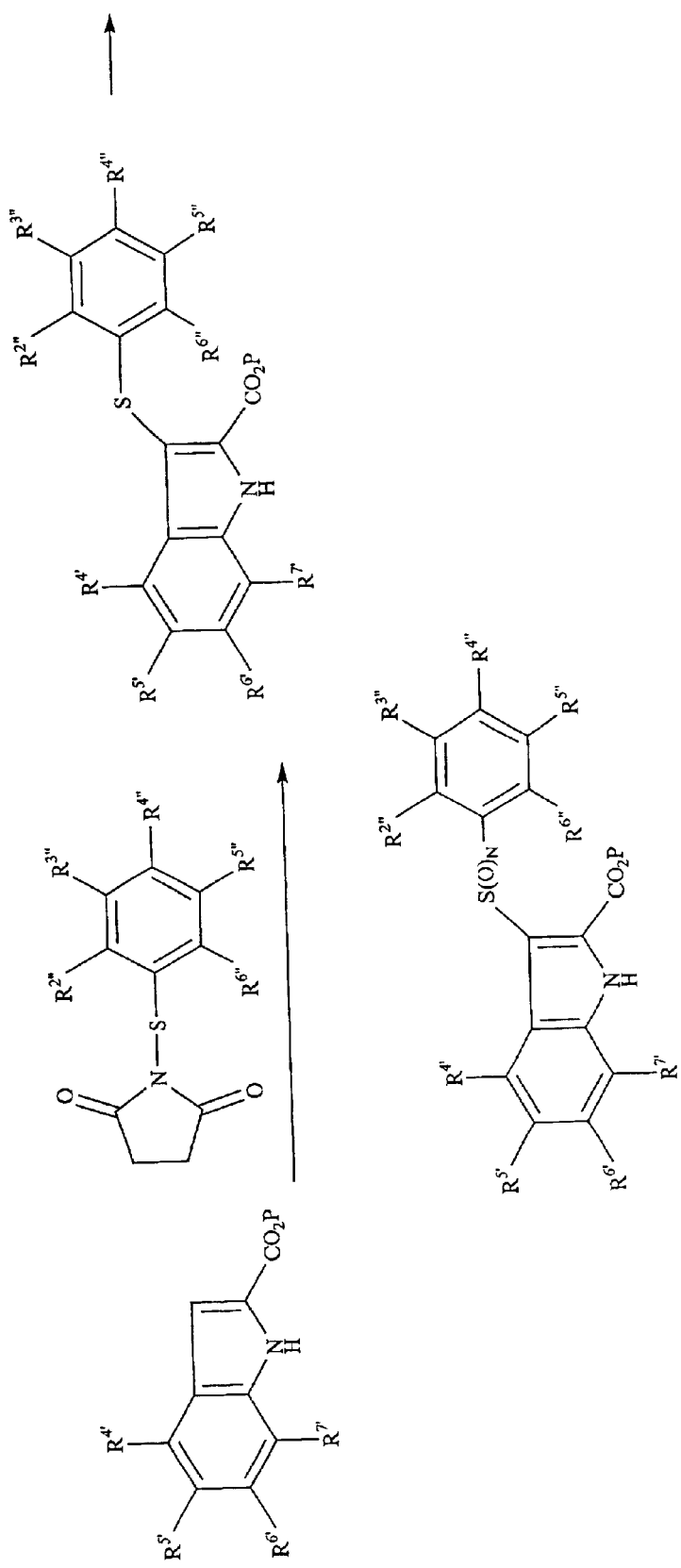
FIG. 2 is a nonlimiting illustrative example of the synthesis of phenylindoles as described herein; wherein P represents hydrogen or alkyl, in particular methyl, ethyl, butyl or propyl, preferably ethyl.
Figure 2:
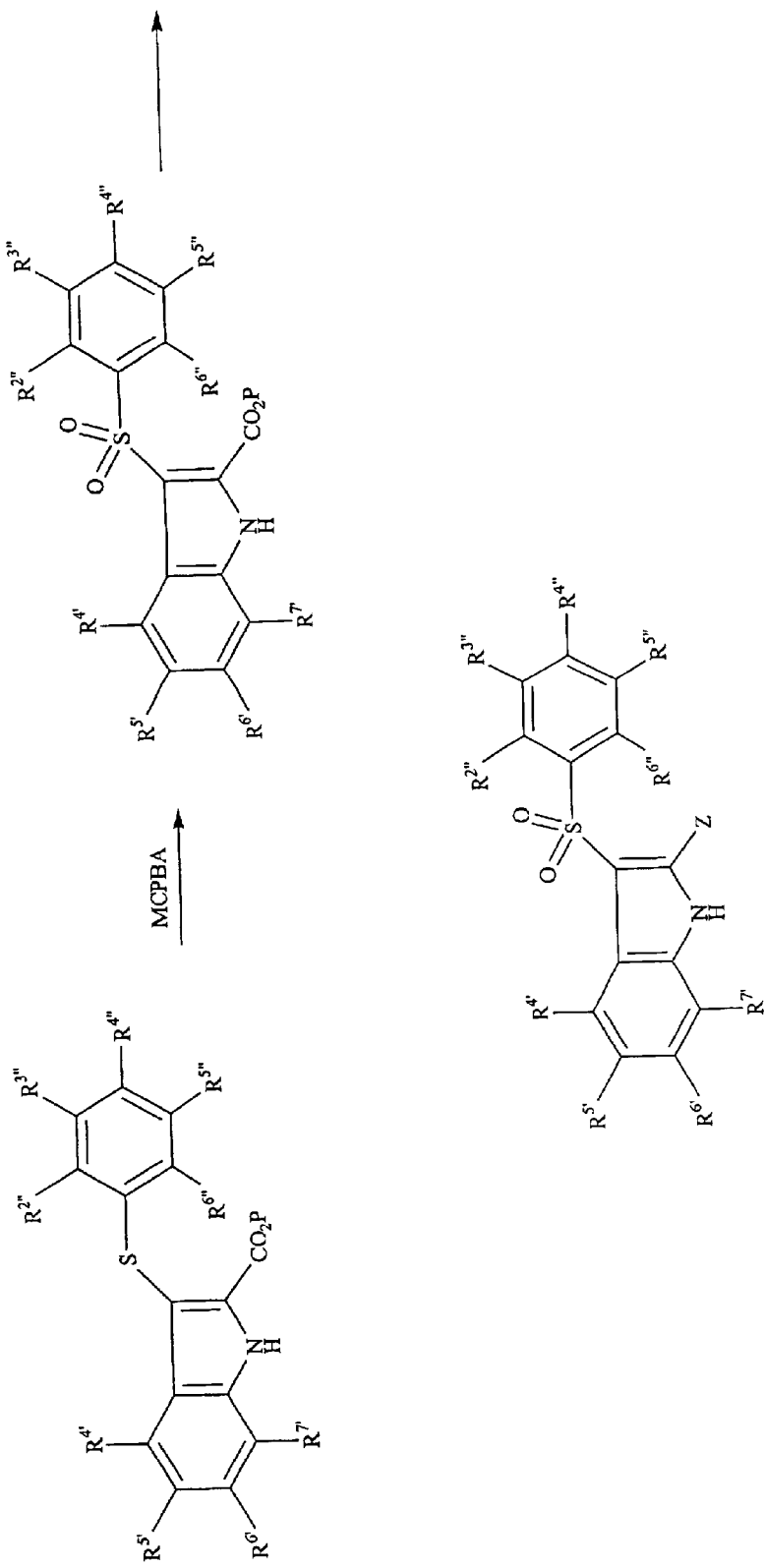
Figure 3:
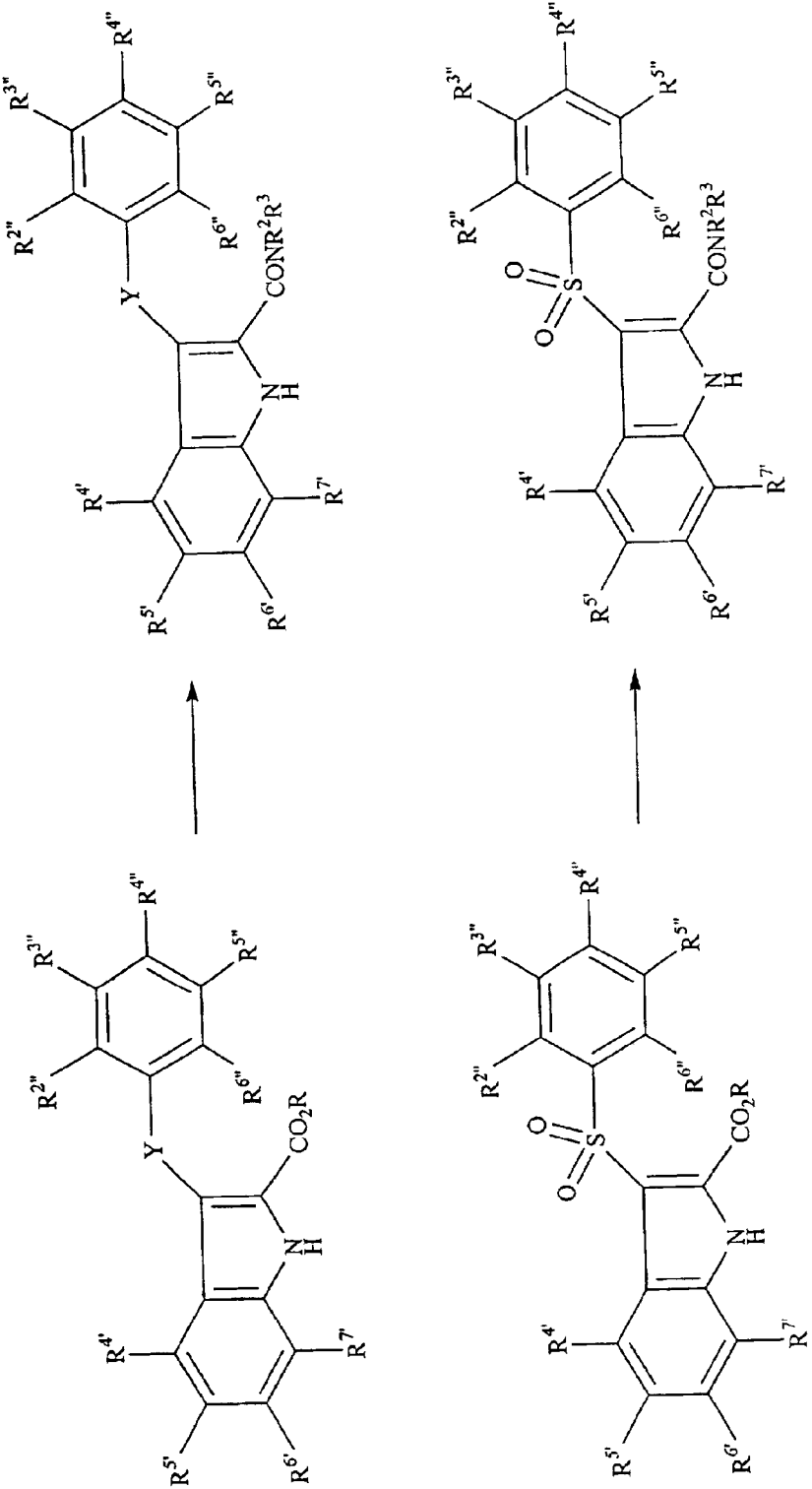
FIGS. 3 and 4 are additional nonlimiting illustrative example of the synthesis of phenylindoles as described herein.
Figure 4:
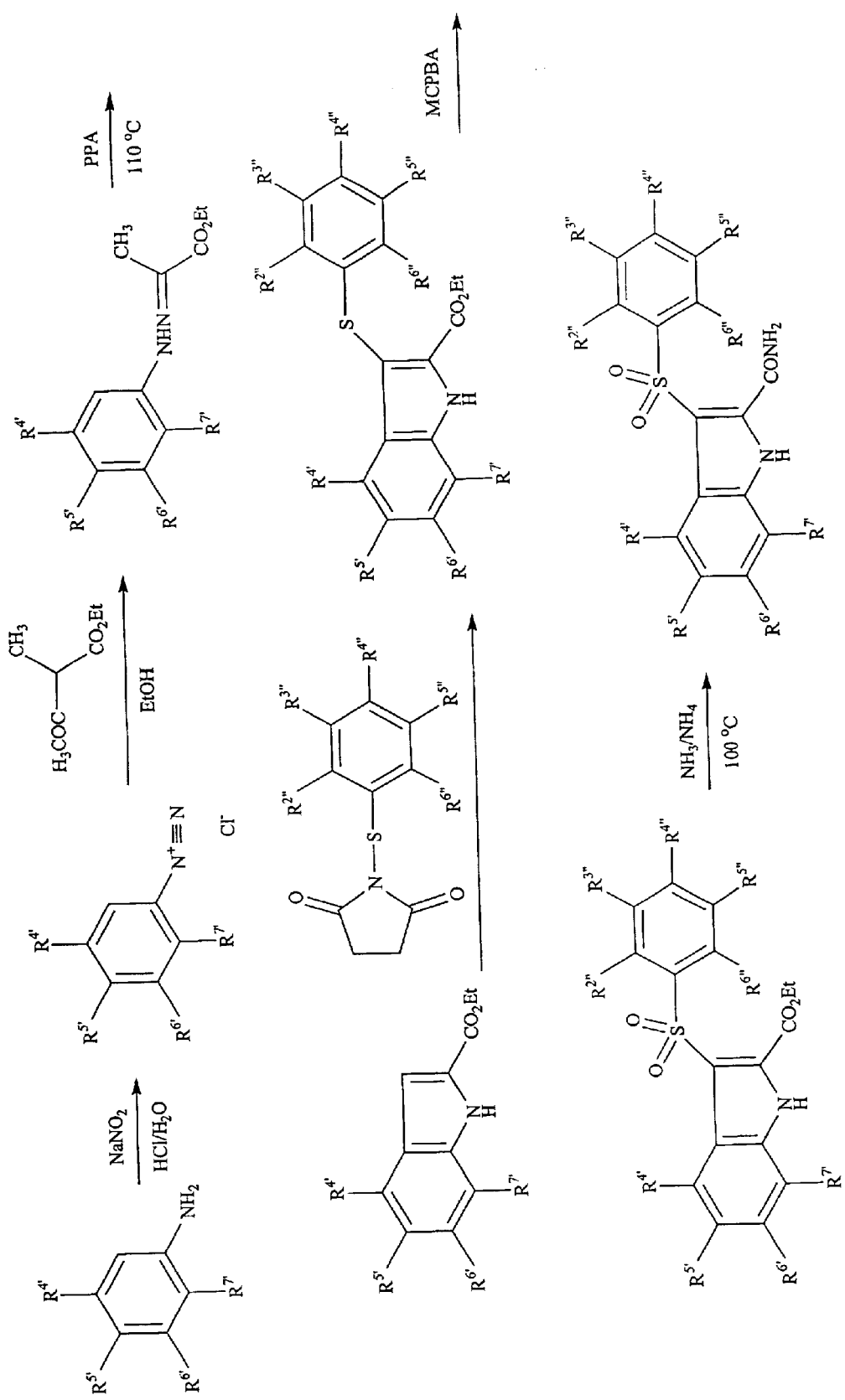
Figure 5:
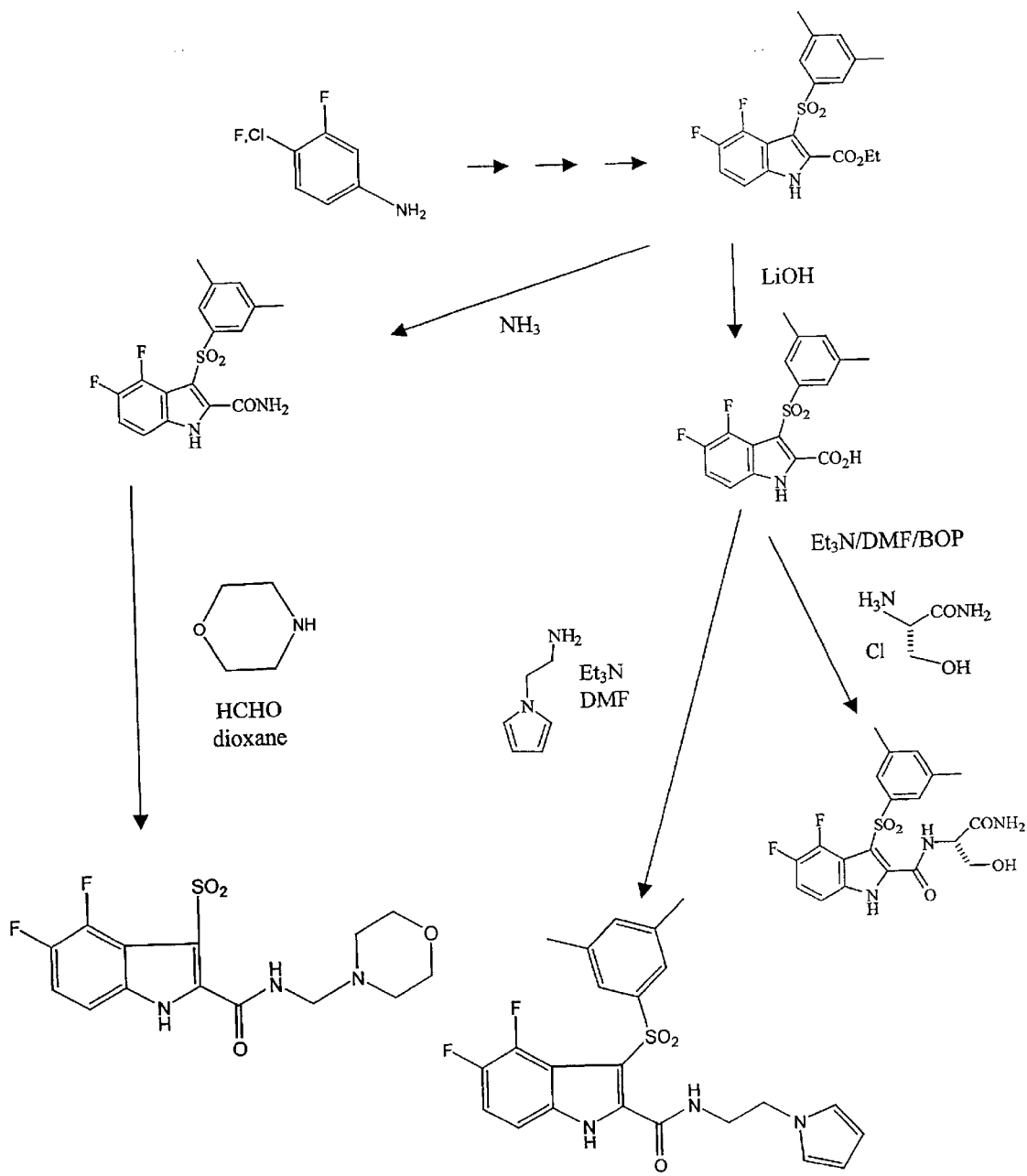
FIG. 5 is a schematic of a method of manufacture of the compound of the formula.

The phenylindoles can be synthesized using any means known in the art. In particular, the methods disclosed in U.S. Pat. No. 5,527,819, hereby incorporated by reference in its entirety for its disclosure of relevant synthetic methods, can be used to synthesize the compounds of the present invention. In general, the compounds of the present invention can be synthesized via the general methods disclosed in FIGS. 1–4. In particular, the following species can by synthesized by the following methods.

a) Ethyl indole-2-caboxylates—2a–i (Scheme 1, Examples 1–3)

Ethyl 5,6-dichloroindole-2-carboxylate 2a was prepared according to literature (*J. Med. Chem.*, 1998, 41, 1568–1573). Ethyl indole-2-caboxylates 2b–i were synthesized starting from proper anilines or phenylhydrazines which were transformed into the related phenylhydrazones 1 and then cyclized to indoles (Fischer indole synthesis, Robinson, "The Fischer indole synthesis", Wiley, New York, 1983. The Japp-Klingemann reaction, *Org. Reactions,* 1959, 10, 143–178).

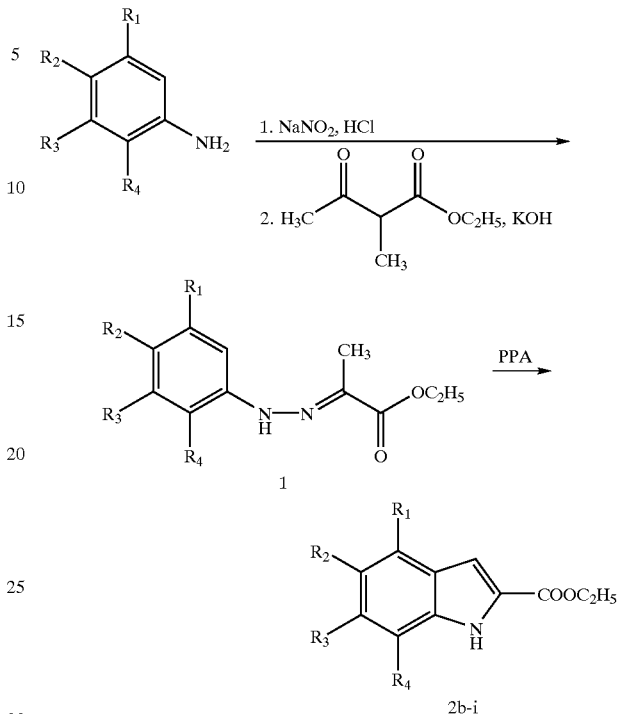

Scheme 1

2b: $R_1 = H, R_2 = Cl, R_3 = H, R_4 = Cl$; 2c: $R_1 = F, R_2 = F, R_3 = H, R_4 = H$;
2d: $R_1 = H, R_2 = F, R_3 = F, R_4 = H$; 2e: $R_1 = H, R_2 = F, R_3 = H, R_4 = F$;
2f: $R_1 = H, R_2 = Cl, R_3 = F, R_4 = H$; 2g: $R_1 = F, R_2 = Cl, R_3 = H, R_4 = H$;
2h: $R_1 = Cl, R_2 = F, R_3 = H, R_4 = H$; 2i: $R_1 = H, R_2 = F, R_3 = Cl, R_4 = H$.

b) 3-Arylsulfonylindole-2-carboxyamides—5a–g (Scheme 2, Examples 4–7)

The reaction of ethyl indole-2-caboxylates 2a–i with N-(3,5-dimethylphenylthio)-succinimide in the presence of sodium hydride afforded the ethyl 3-(3,5-dimethylphenylthio)indole-2-caboxylates 3a–i which were oxidized to the related sulfones 4a–i by treatment with 3-chloroperoxybenzoic acid. Transformation of esters 3a–i into related amides 4a–i was reached by heating in a sealed tube with ammonium hydroxide.

Scheme 2

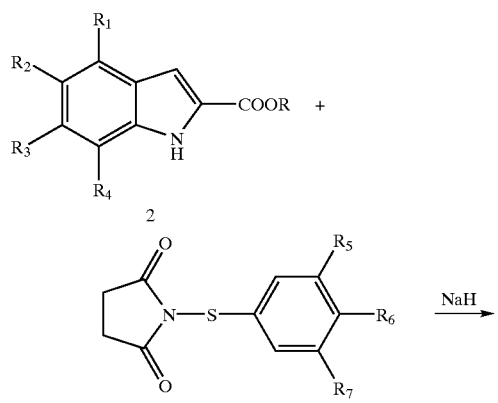

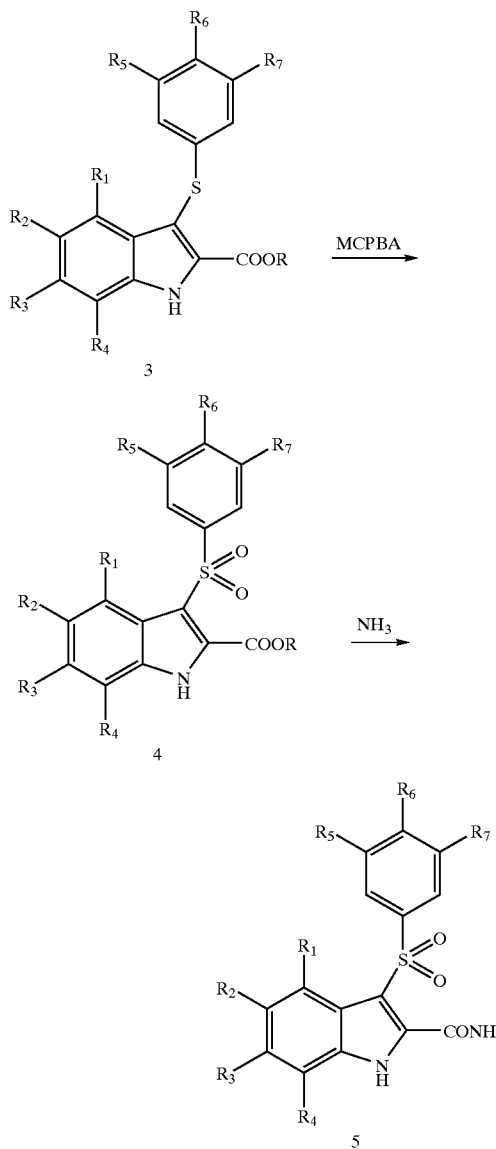

3a-i, k, l; 4a-i, k, l; 5a-i, k, l: R = C₂H₅; 3-5j: R = CH₃.
3-5a: R₁ = H, R₂ = Cl, R₃ = Cl, R₄ = H; 3-5b: R₁ = H, R₂ = Cl, R₃ = H, R₄ = Cl;
3-5c: R₁ = F, R₂ = F, R₃ = H, R₄ = H; 3-5d: R₁ = H, R₂ = F, R₃ = F, R₄ = H;
3-5e: R₁ = H, R₂ = F, R₃ = H, R₄ = F; 3-5f: R₁ = H, R₂ = Cl, R₃ = F, R₄ = H;
3-5g: R₁ = F, R₂ = Cl, R₃ = H, R₄ = H; 3-5h: R₁ = Cl, R₂ = F, R₃ = H, R₄ = H;
3-5i: R₁ = H, R₂ = F, R₃ = Cl, R₄ = H; 3-5j: R₁ = H, R₂ = Cl, R₃ = H, R₄ = H,
3-5k: R₁ = H, R₂ = NO₂, R₃ = H, R₄ = H. 3-5l: R₁ = H, R₂ = CH₃CO, R₃ = H, R₄ = H.
3a-l, 4a-l, 5a-l: R₅ = R₇ = CH₃, R₆ = H.

c) 3-Arylsulthioindole-2-carboxyhydrazides—6a–d, f and 7a–f—and 3-arylsulfonylindole-2-carboxyhydrazides—8a, b, d–f, 9a–f, 10 and 11 (Schemes 3 and 4, Examples 8–10)

Treatment of ethyl 3-aryllthioindole-2-caboxylates or 3-arylsulfonylindole-2-caboxylates with proper hydrazines afforded 3-arylsulthioindole-2-carboxyhydrazides (6a–d, f and 7a–f) and 3-arylsulfonylindole-2-carboxyhydrazides (8a, b, d–f and 9a–f, 10), respectively. Reaction of 7e with acetone in the presence of sodium cyanoborohydride gave 11.

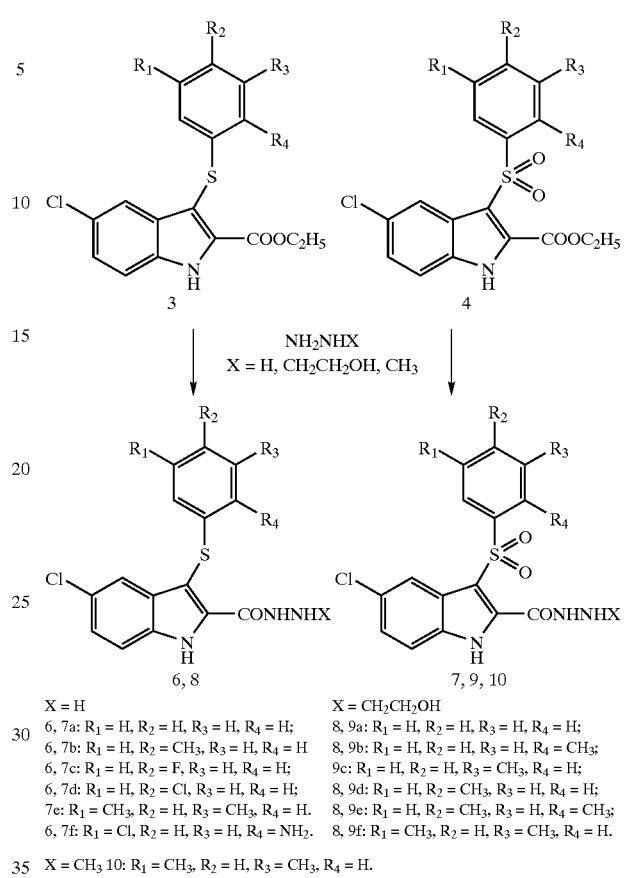

X = H
6, 7a: R₁ = H, R₂ = H, R₃ = H, R₄ = H;
6, 7b: R₁ = H, R₂ = CH₃, R₃ = H, R₄ = H;
6, 7c: R₁ = H, R₂ = F, R₃ = H, R₄ = H;
6, 7d: R₁ = H, R₂ = Cl, R₃ = H, R₄ = H;
7e: R₁ = CH₃, R₂ = H, R₃ = CH₃, R₄ = H.
6, 7f: R₁ = Cl, R₂ = H, R₃ = H, R₄ = NH₂.

X = CH₂CH₂OH
8, 9a: R₁ = H, R₂ = H, R₃ = H, R₄ = H;
8, 9b: R₁ = H, R₂ = H, R₃ = H, R₄ = CH₃;
9c: R₁ = H, R₂ = H, R₃ = CH₃, R₄ = H;
8, 9d: R₁ = H, R₂ = CH₃, R₃ = H, R₄ = H;
8, 9e: R₁ = H, R₂ = CH₃, R₃ = H, R₄ = CH₃;
8, 9f: R₁ = CH₃, R₂ = H, R₃ = CH₃, R₄ = H.

X = CH₃ 10: R₁ = CH₃, R₂ = H, R₃ = CH₃, R₄ = H.

Scheme 4

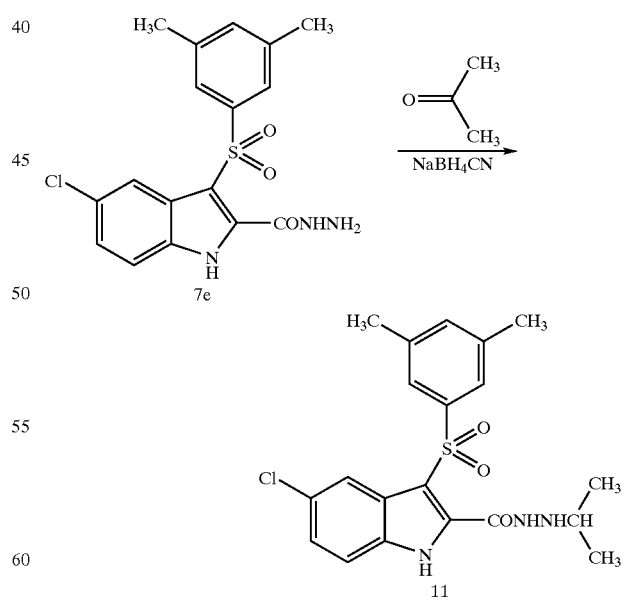

d) 1-[5-Chloro-3-(3,5-dimethylphenylsulfonyl)indol-2-carbonyl]-4-methyl-piperazine—13 (Scheme 5, Examples 11 and 12)

41

Lithium hydroxide hydrolysis of 41 gave 5-chloro-3-(3,5-dimethylphenyl-sulfonyl)indole -2-carboxylic acid (12) with was converted to 13 by reaction with N-methylpiperazine in the presence of benzotriazol-1-yl-oxy-tris(dimethylamino)-phosphonium hexafluorophosphate (BOP reagent) and triethylamine in DMF as a solvent at room temperature.

42

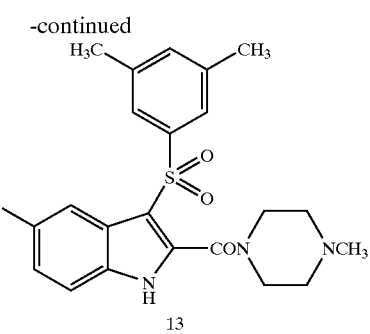

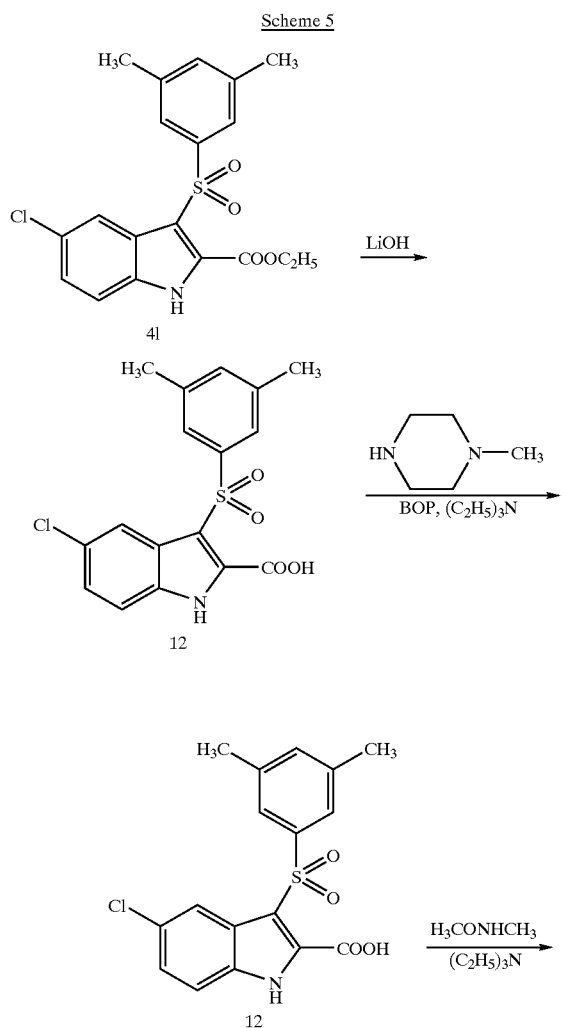

e) 3-trans-[5-Chloro-3-(3,5-dimethylphenylsulfonyl)indol-2-yl]propenamide—18 (Scheme 6, Examples 13–18)

Acid (12) was transformed into N-methyl,N-methoxy 5-chloro-3-(3,5-dimethylphenylsulfonyl)indole-2-carboxyamide (14) by reacting with N,O-dimethyl-hydroxylamine hydrochloride, benzotriazol-1-yloxy-tris (dimethylamino)phosphonium hexafluoro-phosphate (BOP reagent) in the presence of triethylamine and then into 5-chloro-3-(3,5-di-methylphenylsulfonyl)indole-2-carboxyaldehyde acid (15) by lithium aluminium hydride reduction. Reaction of 15 with triethyl phosphono acetate in the presence of potassium carbonate gave ethyl 3-trans-[5-chloro-3-(3,5-dimethylphenyl-sulfonyl)indol -2-yl] propenoate (16), which was transformed to 3-trans-[5-chloro-3-(3,5-dimethylphenylsulfonyl)indol-2-yl]propenoic acid (17) by lithium aluminium hydrolysis and subsequently converted to amide 18 with ammonia in the presence of 1,1'-carbonyldiimidazole. Reaction of acid 17 with the gyi-cine ethyl ester hydrochloride in the presence of BOP and triethylamine afforded 2-[N-[3-trans-[5-chloro-3-(3,5-dimethylphenylsulfonyl)indol-2-yl]propenamido]]-acetic acid ethyl ester) (19) which was transformed into the related amide 20 with ammonium hydroxide at 60° C.

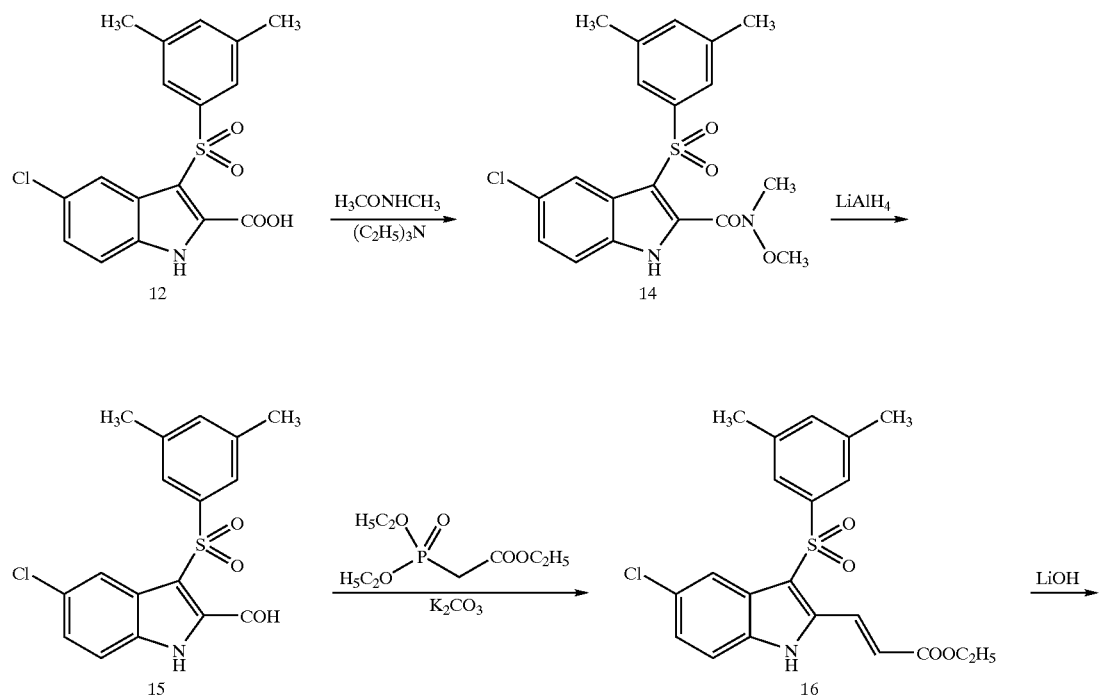

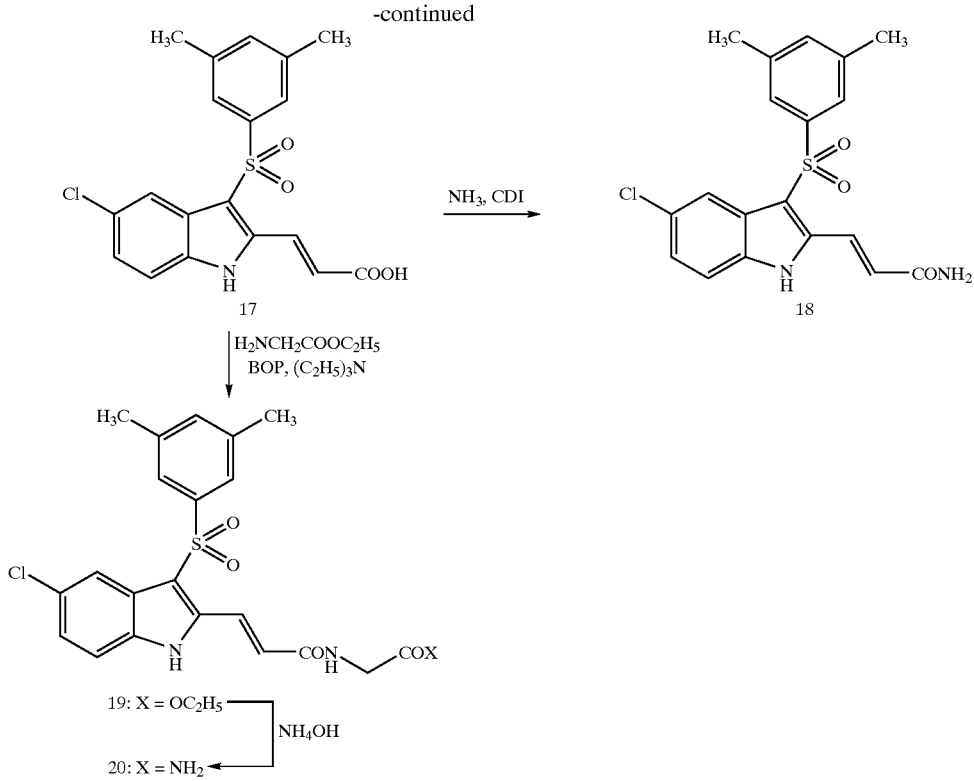

f) 2-[N-[5-Chloro-3-(3,5-dimethylphenylsulfonyl)indol-2-carboxyamido]]-acetamide —21 (Scheme 7, Examples 19–22)

Reaction of the acid 12 with the glycine ethyl ester hydrochloride in the presence of BOP and triethylamine afforded 2-N-[5-Chloro-3-(3,5-dimethylphenylsulfonyl)indol-2-carboxy-amido]]-acetic acid ethyl ester (21) which was transformed into amide 22 by heating with ammonium hydroxide. By the same way were prepared amides 23 and 24 by heating with cyclopropylamine or morpholine, respectively.

Scheme 7

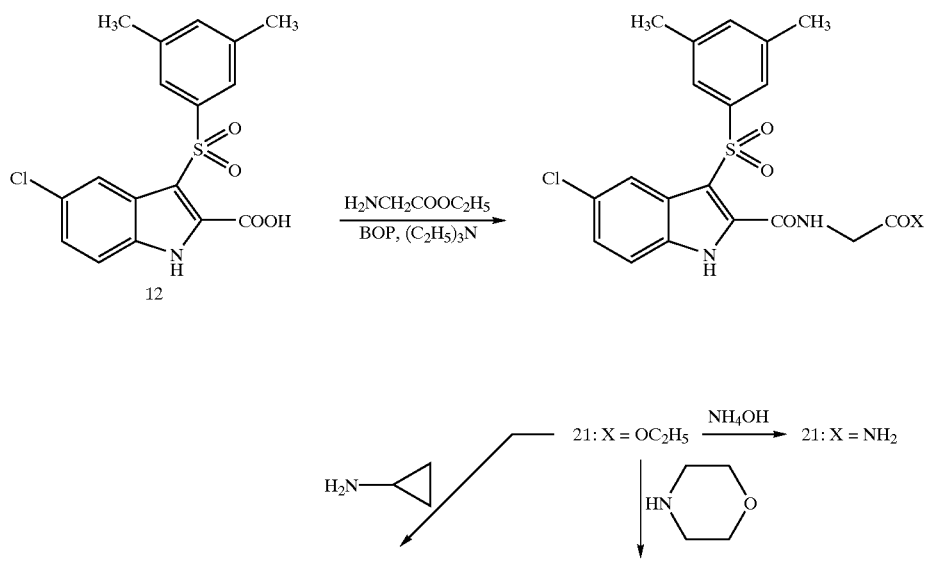

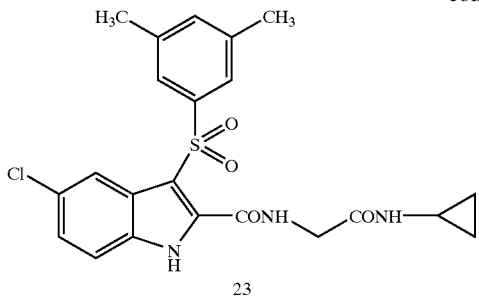

23

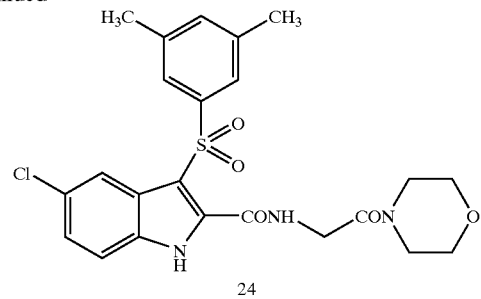

24 g) 5-(1H-Pyrrol-1-yl)-3-(3,5-dimethylphenylsulfonyl)indole-2-carboxyamide—25b (Scheme 8, Example 23)

5-Nitro-3-(3,5-dimethylphenylsulfonyl)indole-2-carboxyamide (5k) was reduced 5-amino-3-(3,5-dimethylphenylsulfonyl)indole-2-carboxyamide with hydrogen in the presence of $PtO_2$ (Adams' catalyst) as a catalyst. Transformation into 5-(1H-pyrrol-1-yl)-3-(3,5-dimethyl-phenylsulfonyl)indole-2-carboxylate (25a) was performed by heating with 2,5-dimethoxy-tetrahydrofuran in glacial acetic acid (*Acta Chem. Scand.*, 1952, 6, 667–670; *Acta Chem. Scand.*, 1952, 6, 867–874).

Scheme 8

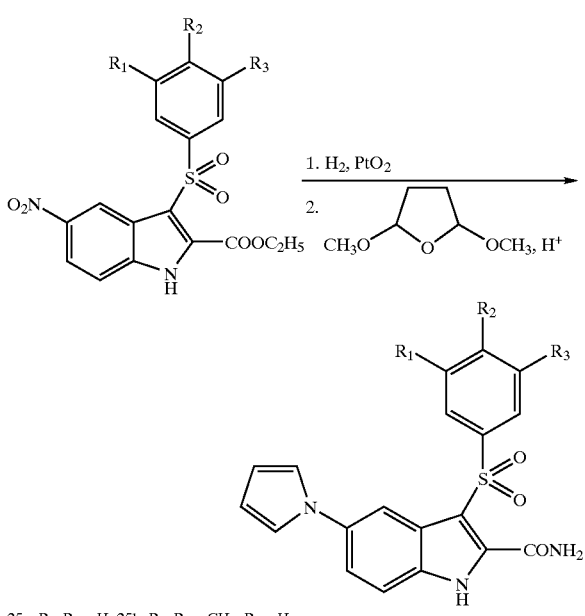

25a: $R_1$–$R_3$ = H, 25b: $R_1$, $R_3$ = $CH_3$; $R_2$ = H.

The following working examples provide a further understanding of the method of the present invention. These examples are of illustrative purpose, and are not meant to limit the scope of the invention. Equivalent, similar, or suitable solvents, reagents or reaction conditions may be substituted for those particular solvents, reagents or reaction conditions described herein without departing from the general scope of the method of synthesis.

EXAMPLES

All melting points (mp) were taken on a Büchi 510 apparatus (uncorrecte). Infrared spectra (IR): Perkin-Elmer 1310 spectrophotometer. Proton nuclear magnetic resonance (1H NMR) spectra: Bruker AM-200 (200 MHz) FT spectrometer. Column chromatographies: alumina Merck (70–230 mesh) and silica gel Merck (70–230 mesh). TLC: Aluminum oxide TLC cards Fluka (aluminum oxide pre-coated aluminum cards with fluorescent indicator at 254 nm) and silica gel TLC cards Fluka (silica gel precoated aluminum cards with fluorescent indicator at 254 nm). Developed plates were visualized by spectroline ENF 260C/F UV apparatus. Organic solutions were dried over anhydrous sodium sulfate. Concentration and evaporation of the solvent after reaction or extraction: rotary evaporator Büchi Rotavapor operating at reduced pressure. Elemental analyses (±0.4% of the theoretical values): laboratories of Dr. M. Zancato, Dipartimento di Scienze Farmaceutiche, University of Padova (Italy).

Example 1

Synthesis of Ethyl Pyruvate 4-Chloro-3-Fluorophenylhydrazone

A solution of sodium nitrite (4.76 g, 0.069 mol) in water (6.3 mL) was added dropwise to an ice cooled mixture of 4-chloro-3-fluoroaniline (*J. Am. Chem. Soc.*, 1996, 61, 5130–5133) (10.00 g, 0.069 mol), water (167 mL) and 37% hydrochloric acid (167 mL). After 20 minutes potassium acetate (9.81 g, 0.10 mol) was added, and then a solution of ethyl 2-methylacetoacetate (9.95 g, 0.069 mol), potassium acetate (9.81 g, 0.10 mol) in methanol (67 mL) was dropped while cooling on the ice bad. Reaction was stirred at 0° C. for 3 hours, then extracted with diethyl ether. Organic layer was washed with brine and dried. Removal of the solvent furnished a red oily residue that was treated with ethanol (100 mL) and stirred at room temperature overnight. The solid which formed was filtered a recrystallized from ethanol to give 5.4 g (30%) of title compound, mp 161–163° C. (from ethanol).

Ethyl pyruvate 2,4-difluorophenylhydrazone, yield 40%, mp 153–156° C. (from ethanol).

Ethyl pyruvate 3-chloro-4-fluorophenylhydrazone, yield 17%, mp 89–91° C. (from aqueous ethanol).

Ethyl pyruvate 3,4-difluorophenylhydrazone, yield 53%, mp 112–114 (from ethanol).

Example 2

Synthesis of Ethyl pyruvate 2,4-dichlorophenylhydrazone

A mixture of 2,4-dichlorophenylhydrazine (16.00 g, 0.075 mol), ethyl pyruvate (14.47 g, 10.3 mL, 0.12 mol), glacial acetic acid (0.9 mL), absolute ethanol (105 mL) was refluxed for 2 hours. After cooling at room temperature, the solid which formed was filtered and recrystallized from

Example 3

Synthesis of Ethyl 5-chloro-6-fluoroindole-2-carboxylate (2f) and ethyl 5-chloro-4-fluoroindole-2-carboxylate (2 g)

Ethyl pyruvate 4-chloro-3-fluorophenylhydrazone (5.00 g, 0.0193 mol) was added by portions to PPA (50 g) pre-heated at 110° C., then reaction was stirred for 30 minutes. After cooling at room temperature, ice water was added while stirring. The solid which formed was filtered, washed with water, dried and passed by a silica gel column chromatography (n-hexane:ethyl acetate 1:2 as eluent). First fractions furnished ethyl 5-chloro-6-fluoroindole-2-carboxylate (2f), (1.85 g, 40%), mp 160–164° C. (ethanol). Further elution with the same eluent gave ethyl 5-chloro-4-fluoroindole-2-carboxylate (2 g) (0.9 g, 19%), mp 186–190° C. (ethanol).

Ethyl 5,7-dichloroindole-2-carboxylate (2b), yield 37%, mp 143–145° C. (from ethanol).
Ethyl 4,5-difluoroindole-2-carboxylate (2c), yield 15%, mp 166–168° C. (from ethanol).
Ethyl 4,5-difluoroindole-2-carboxylate (2d), yield 22%, mp 171–173° C. (from ethanol.)
Ethyl 5,7-difluoroindole-2-carboxylate (2e), yield 9%, mp 175–177° C. (from ethanol).
Ethyl 4-chloro-5-fluoroindole-2-carboxylate (2 h), yield 18%, mp 183–16° C. (from ethanol).
Ethyl 6-chloro-5-fluoroindole-2-carboxylate (2i), yield 61%, mp 198–200° C. (from ethanol).

Example 4

Synthesis of Ethyl 5-chloro-3-(3,5-dimethylphenylthio)-6-fluoroindole-2-carboxylate (3f)

Boron trifluoride ethyl etherate (0.135 g, 0.12 mL, 0.001 mol) was added to a mixture of ethyl 5-chloro-6-fluoroindole-2-carboxylate (0.75 g, 0.0031 mol), N-(3,5-dimethylphenylthio)-succinimide (0.78 g, 0.0033 mol) and anhydrous dichloromethane (20 mL) under dry argon atmosphere. After stirring at room temperature for 2 hours was added boron trifluoride ethyl etherate (0.27 g, 0.24 mL, 0.002 mol) and then reaction was heated at 45° C. for 2 hours. After cooling reaction was diluted chloroform and brine while shaking. Organic layer was separated, washed with saturated solution of sodium hydrogen carbonate, then with brine and dried. The solvent was evaporated to give 1.2 g (100%) of satisfactory pure title compound, mp 170–173° C. (from ethanol).

Ethyl 5,6-dichloro-3-(3,5-dimethylphenylthio)indole-2-carboxylate (3a), yield 96%, mp 192–195° C. (from ethanol).
Ethyl 5,7-dichloro-3-(3,5-dimethylphenylthio)indole-2-carboxylate (3b), not purified.
Ethyl 3-(3,5-dimethylphenylthio)-4,5-difluoroindole-2-carboxylate (3c), yield 97%, mp 148–150° C. (from ethanol).
Ethyl 3-(3,5-dimethylphenylthio)-5.6-difluoroindole-2-carboxylate (3d), yield 98%, mp 171–174° C. (from ethanol).
Ethyl 3-(3,5-dimethylphenylthio)-5,7-difluoroindole-2-carboxylate (3e), not purified.
Ethyl 5-chloro-3-(3,5-dimethylphenylthio)-4-fluoroindole-2-carboxylate (3g), yield 51%, mp 149–151° C. (from ethanol).
Ethyl 4-chloro-3-(3,5-dimethylphenylthio)-5-fluoroindole-2-carboxylate (3h), yield 77%, mp 184–186° C. (from ethanol).
Ethyl 6-chloro-3-(3,5-dimethylphenylthio)-5-fluoroindole-2-carboxylate (3i), yield 61%, mp 186–190° C. (from ethanol).
Methyl 5-chloro-3-(3,5-dimethylphenylthio)indole-2-carboxylate (3j), yield 77%, mp 174–175° C. (from toluene/cyclohexane).
Ethyl 5-nitro-3-(3,5-dimethylphenylthio)indole-2-carboxylate (3k), yield 46%, mp 212–213° C. (from ethanol).
Ethyl 5-acetyl-3-(3,5-dimethylphenylthio)indole-2-carboxylate (3l), yield 70%, mp 164–166° C. (from ethanol).

Example 5

Synthesis of Ethyl 5-chloro-3-(3,5-dimethylphenysulfonyl)-6-fluoroindole-2-carboxylate (4f)

3-Chloroperoxybenzoic acid (1.32 g, 0.00766 mol) was added to an ice cooled solution of ethyl 5-chloro-3-(3,5-dimethylphenylthio)-6-fluoroindole-2-carboxylate (3f) (1.0 g, 0.00264 mol) in chloroform (42 mL). Reaction was stirred at room temperature for 1.5 hours, poured on crushed ice and extracted with chloroform. Organic solution was shaken with saturated solution of sodium hydrogen carbonate, then with brine. After concentration to a small volume, the solution was passed through a silica gel column chromatography (ethyl acetate as eluent) to furnish 0.9 g (83%) of title compound, mp 236–240° C. (from ethanol).

Ethyl 5,6-dichloro-3-(3,5-dimethylphenylsulfonyl)indole-2-carboxylate (4a), yield 82%, mp 196–197° C. (from aqueous ethanol).
Ethyl 5,7-dichloro-3-(3,5-dimethylphenylsulfonyl)indole-2-carboxylate (4b), yield 50%.
Ethyl 3-(3,5-dimethylphenylsulfonyl)-4,5-difluoroindole-2-carboxylate (4c), yield 27%, mp 176–178° C. (from ethanol).
Ethyl 3-(3,5-dimethylphenylsulfonyl)-5.6-difluoroindole-2-carboxylate (4d), yield 100%, mp 232–235° C. (from ethanol).
Ethyl 3-(3,5-dimethylphenylsulfonyl)-5.7-difluoroindole-2-carboxylate (4e), yield 100%, mp 208–210° C. (from ethanol).
Ethyl 5-chloro-3-(3,5-dimethylphenylsulfonyl)-4-fluoroindole-2-carboxylate (4 g), yield 89%, mp 224–226° C. (from ethanol).
Ethyl 4-chloro-3-(3,5-dimethylphenylsulfonyl)-5-fluoroindole-2-carboxylate (4h), yield 54%, mp 232–234° C. (from ethanol).
Ethyl 6-chloro-3-(3,5-dimethylphenylsulfonyl)-5-fluoroindole-2-carboxylate (4i), yield 100%, mp 233–235° C. (from ethanol).
Methyl 5-chloro-3-(3,5-dimethylphenylsulfonyl)-indole-2-carboxylate (4j), yield 74%, mp 234–236° C. (from toluene/cyclohexane).
Ethyl 5-nitro-3-(3,5-dimethylphenylsulfonyl)indole-2-carboxylate (4k), yield 100%, mp 255–256° C. (from ethanol).
Ethyl 5-acetyl-3-(3,5-dimethylphenylsulfonyl)indole-2-carboxylate (4l), yield 61%, mp 193–195° C. (from ethanol).

Scheme 9

[Chemical structure 51: 5-acetyl-3-(3,5-dimethylphenylsulfonyl)indole-2-carboxamide] →NaBH₄→ [Chemical structure 26: 5-(1-hydroxyethyl)-3-(3,5-dimethylphenylsulfonyl)indole-2-carboxamide]

Example 6

Synthesis of 5-Chloro-3-(3,5-dimethylphenysulfonyl)-6fluoroindole-2-carboxyamide (5f)

Ethyl 5-chloro-3-(3,5-dimethylphenysulfonyl)-6fluoroindole-2-carboxylate (41) was heated with 30% ammonium hydroxide (25 mL) and ammonium chloride (40 mg) in a sealed tube at 100° C. overnight. After cooling reaction mixture was poured on ice water and stirred for 15 minutes and extracted with ethyl acetate. Organic layer was washed with brine, dried and the solvent evaporated to afford a residue which was purified on silica gel column chromatography (chloroform-ethanol 95:5). Removal of the solvent gave 0.28 g (65%) of title compound, mp 270–270° C. (from ethanol).
5,6-Dichloro-3-(3,5-dimethylphenylsulfonyl)indole-2-carboxyamide (5a), yield 43%, mp 280–282° C. (from ethanol).
5,7-Dichloro-3-(3,5-dimethylphenylsulfonyl)indole-2-carboxyamide (5b), yield 90%, mp >300° C. (from ethanol).
3-(3,5-Dimethylphenylsulfonyl)-4,5-difluoroindole-2-carboxyamide (5c), yield 43%, mp 298–300° C. (from ethanol).
3-(3,5-Dimethylphenylsulfonyl)-5.6-difluoroindole-2-carboxyamide (5d), yield 65%, mp 266–269° C. (from aqueous dimethylformamide).
3-(3,5-Dimethylphenylsulfonyl)-5.7-difluoroindole-2-carboxyamide (5e), yield 75%, mp >300° C. (from aqueous dimethylformamide).
5-Chloro-3-(3,5-dimethylphenylsulfonyl)-4-fluoroindole-2-carboxyamide (5g), yield 31%, mp 268–270° C. (from ethanol).
4-Chloro-3-(3,5-dimethylphenylsulfonyl)-5-fluoroindole-2-carboxyamide (5h), yield 46%, mp 279–280° C. (from ethanol).
6-Chloro-3-(3,5-dimethylphenylsulfonyl)-5-fluoroindole-2-carboxyamide (5i), yield 50%, mp 262–264° C. (from ethanol).
5-Chloro-3-(3,5-dimethylphenylsulfonyl)-indole-2-carboxyamide (5j), yield 64%, mp 280–284° C. (from ethanol).
5-Nitro-3-(3,5-dimethylphenylsulfonyl)indole-2-carboxyamide (5k), yield 57%, mp 270–272° C. (from ethanol).
5-Acetyl-3-(3,5-dimethylphenylthio)indole-2-carboxyamide (5l), yield 54%, mp>300° C. (from ethanol).

Example 7

Synthesis of N-(3,5-Dimethylphenylthio) succinimide 3,5-Dimethylthiophenol (2.76 g, 0.02 mol) was added by a syringe to an ice cooled mixture of N-chlorosuccinimide (3.34 g, 0.025 mol) and anhydrous dichloromethane (30 mL) under argon atmosphere. After 1 hour, N-chlorosuccinimide (0.4 g, 0.003 mol) was added, then reaction was stirred for 2.5 hours. Triethylamine (3.9 mL, 0.028 mol) was added while stirring for 15 minutes, then dichloromethane and 1N HCl were added. After shaking, organic layer was dried, concentrated to a small volume and passed through a Celite® column. After evaporation of the solvent, the residue was triturated with diethyl ether to give 3.0 g (64%) of title compound, mp 131–134° C. (from diethyl ether).

Example 8

Synthesis of 5-Chloro-3-(3,5-dimethylphenylsulfonyl)indole-2-carboxy-hydrazide (7e)

A mixture of ethyl 5-chloro-3-(3,5-dimethylphenylsulfonyl)-indole-2-carboxylate (1.00 g, 0.0026 mol), hydrazine hydrate (5 mL) and ethanol (5 mL) was stirred at room temperature for 2 hours. After quenching on crushed ice, the solid which formed was filtered, washed with water and dried to give 0.77 (82%) of title compound, mp>300° C. (from aqueous dimethylformamide).
5-Chloro-3-phenylthioindole-2-carboxyhydrazide (6a), yield 80%, mp 231° C. (from ethanol).
5-Chloro-3-(4-methylphenylthio)indole-2-carboxyhydrazide (6b), yield 90%, mp 249–250° C. (from ethanol).
5-Chloro-3-(4-fluoromethylphenylthio)indole-2-carboxyhydrazide (6c), yield 90%, mp 235–236° C. (from ethanol).
5-Chloro-3-(4-chlorophenylthio)indole-2-carboxyhydrazide (6d), yield 100%, mp 247–248° C. (from ethanol).
5-Chloro-3-phenylsulfonylindole-2-carboxyhydrazide (7a), yield 100%, mp>300° C. (from ethanol).
5-Chloro-3-(4-methyhlphenylsulfonyl)indole-2-carboxyhydrazide (7b), yield 100%, mp>300° C. (from ethanol).
5-Chloro-3-(4-fluorophenylsulfonyl)indole-2-carboxyhydrazide (7c), yield 55%, mp 252–253° C. (from ethanol).
5-Chloro-3-(4-chlorophenylsulfonyl)indole-2-carboxyhydrazide (7d), yield 90%, mp>300° C. (from ethanol).

Example 9

Synthesis of 5-Chloro-3-(3,5-dimethylphenylsulfonyl)indole-2-[N'-(2-hydroxyethyl)]-carboxyhydrazide (9f)

A mixture of ethyl 5-chloro-3-(3,5-dimethylphenylsulfonyl)-indole-2-carboxylate (1.00 g, 0.0026 mol), 2-hydroxyethylhydrazine (5 mL) and ethanol (5 mL) was stirred at room temperature overnight. After quenching on crushed ice, the solid which formed was filtered, washed with water and dried to give 0.95 (90%) of title compound, mp 228–230° C. (from ethanol).

5-Chloro-3-phenylthioindole-2-[N'-(2-hydroxyethyl)] carboxyhydrazide (8a), yield 88%, mp 178–180° C. (from ethanol).

5-Chloro-3-(2-methylphenylthio)indole-2-[N'-(2-hydroxyethyl)]carboxyhydrazide (8b), yield 70%, mp 190–192° C. (from ethanol).

5-Chloro-3-(4-methylphenylthio)indole-2-[N'-(2-hydroxyethyl)]carboxyhydrazide (8d), yield 65%, mp 211–213° C. (from aqueous ethanol).

5-Chloro-3-(2,4-dimethylphenylthio)indole-2-[N'-(2-hydroxyethyl)]carboxyhydrazide (8e), yield 59%, mp 170–172° C. (from toluene/cyclohexane).

5-Chloro-3-(3,5-dimethylphenylthio)indole-2-[N'-(2-hydroxyethyl)]carboxyhydrazide (8f), yield 52%, mp 215–217° C. (from ethanol).

5-Chloro-3-phenylsulfonylindole-2-[N'-(2-hydroxyethyl)] carboxyhydrazide (9a), yield 88%, mp 178–180° C. (from ethanol).

5-Chloro-3-(2-methylphenylsulfonyl)indole-2-[N'-(2-hydroxyethyl)]carboxyhydrazide (9b), yield 83%, mp 220–221° C. (from ethanol).

5-Chloro-3-(3-methylphenylsulfonyl)indole-2-[N'-(2-hydroxyethyl)]carboxyhydrazide (9c), yield 98%, mp 210–215° C. (from ethanol).

5-Chloro-3-(4-methylphenylsulfonyl)indole-2-[N'-(2-hydroxyethyl)]carboxyhydrazide (9d), yield 84%, mp 281–283° C. (from ethanol).

5-Chloro-3-(2,4-dimethylphenylsulfonyl)indole-2-[N'-(2-hydroxyethyl)]carboxyhydrazide (9e), yield 94%, mp 141–143° C. (from ethanol).

5-Chloro-3-(3,5-dimethylphenylsulfonyl)indole-2-(N'-methyl)carboxyhydrazide (10), yield 16%, mp 284–287° C. (aqueous dimethylformamide).

Example 10

Synthesis of 5-Chloro-3-(3,5-dimethylphenylsulfonyl)indole-2-(N'-isopropyl)-carboxy-hydrazide (11)

Sodium cyanoborohydride (0.19 g, 0.0031 mol) was added to an ice cooled solution of 5-chloro-3-(3,5-dimethylphenylsulfonyl)indole-2-carboxyhydrazide (7e) (0.98 g, 0.0026 mol), acetone (0.15 g, 0.0026 mol), tetrahydrofuran (32.5 mL) and methanol (32.5 mL) containing 6N HCl—CH$_3$OH 1:1 (0.44 mL). Reaction was stirred at 0° C. for 2 hours, then at room temperature overnight. After concentration to a small volume, water and ethyl acetate were added while shaking. Organic layer was separated, washed with brine and dried. Removal of the solvent gave a residue which was purified by passing through a silica gel column chromatography (chloroform-ethanol 95:5 as eluent) to afford 0.68 g (63%) of title compound, mp 248–250° C. (from ethanol).

Example 11

Synthesis of 5-Chloro-3-(3,5-dimethylphenylsulfonyl)indole-2-carboxylic acid (12)

Lithium hydroxide monohydrate (0.33 g, 0.0079 mol) was added to a solution of methyl 5-chloro-3-(3,5-dimethylphenylthio)indole-2-carboxylate (1.0 g, 0.0026 mol) in tetrahydrofuran (30 mL) and water (30 mL), then reaction was stirred at room temperature for 4 days. After dilution with water the mixture was acidified with 1N HCl and extracted with ethyl acetate. Organic reaction was washed with brine and dried. Evaporation of the solvent furnished 0.94 (100%) of title compound, mp 277–278° C. (from ethanol).

Example 12

Synthesis of 1-[5-Chloro-3-(3,5-dimethylphenylsulfonyl)indole-2-carbonyl]-4-methyl-piperazine (13)

Benzotriazol-1-yl-oxy-tris(dimethylamino)phosphonium hexafluorophosphate (BOP reagent) (1.22 g, 0.00275 g) was added to a solution of 5-chloro-3-(3,5-dimethylphenylsulfonyl)indole-2-carboxylic acid (12) (1.00 g, 0.00275 mol), N-methylpiperazine (0.55 g, 0.0055 mol), triethylamine (0.55 g, 0.0055 mol) in anhydrous DMF (50 mL). Reaction was stirred at room temperature for 72 hours, then diluted with water and extracted with ethyl acetate. Organic extracts were washed with brine, dried and the solvent evaporated to give 1.20 g (98%) of pure title compound, mp 281–283° C. (from aqueous ethanol).

N-Methyl,N-methoxy 5-chloro-3-(3,5-dimethylphenylsulfonyl)indol-2-carboxyamide (14), was prepared using N,O-dimethylhydroxylamine hydrochloride. Yield 70%, mp 264–267° C. (ethanol).

Example 13

Synthesis of 5-Chloro-3-(3,5-dimethylphenylsulfonyl)indol-2-carboxy-aldehyde (15)

A 1M solution of lithium aluminium hydride (1.6 mL, 0.0015 mol) was slowly added via syringe to a solution of 14 (0.6 g, 0.0015 mol) in anhydrous tetrahydrofuran (40 mL) under argon atmosphere. Reaction was stirred at room temperature for 1.5 hours, then quenched by carefully addition of crushed ice. The solid that formed was filtered, washed with tetrahydrofuran and concentrated to a small volume. After extraction with ethyl acetate, the organic layer was washed with brine and dried. Removal of the solvent furnished 0.5 g (96%) of satisfactory pure title compound, mp 253–255° C. (from aqueous ethanol).

Example 14

Synthesis of Ethyl 3-trans-[5-chloro-3-(3,5-dimethylphenylsulfonyl)indol-2-yl]propionate (16)

Triethyl phosphonoacetate (0.36 g, 0.016 mol) was added in one portion to a mixture of 15 (0.45 g, 0.0013 mol), potassium carbonate (0.53 g, 0.0039 mol) and absolute ethanol (10 mL), then reaction was stirred at 70° C. per 2 hours. After cooling water and diethyl ether were added while shaking. The organic layer was separated, washed with brine and dried. After evaporation of the solvent, the crude product was purified by passing through a silica gel column chromatography (ethyl acetate as eluent) to give 0.27 g (50%) of pure title compound, mp 236–238° C. (from ethanol).

Example 15

Synthesis of 3-trans-[5-Chloro-3-(3,5-dimethylphenylsulfonyl)indol-2-yl]-propionic acid (17)

Was prepared by lithium hydroxide hydrolysis of 16, as reported above for acid 12. After 48 hours was obtained

Example 16

Synthesis of 3-trans-[5-Chloro-3-(3,5-dimethylphenylsulfonyl)indol-2-yl]-propionamide (18)

1,1'-Carbonyldiimidazole (0.24 g, 0.0015 mol) was added by portions to an ice water cooled solution of 17 in anhydrous tetrahydrofuran. Reaction was stirred at room temperature for 2 hours, then gaseous ammonia was bubbled through for 30 minutes. After dilution with water, the mixture was extracted with ethyl acetate, washed with brine and dried. Removal of the solvent gave a residue, which was purified by passing through a silica gel column chromatography (ethyl acetate/ethanol 9:1 as eluent). Evaporation of the eluent gave 0.19 g (51%) of title compound, mp>300° C. (from aqueous dimethylformamide).

Example 17

Synthesis of 2-[N-[3-trans-[5-Chloro-3-(3,5-dimethylphenylsulfonyl)indol-2-yl]propion-amido]]-acetic Acid Ethyl Ester (19)

Benzotriazol-1-yloxy-tris(dimethylamino)phosphonium hexafluorophosphate (BOP reagent) (0.90 g, 0.0020 mol) was added to a solution of 3-trans-[5-chloro-3-(3,5-dimethylphenylsulfonyl)indol-2-yl]propionic acid (17) (0.80 g, 0.0020 mol), glycine ethyl ester hydrochloride (0.57 g, 0.0041 mol) and triethylamine (0.62 g, 0.0061 mol) in anhydrous DMF (37 mL). Reaction was stirred at room temperature for 48 hours, then diluted with water and extracted with ethyl acetate. Organic layer was separated, washed with brine and dried. Removal of the solvent furnished 0.8 g (82%) of satisfactory pure title compound, mp 278–280° C. (from ethanol).

2-[N-[5-Chloro-3-(3,5-dimethylphenylsulfonyl)indol-2-carboxy-amido]]acetic acid ethyl ester (21), was prepared from 5-chloro-3-(3,5-dimethylphenylsulfonyl)indole-2-carboxylic acid (12)—after 72 hours at room temperature the reaction mixture was diluted with water; the solid which formed was filtered, washed with water and dried to give 0.62 g (80%) of satisfactory pure title compound, mp 209–211° C. (from ethanol).

Example 18

Synthesis of 2-[N-[3-trans-[5-Chloro-3-(3,5-dimethylphenylsulfonyl)indol-2-yl]propion-amido]]-acetamide (20)

A suspension of 19 (0.30 g, 0.0006 mol), in ethanol (28 mL) and 30% ammonium hydroxide (17 mL) was stirred at 60° C. for 1.5 hours. After cooling the mixture was diluted with water and extracted with ethyl acetate. Organic layer was separated, washed with brine and dried. Removal of the solvent furnished 0.2 g (65%) of pure title compound, mp>300° C. (from ethanol).

2-[N-[5-Chloro-3-(3,5-dimethylphenylsulfonyl)indol-2-carboxy-amido]]-acetamide (22), was prepared from 2-[N-[5-chloro-3-(3,5-dimethylphenylsulfonyl)indol-2-carboxyamido]]-acetic acid ethyl ester (21)—the crude product was passed through a silica gel column chromatography (ethyl acetate), yield 95%, mp 265–267° C. (aqueous dimethylformamide).

Example 19

Synthesis of N-Cyclopropyl 2-[N-[5-Chloro-3-(3,5-dimethylphenylsulfonyl)-indol-2-carboxyamido]] acetamide (23)

A mixture of 2-[N-[5-chloro-3-(3,5-dimethylphenylsulfonyl)indol-2-carboxy-amido]]-acetic acid ethyl ester (21), ethanol (5 mL) and cyclopropylamine (5 mL) was heated at 60° C. for 6hours. After concentration to a small volume, the residue was extracted with ethyl acetate, washed with brine and dried. Removal of the solvent furnished a crude product which was purified by passing through a silica gel column chromatography (ethyl acetate) to give 0.14 g (69%) of title compound, mp 267–270° C. (ethanol).

N-(1-Morpholin-4-yl)-2-[N-[5-Chloro-3-(3,5-dimethylphenylsulfonyl)indol-2-carboxy-amido]]-acetamide (24), was prepared using morpholine—after 48 hours at 60° C., yield 74%, mp>300° C. (ethanol).

Example 20

Synthesis of 5-(1H-Pyrrol-1-yl)-3-(3,5-dimethylphenylsulfonyl)indole-2-carboxyamide (25b)

A solution of 5-nitro-3-(3,5-dimethylphenylsulfonyl)indole-2-carboxyamide (5k) (0.25 g, 0.0007 mol) in tetrahydrofuran (40 ML) and methanol (16 mL) was reduced under an atmospheric pressure of hydrogen in the presence of $PtO_2$ (50 mg) as a catalyst for 6 hours. Catalyst was separated by filtration and the solvent evaporated to give 0.227 g (100%) of pure 5-amino-3-(3,5-dimethylphenylsulfonyl)indole-2-carboxyamide as a brown oil. A solution of the last compound (0.227 g, 0.0007 mol), 2,5-dimethoxythetrahydrofuran (0.09 g, 0.0006 mol) in glacial acetic acid (5 mL) was refluxed for 30 minutes. After evaporation of the solvent the residue was triturated with ice water and extracted with ethyl acetate. Organic layer was washed with brine and dried. Removal of the solvent left the crude product which was purified by passing through a silica gel column chromatography (ethyl acetate as eluent) to give 0.15 g (57%) of title compound, mp 270–272° C. (from ethanol).

5-(1H-Pyrrol-1-yl)-3-(phenylsulfonyl)indole-2-carboxyamide (25a), was prepared from 5-nitro-3-(phenylsulfonyl)indole-2-carboxyamide, yield 71%, mp 250° C. (ethanol).

Example 21

Synthesis of 5-(1-Hydroxyethyl)-3-(3,5-dimethylphenylsulfonyl)indole-2-carboxyamide (26)

Sodium borohydride (0.03 g, 0.0008 mol) was added to a mixture of 5-acetyl-3-(3,5-dimethylphenylsulfonyl)indole-2-carboxyamide (51) (0.30 g, 0.0008 mol) in tetrahydrofuran (8.5 mL) containing 0.1 mL of water, then reaction was refluxed for 1 hour. After cooling, water was added while stirring for a few minutes, then the mixture was extracted with ethyl acetate, washed with brine and dried. Removal of the solvent furnished 0.25 g (83%) of satisfactory pure title compound, mp 260–260° C. (ethanol).

Example 22

Preparation of 4,5-difluoro-3-(3,5-dimethylphenylsulphonyl) indole-2-carboxyserinamide 4,5-Difluoro-3-(3,5-dimethylphenylsulphonyl)indole 2-carboxylic acid (3.52 g) and L-serinamide hydrochloride (2.77 g) were dissolved in anhydrous dimethylformamide (90 ml). Triethylamine (2.8 ml) was added and the mixture stirred for 5 min. Benzotriazol-1-yloxy-tris(dimethylamino) phosphonium hexafluorophosphate (BOP) (4.69 g) was added and the orange mixture was stirred overnight at room temperature. The reaction mixture was diluted with water (350 ml) and the white solid precipitate collected by filtration, washed with water and dried to afford the title product (3.86 g) as a white powder (97.9% pure by hplc).

In a similar manner 5-chloro-4-fluoro-3-(3,5-dimethylphenylsulphonyl) indole-2-carboxyserinamide was prepared from the 5-chloro-4-fluoro-3-(3,5-dimethylphenylsulphonyl) indole-2-carboxylic acid. The product was obtained as a white solid.

Example 23

Preparation of 4,5-difluoro-3-(3,5-dimethylphenylsulphonyl) indole-2-(2-(1-pyrrolo) ethyl)carboxamide 4,5-difluoro-3-(3,5-dimethylphenylsulphonyl)indole 2-carboxylic acid (4.22 g) and 2-(1-pyrrolo)ethylamine (2.63 g) were dissolved in anhydrous dimethylformamide under an atmosphere of nitrogen (100 ml) and triethylamine (3.2 ml) was added. Benzotriazol-1-yloxy-tris (dimethylamino)phosphonium hexafluorophosphate (BOP)(5.63 g) was added and the yellow solution was stirred at room temperature for 18 hours. The reaction mixture was diluted with water (350 ml) and stirred for 30 min. The white precipitate was collected by filtration, washed with water and dried to afford the title product (5.18 g) as a white powder (97.1% pure by hplc).

In a similar manner 5-chloro-4-fluoro-3-(3,5-dimethylphenylsulphonyl) indole-2-(2-(1-pyrrolo)ethyl) carboxamide was prepared from the 5-chloro-4-fluoro-3-(3, 5-dimethylphenylsulphonyl) indole-2-carboxylic acid. The product was obtained as a white solid.

Example 24

Preparation of 4,5-difluoro-3-(3,5-dimethylphenylsulphonyl) indole-2-(1-morpholinomethyl)carboxamide 4,5-difluoro-3-(3,5-dimethylphenylsulphonyl)indole 2-carboxamide (670 mg) was mixed with 1,4-dioxan (18 ml) and the resultant white slurry was heated to reflux temperature. Morpholine (0.8 ml) and 37% aqueous formaldehyde (0.7 ml) were added and the mixture rapidly became homogeneous and was refluxed for 24 hours then allowed to cool and poured into water (75 ml). The white slurry was stirred at room temperature for 4 hrs and the white solid was collected by filtration, washed with water and dried to afford the title product (730 mg) as a white powder.

In similar fashion 5-chloro-4-fluoro-3-(3,5-dimethylphenylsulphonyl) indole-2-(1-morpholinomethyl) carboxamide was prepared from 5-chloro-4-fluoro-3-(3,5-dimethylphenylsulphonyl)indole 2-carboxamide. The product was obtained as a white solid.

VII. Biological Activity Against Drug Resistant Strains of HIV

In one embodiment the phenylindoles of the present invention do not exhibit significant cross resistance with other non-nucleosides reverse transcriptase inhibitors (NNRTI), in that it displays an $EC_{50}$ (in molar concentrations) in a mutant HIV strain of less than approximately 50, 25, 10 or 1 micromolar concentration. In a preferred embodiment, the non-nucleosides reverse transcriptase inhibitors (NNRTI) displays an $EC_{50}$ (in molar concentrations) in a mutant HIV strain of less than approximately 5, 2.5, 1 or 0.1 micromolar concentration. The degree of cross-resistance against a drug resistant strain of HIV can easily be measured by assessing the $EC_{50}$ of the desired indole in the target mutated i.e., drug resistant, virus.

Therefore, in another important embodiment of this invention, a method for treating a patient with a cross-resistant HIV is provided that includes administering an effective HIV-treatment amount of a phenylindole or its prodrug or salt.

Example 25

Influence of Phenyl Substitution and Amido Group on Protein

Binding in Presence of Glycoprotein or Human Serum Albumin

In order to understand how variations in the substituents on the phenyl ring, and variations at the 2-position of the indole ring, in this class of compounds influence protein binding, a number of representative phenylindoles were tested in the presence of glycoprotein or human serum albumin, and compared to the prototype NNRTIs efavirenz and nevirapine. The structure of the tested compound is given below, and the test results presented in Tables 1 and 2.

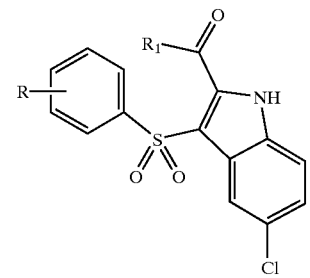

TABLE 1

| | Substituents | | | $EC_{90}$ (Nx)$^d$ | |
| | | | | α-GP$^b$ | HSA$^c$ |
| Cmpd. | R | R$_1$ | RPMI$^a$ | 1 mg/mL | 45 mg/mL |
|---|---|---|---|---|---|
| 1* | H | NH$_2$ | 0.001 | 0.002 (2x) | 0.01 (10x) |
| 2 | 3,5 diMe | NH$_2$ | 0.005 | 0.01 (2x) | 0.2 (40x) |
| 3 | 3,5 diMe | NHNHC$_2$H$_5$OH | 0.004 | 0.03 (7x) | 0.27 (67x) |
| 4 | 3,5 diMe | NHCH$_2$CONH$_2$ | 0.06 | 0.2 (3x) | 4.8 (80x) |
| EFV | | | 0.01 | 0.02 (2x) | 0.13 (13x) |

$^a$Compound concentration (μM) required to reduce the amount of p24 by 90% in HIV-1-infected MT-4 cells incubated in RPMI 10% FCS.
$^b$Compound concentration (μM) required to reduce the amount of p24 by 90% in HIV-1-infected MT-4 cells incubated in RPMI 10% FCS in the presence of 1 mg/mL γ-acidic glycoprotein (γGP).
$^c$Compound concentration (μM) required to reduce the amount of p24 by 90% in HIV-1-infected MT-4 cells incubated in RPMI 10% FCS in the presence of 45 mg/mL human serum albumin (HSA).
$^d$Protein binding shift.

TABLE 2

| Compd. | Substituents | | WT$_{IIIB}$ | | K103R | Y181C | K103N-Y181C |
|---|---|---|---|---|---|---|---|
| (CC$_{50}$)$^a$ | R | R$_1$ | EC$_{50}$$^b$ | EC$_{90}$ | EC$_{90}$$^d$ | EC$_{50}$ | EC$_{50}$ |
| 4 (30) | 3,5 diMe | NHCH$_2$CO-NH$_2$ | 0.006 | 0.01 | 0.1 (10) | 0.03 (5) | 0.8 (133) |
| 5 (≧200) | 3,5 diMe | NHCH$_2$CO-NHNH$_2$ | 0.01 | 0.03 | 1 (33) | 0.05 (5) | 2 (200) |
| 6 (>200) | 3,5 diMe | CH=CHCO-NH$_2$ | 0.06 | 0.03 | >100 | 0.6 (10) | >100 (1666) |
| 7 (71) | 3,5 diMe | NHCH$_2$CH$_2$-(2NO$_2$,5Me imidazole) | 0.01 | 0.07 | 7 (100) | 0.7 (70) | 10 (1000) |
| NVP (200) | | | 0.37 | | | >30 | >30 |
| EFV (35) | | | 0.004 | 0.008 | 1.8 (225) | 0.025 (6) | 0.15 (38) |

$^a$Compound concentration (μM) required to reduce the viability of mock-infected MT-4 cells by 50%, as determined by the MTT method.
$^b$Compound concentration [μM] required to a achieve 50% protection of MT-4 cells from the HIV-1-induced cytopathogenicity, as determined by the MTT method.
$^c$Compound concentration [μM] required to reduce the amount of p24 by 90% in virus-infected C8166 cells.
$^d$(Nx) resistance shift.

Example 26

Influence of Substituents on the Indole Nucleus

Example 26 illustrates the influence of substituents at positions 4, 5, 6, and 7 of the indole ring, in which position 2 of the indole ring is maintained constant, and the substitution at the 3,5-position of the phenyl ring is either hydrogen or held constant with a 3,5-dimethyl substitution. Table 3 presents the influence of these variations on the ability of the compounds to protect cells from HIV-1 induced pathogenecity. Comparisons are again made to nevirapine and efavirenz.

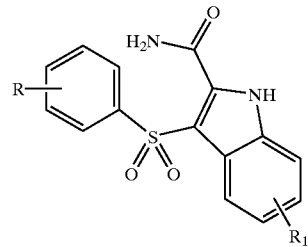

TABLE 3

| Compd | Substituents | | WT$_{IIIB}$ | | K103R | Y181C | K103N-Y181C |
|---|---|---|---|---|---|---|---|
| (CC$_{50}$)$^a$ | R | R$_1$ | EC$_{50}$$^b$ | EC$_{90}$ | EC$_{90}$$^d$ | EC$_{50}$ | EC$_{50}$ |
| 8 (123) | H | 5,6 Cl | 0.14 | 0.17 | 16 (94) | 2.6 (18) | >100 (>714) |
| 9 (19) | 3,5 Me | 5,6 Cl | 0.03 | 0.07 | 0.3 (4) | 1.7 (57) | >100 (>3333) |
| 10 (>200) | 3,5 Me | 5,7 Cl | 1.6 | 1.2 | >100 (>83) | >100 | >100 (>62.5) |
| 11 (17) | 3,5 Me | 4,5 F | 0.02 | | | 0.7 (35) | >200 |
| 12 ( ) | 3,5 Me | 5,6 F | ≦0.003 | | | 0.07 (≧23.3) | 2.6 (≧866) |
| 13 (>200) | 3,5 Me | 5,7 F | 0.01 | 0.02 | >100 (>5000) | 2 (200) | >100 (>10000) |
| NVP (200) | | | 0.37 | | | >30 | >30 |
| EFV (35) | | | 0.004 | 0.008 | 1.8 (225) | 0.025 (6) | 0.15 (38) |

$^a$Compound concentration (μM) required to reduce the viability of mock-infected MT-4 cells by 50%, as determined by the MTT method.
$^b$Compound concentration [μM] required to a achieve 50% protection of MT-4 cells from the HIV-1-induced cytopathogenicity, as determined by the MTT method.
$^c$Compound concentration [μM] required to reduce the amount of p24 by 90% in virus-infected C8166 cells.
$^d$(Nx) resistance shift.

This invention has been described with reference to its preferred embodiments. Variations and modifications of the invention, will be obvious to those skilled in the art from the foregoing detailed description of the invention. It is intended that all of these variations and modifications be included within the scope of this invention.

We claim:

1. A compound of the formula (I):

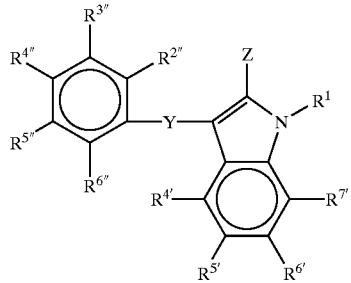

or a pharmaceutically acceptable salt thereof, wherein
   a) $R^1$ is hydrogen; acyl; —C(=O)H; —C(=W)H; —C(=O)$R^2$; —C(=W)$R^2$; —C(=O)OH; —C(=W)OH; —C(=O)O$R^2$; —C(=W)O$R^2$; —C(=O)SH; —C(=W)SH; —C(=O)S$R^2$; —C(=W)S$R^2$; —C(=O)N$H_2$; —C(=W)N$H_2$; —C(=O)NH$R^2$; —C(=W)NH$R^2$; —C(=O)N$R^2R^3$; —C(=W)N$R^2R^3$; —C(=W)NH—(C$H_2$)$_p$-(amino acid) or —(C$H_2$)$_p$-(amino acid);
   b) $R^{4'}$, $R^{5'}$, $R^{6'}$, $R^{7'}$, $R^{2''}$, $R^{3''}$, $R^{4''}$, $R^{5''}$ and $R^{6''}$ are each independently H; halo; —N$O_2$; —CN; —OH; —O$R^2$; —SH; —S$R^2$; —N$H_2$; —NH$R^2$; —N$R^2R^3$; —NHS$O_2$—$C_{1-3}$alkyl; —N$R^2$S$O_2$—$C_{1-3}$alkyl; —NHCO—$C_{1-3}$alkyl; —N$R^2$CO—$C_{1-3}$alkyl; optionally substituted or unsubstituted branched or unbranched alkyl, alkenyl or alkynyl; C$H_3$, C$F_3$, vinyl bromide, —C$R^2R^2$—S(O)$_n$—$R^3$, —C$R^2R^2$N$H_2$, —C$R^2R^2$NH$R^2$, —C$R^2R^2$N$R^2R^3$ or —C$R^2R^2$—C(=O)$R^2$; alkacyl; optionally substituted or unsubstituted acyl; —C(=O)H; —C(=W)H; —C(=O)$R^2$; —C(=W)$R^2$; —C(=O)OH; —C(=W)OH; —C(=O)O$R^2$; —C(=W)O$R^2$; —C(=O)—SH; —C(=W)SH; —C(=O)S$R^2$; —C(=W)S$R^2$; —C(=O)N$H_2$; —C(=W)N$H_2$; —C(=O)NH$R^2$; —C(=W)NH$R^2$; —C(=O)N$R^2R^3$; —C(=W)—N$R^2R^3$; —C(=W)NH(C$H_2$)$_p$-(amino acid), a residue of an amino acid or —(C$H_2$)$_p$(amino acid); wherein if $R^{5'}$ is hydrogen, F, Cl, Br, —N$O_2$, —CN, —O$R^2$, —N$R^2R^2$, —NHS$O_2$—$C_{1-3}$alkyl or —NHCO—$C_{1-3}$alkyl, then at least one of $R^{4'}$, $R^{6'}$ and $R^{7'}$ is not hydrogen or alternatively, wherein at least two of $R^{4'}$, $R^{5'}$, $R^{6'}$, $R^{7'}$ are not hydrogen;
   c) Z is optionally substituted or unsubstituted acyl, —C(=O)N$H_2$; —C(=W)—N$H_2$; —C(=O)NH$R^2$; —C(=W)NH$R^2$; —C(=O)N$R^2R^3$; —C(=W)N$R^2R^3$; —C(=W)NH(C$H_2$)$_p$-(amino acid); a residue of an amino acid, —(C$H_2$)$_p$-(amino acid); —C(=O)$R^3$; —C(=O)H; —C(=W)H; —C(=O)$R^2$; —C(=O)O$R^3$; —C(=O)OH; —C(=W)OH; —C(=O)O$R^2$; —C(=W)O$R^2$; —C(=O)—SH; —C(=W)SH; —C(=O)S$R^2$; —C(=W)S$R^2$; optionally substituted or unsubstituted branched or unbranched alkyl, alkenyl or alkynyl; C$H_3$, C$F_3$, vinyl bromide, —C$R^2R^2$—S(O)$_n$—$R^3$, —C$R^2R^2$N$H_2$, —C$R^2R^2$NH$R^2$, —C$R^2R^2$N$R^2R^3$ or —C$R^2R^2$—C(=O)$R^2$; —CN, or halo;
   d) Y is O, S or S(O)$_n$;
   e) each W is independently O, S, —N$H_2$, —NH$R^2$, —N$R^2R^2$, —N—CN, —N—N$H_2$, —N—NH$R^2$, —N—N$R^2R^3$, —N—OH or —N—O$R^2$;
   f) each $R^2$ is independently hydrogen or an optionally substituted or unsubstituted branched or unbranched lower alkyl, alkenyl or alkynyl; or C$H_3$, C$F_3$, vinyl bromide, —C$R^2R^2$—S(O)$_n$—$R^3$, —C$R^2R^2$N$H_2$, —C$R^2R^2$NH$R^2$, —C$R^2R^2$N$R^2R^3$ or —C$R^2R^2$—C(=O)$R^2$;
   (g) each $R^3$ is independently hydrogen; optionally substituted or unsubstituted branched or unbranched alkyl, alkenyl or alkynyl; C$H_3$C$F_3$, vinyl bromide, —C$R^2R^2$—S(O)$_n$—$R^3$, —C$R^2R^2$N$H_2$, —C$R^2R^2$NH$R^2$, —C$R^2R^2$N$R^2R^3$ or —C$R^2R^2$—C(=O)$R^2$); optionally substituted or unsubstituted aryl; optionally substituted or unsubstituted heterocycle; optionally substituted or unsubstituted alkylaryl; optionally substituted or unsubstituted alkylhereterocycle; optionally substituted or unsubstituted aralkyl; or optionally substituted or unsubstituted heterocyclealkyl;
   h) each n is independently 0, 1 or 2;
   i) each p is independently 0, 1, 2, 3, 4 or 5; and
   j) wherein an optionally substituted branched or unbranched alkyl, alkenyl, alkynyl, lower alkyl, lower alkenyl or lower alkynyl; acyl; aryl; heterocycle; alkaryl; alkheterocycle; arylalkyl or alkylheterocycle substitutents is substituted with one or more of halogen —OH, —O$R^2$, —SH, —S$R^2$, oxime, hydrazine —C(=O)H, —C(=W)H, —C(=O)$R^2$, —C(=W)$R^2$, —C(=O)OH, —C(=W)OH, —C(=O)O$R^2$, —C(=W)O$R^2$, —C(=O)SH, —C(=W)SH, —C(=O)S$R^2$, —C(=W)S$R^2$, —C(=O)N$H_2$, —C(=W)N$H_2$, —C(=O)—NH$R^2$, —C(=W)NH$R^2$, —C(=O)N$R^2R^3$, —C(=W)—N$R^2R^3$, —N$H_2$, —NH$R^2$, —N$R^2R^3$, —NHS$O_2$—$C_{1-3}$alkyl, —N$R^2$S$O_2$—$C_{1-3}$alkyl, —NHCO—$C_{1-3}$alkyl, —N$R^2$CO—$C_{1-3}$alkyl, —S(O)$_n$—$R^3$, $C_{1-3}$ alkoxy, $C_{1-3}$thioether, or an amino acid residue.

2. The compound of claim 1, wherein Y is S$O_2$.
3. The compound of claim 1, wherein Z is an amide.
4. The compound of claim 1, wherein $R^1$ is hydrogen.
5. The compound of claim 1, wherein
   a) $R^1$ is hydrogen;
   b) $R^{4'}$, $R^{5'}$, $R^{6'}$ and $R^{7'}$ are independently hydrogen, halogen, —N$O_2$, —CN, —O$R^2$, —N$R^2R^2$, —NHS$O_2$—$C_{1-3}$alkyl, —NHCO—$C_{1-3}$alkyl, oxime, hydrazine, or $C_{1-3}$ alkyl or alkenyl optionally substituted with one or more of —OH, —SH, —C(O)H, —COOH, halogen, —N$R^2R^2$, —$C_{1-3}$ alkoxy or —$C_{1-3}$ thioether; wherein if $R^{5'}$ is hydrogen, F, Cl, Br, —N$O_2$, —CN, —O$R^2$, —N$R^2R^2$, —NHS$O_2$—$C_{1-3}$alkyl or —NHCO—$C_{1-3}$alkyl, then at least one of $R^{4'}$, $R^{6'}$ and $R^{7'}$ is not hydrogen;
   c) $R^{2''}$, $R^{3''}$, $R^{4''}$, $R^{5''}$ and $R^{6''}$ are independently hydrogen, halogen, —N$O_2$, —CN, —OH, —O$R^2$, —N$R^2R^2$, —NHS$O_2$—$C_{1-3}$alkyl, —NHCO—$C_{1-3}$alkyl, —$C_{1-5}$ alkoxy, oxime, hydrazine, —$C_{1-5}$ alkyl or alkenyl optionally substituted with one or more of —OH, —SH, —C(O)H, —COOH, halogen, —N$R^2R^2$, —$C_{1-5}$ thioether or —$C_{1-5}$ alkoxy;
   d) Z is —CN, —C(=W)N$R^2R^3$, —C(=O)$R^3$, —C(=O)O$R^3$, —C$R^2R^2$—S(O)$_n$—$R^3$, —C$R^2R^2$NH$R^2$, —C$R^2R^2$—CO—$R^3$ or substituted or unsubstituted lower alkyl;

e) Y is O, S, or S(O)$_n$;

f) each W is independently O, S, —N—CN or —N—OR$^2$;

g) R$^2$ is hydrogen or C$_{1-3}$ alkyl;

h) R$^3$ is hydrogen, substituted or unsubstituted alkyl, alkenyl, aryl, or heterocycle, —C$_{1-5}$ alkoxy, —OH, —NR$^2$R$^2$, or —(CH$_2$)$_p$C(O)NR$^2$R$^2$;

i) each n is independently 0, 1 or 2; and j) each p is independently 0, 1, 2, 3, 4, or 5.

6. The compound of claim 1, wherein a) R$^1$ is hydrogen;

b) R$^{4'}$, R$^{5'}$, R$^{6'}$, R$^{7'}$, are independently hydrogen, halogen, —NO$_2$, —CN, —OR$^2$, —NR$^2$R$^2$, —NHSO$_2$—C$_{1-3}$ alkyl, —NHCO—C$_{1-3}$alkyl, oxime, hydrazine, or C$_{1-3}$ alkyl or alkenyl optionally substituted with one or more of —OH, —SH, C(O)H, COOH, halogen, NR$^2$R$^2$, C$_{1-3}$ alkoxy, or C$_{1-3}$ thioether; wherein if R$^{5'}$ is hydrogen, F, Cl, Br, —NO$_2$, —CN, —OR$^2$, —NR$^2$R$^2$, —NHSO$_2$—C$_{1-3}$alkyl or —NHCO—C$_{1-3}$alkyl, then at least one of R$^{4'}$, R$^{6'}$ and R$^{7'}$ is not hydrogen;

c) R$^{2''}$, R$^{3''}$, R$^{4''}$, R$^{5''}$, and R$^{6''}$, are independently hydrogen, halogen, —NO$_2$, —CN, —OR$^2$, —NHSO$_2$—C$_{1-3}$alkyl, —NHCO—C$_{1-3}$alkyl, oxime, hydrazine, —C$_{1-5}$ alkyl or alkenyl optionally substituted with one or more of —OH, —SH, C(O)H, COOH, halogen, NR$^2$R$^2$, C$_{1-5}$ thioether, or C$_{1-5}$ alkoxy, —C$_{1-5}$ alkoxy, —OH, or —NR$^2$R$^2$;

d) Z is —C(W)NR$^2$R$^3$, or —COR$^3$;

e) Y is —S(O)$_n$— or —O—, in which n is 0, 1 or 2;

f) W is O, S, —N—CN or —N—OR$^2$;

g) R$^2$ is hydrogen or C$_{1-3}$ alkyl;

h) R$^3$ is C$_{1-5}$ alkyl, C$_{1-5}$ alkenyl, aryl, or heterocycle, substituted with one or more of C(O)NR$^2$R$^2$, —NR$^2$R$^2$, —(CH$_2$)$_m$C(O)NR$^2$R$^2$, —(CH$_2$)$_m$C(=W)—NH(CH$_2$)$_p$- (amino acid);

i) each n is independently 0, 1 or 2; and j) each p is independently 0, 1, 2, 3, 4, or 5.

7. A compound of the formula

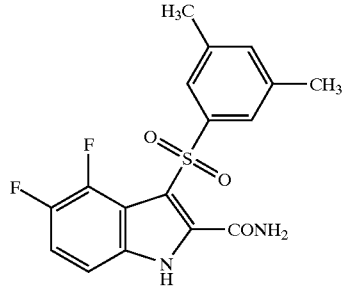

or a pharmaceutically acceptable salt thereof.

8. A compound of the formula

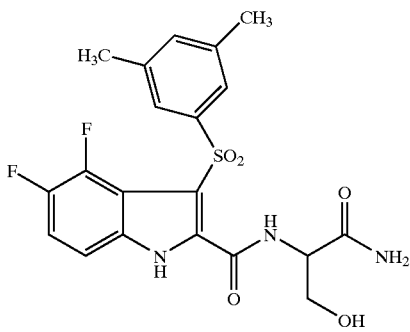

or a pharmaceutically acceptable salt thereof.

9. A compound of the formula

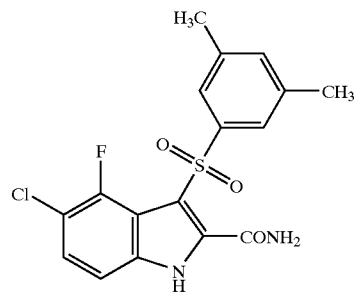

or a pharmaceutically acceptable salt thereof.

10. A compound of the formula

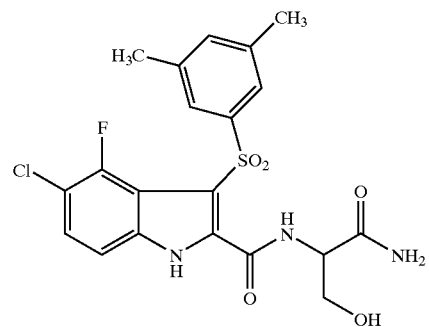

or a pharmaceutically acceptable salt thereof.

11. A pharmaceutical composition comprising an effective anti-HIV treatment amount of a compound of claim 1, or its pharmaceutically acceptable salt thereof, together with a pharmaceutically acceptable carrier or diluent.

12. A pharmaceutical composition comprising an effective anti-HIV treatment amount of a compound of claim 1, or a pharmaceutically acceptable salt thereof, in combination with at least one other anti-HIV agent, optionally with a pharmaceutically acceptable carrier or diluent.

13. The pharmaceutical composition of claim 12, wherein the other anti-HIV agent is a reverse transcriptase inhibitor.

14. The pharmaceutical composition of claim 13, wherein the reverse transcriptase inhibitor induces a mutation lysine 103→asparagine and/or tyrosine 181→cysteine in HIV reverse transcriptase.

* * * * *